United States Patent
de Beaubien et al.

(10) Patent No.: US 12,383,404 B2
(45) Date of Patent: Aug. 12, 2025

(54) TOTAL JOINT REPLACEMENT INFECTION CONTROL DEVICES AND METHODS

(71) Applicant: Osteal Therapeutics, Inc., Dallas, TX (US)

(72) Inventors: Brian C. de Beaubien, Dallas, TX (US); Brian Bowman, Dallas, TX (US); Benjamin Arnold, Dallas, TX (US); Erika Lin, Dallas, TX (US); Kristen Pena, Dallas, TX (US); Tina John, Dallas, TX (US)

(73) Assignee: Osteal Therapeutics, Inc., Dallas, TX (US)

( * ) Notice: Subject to any disclaimer, the term of this patent is extended or adjusted under 35 U.S.C. 154(b) by 372 days.

(21) Appl. No.: 17/971,080

(22) Filed: Oct. 21, 2022

(65) Prior Publication Data
US 2023/0041597 A1 Feb. 9, 2023

Related U.S. Application Data

(60) Continuation of application No. 16/513,599, filed on Jul. 16, 2019, now Pat. No. 11,504,242, which is a (Continued)

(51) Int. Cl.
*A61F 2/36* (2006.01)
*A61F 2/30* (2006.01)
(Continued)

(52) U.S. Cl.
CPC ........ *A61F 2/3609* (2013.01); *A61F 2/30907* (2013.01); *A61F 2/34* (2013.01); (Continued)

(58) Field of Classification Search
CPC .............. A61F 3/36; A61F 2002/30677; A61F 2002/3068; A61F 2002/365; A61F 2/30; (Continued)

(56) References Cited

U.S. PATENT DOCUMENTS 3,648,294 A 3/1972 Shahrestani
4,274,163 A 6/1981 Malcom et al.
(Continued)

FOREIGN PATENT DOCUMENTS

CN 104168857 A 11/2014
DE 3704089 A1 8/1988
(Continued)

OTHER PUBLICATIONS

Ekpo, T.E. et al. (Sep. 22, 2012). "Abbreviated Two-Stage Exchange Arthroplasty for Periprosthetic Joint Infection: 2 to 6 Year Results." [Poster presentation]. 31st Annual meeting of the European Bone and Joint Infection Society, Montreux, Switzerland. 1 page.
(Continued)

*Primary Examiner* — Laura A Bouchelle
(74) *Attorney, Agent, or Firm* — Mintz Levin Cohn Ferris Glovsky and Popeo, P.C.

(57) ABSTRACT

An orthopedic system for delivery of a therapeutic agent to a bone includes an elongate stem adapted to be inserted into an intramedullary canal, an inlet configured to receive the therapeutic agent, and one or more outlets configured to deliver the therapeutic agent to the bone. The elongate stem may comprise one or more protrusions to engage the bone, and one or more channels extending longitudinally therein, fluidly coupled to the inlet. The therapeutic agent flows from the inlet through the one or more channels and exits into the intramedullary canal through the one or more outlets. The system may be configured to allow one or more dimensions of the system to be adjusted to accommodate the anatomy of a patient.

20 Claims, 38 Drawing Sheets

Related U.S. Application Data division of application No. 14/841,529, filed on Aug. 31, 2015, now Pat. No. 10,433,965.

(60) Provisional application No. 62/180,986, filed on Jun. 17, 2015.

(51) Int. Cl.
 *A61F 2/34* (2006.01)
 *A61F 2/38* (2006.01)
 *A61F 2/40* (2006.01)
 *A61F 2/42* (2006.01)

(52) U.S. Cl.
 CPC .................. *A61F 2/36* (2013.01); *A61F 2/38* (2013.01); *A61F 2/40* (2013.01); *A61F 2/4202* (2013.01); *A61F 2002/30387* (2013.01); *A61F 2002/30405* (2013.01); *A61F 2002/30507* (2013.01); *A61F 2002/30517* (2013.01); *A61F 2002/3055* (2013.01); *A61F 2002/30593* (2013.01); *A61F 2002/30672* (2013.01); *A61F 2002/30677* (2013.01); *A61F 2002/3068* (2013.01); *A61F 2002/30784* (2013.01); *A61F 2002/30825* (2013.01); *A61F 2002/30827* (2013.01); *A61F 2002/30878* (2013.01); *A61F 2002/30919* (2013.01); *A61F 2002/3401* (2013.01); *A61F 2002/3613* (2013.01); *A61F 2002/3621* (2013.01); *A61F 2002/3647* (2013.01); *A61F 2002/365* (2013.01); *A61F 2002/368* (2013.01); *A61F 2002/3694* (2013.01); *A61M 2205/04* (2013.01)

(58) Field of Classification Search
 CPC .... A61F 2/32; A61F 2250/0068; A61B 17/56; A61B 2017/561; A61M 5/14276; A61M 31/002
 See application file for complete search history.

(56) References Cited

U.S. PATENT DOCUMENTS

| | | |
|---|---|---|
| 4,399,814 A | 8/1983 | Pratt, Jr. et al. |
| 4,488,549 A | 12/1984 | Lee et al. |
| 4,653,487 A | 3/1987 | Maale |
| 4,711,233 A | 12/1987 | Brown |
| 4,888,024 A | 12/1989 | Powlan |
| 4,892,550 A | 1/1990 | Huebsch |
| 5,116,377 A | 5/1992 | Skripitz et al. |
| 5,133,767 A | 7/1992 | Frey et al. |
| 5,133,771 A | 7/1992 | Duncan et al. |
| 5,133,772 A | 7/1992 | Hack et al. |
| 5,156,606 A | 10/1992 | Chin |
| 5,290,291 A | 3/1994 | Linden |
| 5,340,362 A | 8/1994 | Carbone |
| 5,370,698 A | 12/1994 | Heimke et al. |
| 5,376,123 A | 12/1994 | Klaue et al. |
| 5,433,718 A | 7/1995 | Brinker |
| 5,501,687 A | 3/1996 | Willert et al. |
| 5,514,137 A | 5/1996 | Coutts |
| 5,549,702 A | 8/1996 | Ries et al. |
| 5,554,111 A | 9/1996 | Morrey et al. |
| 5,562,736 A | 10/1996 | Ray et al. |
| 5,571,204 A | 11/1996 | Nies |
| 5,618,286 A | 4/1997 | Brinker |
| 5,681,289 A | 10/1997 | Wilcox et al. |
| 5,683,472 A | 11/1997 | O'Neil et al. |
| 5,693,099 A | 12/1997 | Harle |
| 5,702,446 A | 12/1997 | Schenck et al. |
| 5,725,596 A | 3/1998 | Burke |
| 5,741,265 A | 4/1998 | Chan |
| 5,755,811 A | 5/1998 | Tanamal et al. |
| 5,827,289 A | 10/1998 | Reiley et al. |
| 5,871,484 A | 2/1999 | Spievack et al. |
| 5,916,269 A | 6/1999 | Serbousek et al. |
| 5,954,771 A | 9/1999 | Richelsoph et al. |
| 5,980,573 A | 11/1999 | Shaffner |
| 6,066,154 A | 5/2000 | Reiley et al. |
| 6,106,495 A | 8/2000 | Scott |
| 6,113,639 A | 9/2000 | Ray et al. |
| 6,132,674 A | 10/2000 | Compton et al. |
| 6,155,812 A | 12/2000 | Smith et al. |
| 6,217,619 B1 | 4/2001 | Keller |
| 6,235,043 B1 | 5/2001 | Reiley et al. |
| 6,248,110 B1 | 6/2001 | Reiley et al. |
| 6,336,941 B1 | 1/2002 | Subba Rao et al. |
| 6,361,731 B1 | 3/2002 | Smith et al. |
| 6,361,780 B1 | 3/2002 | Ley et al. |
| 6,423,083 B2 | 7/2002 | Reiley et al. |
| 6,447,514 B1 | 9/2002 | Stalcup et al. |
| 6,544,472 B1 | 4/2003 | Compton et al. |
| 6,589,281 B2 | 7/2003 | Hyde, Jr. |
| 6,679,890 B2 | 1/2004 | Margulies et al. |
| 6,692,529 B2 | 2/2004 | Shah |
| 6,740,090 B1 | 5/2004 | Cragg et al. |
| 6,740,120 B1 | 5/2004 | Grimes |
| 6,783,515 B1 | 8/2004 | Miller et al. |
| 6,899,716 B2 | 5/2005 | Cragg |
| 6,921,403 B2 | 7/2005 | Cragg et al. |
| 6,942,475 B2 | 9/2005 | Ensign et al. |
| 6,942,702 B2 | 9/2005 | Mitsugi et al. |
| 6,969,404 B2 | 11/2005 | Ferree |
| 6,979,336 B2 | 12/2005 | Durniak |
| 6,981,981 B2 | 1/2006 | Reiley et al. |
| 6,989,033 B1 | 1/2006 | Schmidt |
| 7,048,743 B2 | 5/2006 | Miller et al. |
| 7,112,205 B2 | 9/2006 | Carrison |
| 7,141,053 B2 | 11/2006 | Rosa et al. |
| 7,141,067 B2 | 11/2006 | Jones et al. |
| 7,211,113 B2 | 5/2007 | Zelener et al. |
| 7,217,260 B2 | 5/2007 | Molander et al. |
| 7,250,055 B1 | 7/2007 | Vanderwalle |
| 7,255,713 B2 | 8/2007 | Malek |
| 7,300,282 B2 | 11/2007 | Sapian |
| 7,306,629 B2 | 12/2007 | Saladino et al. |
| 7,427,296 B2 | 9/2008 | Evans |
| 7,429,346 B2 | 9/2008 | Ensign et al. |
| 7,534,240 B1 | 5/2009 | Johnson |
| 7,572,293 B2 | 8/2009 | Rhodes et al. |
| 7,601,157 B2 | 10/2009 | Boyd et al. |
| 7,601,176 B2 | 10/2009 | Soffiati et al. |
| 7,641,698 B1 | 1/2010 | Gibbs et al. |
| 7,771,428 B2 | 8/2010 | Siravo et al. |
| 7,842,095 B2 | 11/2010 | Klein |
| 7,862,619 B2 | 1/2011 | Clark |
| 7,914,585 B2 | 3/2011 | Keller |
| 8,038,682 B2 | 10/2011 | McGill et al. |
| 8,097,039 B2 | 1/2012 | Evans |
| 8,135,466 B2 | 3/2012 | Fuller et al. |
| 8,366,782 B2 | 2/2013 | Wright |
| 8,388,881 B2 | 3/2013 | Giori |
| 8,454,706 B2 | 6/2013 | de Beaubien |
| 8,475,505 B2 | 7/2013 | Nebosky et al. |
| 8,496,711 B2 | 7/2013 | Anapliotis et al. |
| 8,500,819 B2 | 8/2013 | Meridew et al. |
| 8,529,532 B2 | 9/2013 | Pinto et al. |
| 8,579,985 B2 | 11/2013 | Podolsky et al. |
| 8,608,802 B2 | 12/2013 | Bagga et al. |
| 8,652,216 B2 | 2/2014 | Chen et al. |
| 8,673,018 B2 | 3/2014 | Walls |
| 8,685,432 B2 | 4/2014 | Evans et al. |
| 8,721,520 B2 | 5/2014 | Caira et al. |
| 8,900,322 B2 | 12/2014 | de Beaubien |
| 8,900,323 B2 | 12/2014 | de Beaubien |
| 8,974,538 B2 | 3/2015 | Teeny et al. |
| 9,173,742 B2 | 11/2015 | Faccioli et al. |
| 9,198,759 B2 * | 12/2015 | Faccioli ................ A61F 2/3609 |
| RE46,283 E | 1/2017 | de Beaubien |
| 9,707,008 B2 | 7/2017 | Krebs et al. |
| 9,795,486 B2 | 10/2017 | Faccioli et al. |
| RE46,669 E | 1/2018 | de Beaubien |
| 9,925,363 B2 | 3/2018 | Magagnoli |

(56) References Cited

U.S. PATENT DOCUMENTS

| | | | |
|---|---|---|---|
| 10,433,965 | B2 | 10/2019 | de Beaubien et al. |
| RE48,119 | E | 7/2020 | de Beaubien |
| 2001/0051831 | A1 | 12/2001 | Subba Rao et al. |
| 2002/0143402 | A1 | 10/2002 | Steinberg |
| 2002/0169507 | A1 | 11/2002 | Malone |
| 2003/0060891 | A1 | 3/2003 | Shah |
| 2003/0097184 | A1 | 5/2003 | Mitsugi et al. |
| 2003/0187513 | A1 | 10/2003 | Durniak |
| 2004/0036189 | A1 | 2/2004 | Ensign et al. |
| 2004/0111162 | A1 | 6/2004 | Southworth |
| 2004/0193268 | A1 | 9/2004 | Hazebrouck |
| 2004/0193281 | A1 | 9/2004 | Grimes |
| 2004/0225360 | A1 | 11/2004 | Malone |
| 2005/0004680 | A1 | 1/2005 | Saladino et al. |
| 2005/0021084 | A1 | 1/2005 | Lu et al. |
| 2005/0107794 | A1 | 5/2005 | Hazebrouck |
| 2005/0187555 | A1 | 8/2005 | Biedermann et al. |
| 2005/0277936 | A1 | 12/2005 | Siravo et al. |
| 2006/0004431 | A1 | 1/2006 | Fuller et al. |
| 2006/0014120 | A1 | 1/2006 | Sapian |
| 2006/0030945 | A1 | 2/2006 | Wright |
| 2006/0093646 | A1 | 5/2006 | Cima et al. |
| 2006/0121083 | A1 | 6/2006 | Mor |
| 2007/0005142 | A1 | 1/2007 | Rhodes et al. |
| 2007/0016163 | A1 | 1/2007 | Santini et al. |
| 2007/0088442 | A1 | 4/2007 | Cima et al. |
| 2007/0110804 | A1 | 5/2007 | Royer |
| 2007/0123835 | A1 | 5/2007 | Molander et al. |
| 2007/0179609 | A1 | 8/2007 | Goble et al. |
| 2009/0069899 | A1 | 3/2009 | Klein |
| 2009/0130167 | A1 | 5/2009 | Shelton et al. |
| 2010/0042167 | A1 | 2/2010 | Nebosky et al. |
| 2010/0042213 | A1 | 2/2010 | Nebosky et al. |
| 2010/0042214 | A1 | 2/2010 | Nebosky et al. |
| 2010/0042215 | A1 | 2/2010 | Stalcup et al. |
| 2010/0114324 | A1 | 5/2010 | Gibbs et al. |
| 2010/0217401 | A1 | 8/2010 | de Beaubien |
| 2010/0292803 | A1 | 11/2010 | Giori |
| 2011/0015754 | A1 | 1/2011 | Leonard et al. |
| 2011/0208315 | A1 | 8/2011 | Anapliotis et al. |
| 2011/0218644 | A1 | 9/2011 | Meridew et al. |
| 2011/0236501 | A1 | 9/2011 | Guelcher et al. |
| 2012/0109303 | A1 | 5/2012 | Capote |
| 2012/0209382 | A1* | 8/2012 | Forsell ............... A61F 2/34 |
| | | | 623/14.12 |
| 2013/0041472 | A1 | 2/2013 | Rabiner et al. |
| 2013/0158595 | A1 | 6/2013 | Mavani et al. |
| 2013/0209522 | A1 | 8/2013 | Brooks et al. |
| 2013/0211334 | A1 | 8/2013 | de Beaubien |
| 2013/0211369 | A1 | 8/2013 | de Beaubien |
| 2013/0218100 | A1 | 8/2013 | Armbruster et al. |
| 2013/0237908 | A1 | 9/2013 | Clark |
| 2013/0289621 | A1 | 10/2013 | Fulmer et al. |
| 2014/0194810 | A1 | 7/2014 | Barsoum et al. |
| 2014/0194811 | A1 | 7/2014 | Barsoum et al. |
| 2014/0277532 | A1 | 9/2014 | Teeny et al. |
| 2015/0038941 | A1* | 2/2015 | Nebosky ............... A61B 17/866 |
| | | | 604/285 |
| 2016/0199190 | A1 | 7/2016 | Sharifi-Mehr et al. |
| 2020/0330661 | A1 | 10/2020 | Canner et al. |
| 2020/0360578 | A1 | 11/2020 | Loske et al. |

FOREIGN PATENT DOCUMENTS

| | | |
|---|---|---|
| DE | 19722359 A1 | 12/1998 |
| DE | 19722389 A1 | 12/1998 |
| DE | 102010052914 A1 | 5/2012 |
| EP | 0692226 A1 | 1/1996 |
| EP | 2326287 B1 | 5/2016 |
| EP | 2943164 B1 | 3/2017 |
| GB | 2478425 A | 9/2011 |
| IT | VI 20000025 U1 | 10/2001 |
| JP | 2005-028129 A | 2/2005 |
| JP | 2012-500056 A | 1/2012 |
| JP | 2012-501228 A | 1/2012 |
| JP | 2014-176714 A | 9/2014 |
| KR | 101377900 B1 | 3/2014 |
| NZ | 279442 A | 2/1998 |
| WO | WO-03/037166 A2 | 5/2003 |
| WO | WO-2005/122932 A2 | 12/2005 |
| WO | WO-2007/047420 A2 | 4/2007 |
| WO | WO-2010/019781 A1 | 2/2010 |
| WO | WO-2010/080667 A1 | 7/2010 |
| WO | WO-2012/030331 A1 | 3/2012 |
| WO | WO-2013/041906 A1 | 3/2013 |
| WO | WO-2013/059609 A1 | 4/2013 |
| WO | WO-2014/110313 A1 | 7/2014 |
| WO | WO-2016/205077 A1 | 12/2016 |

OTHER PUBLICATIONS

Finsterbusch, A. et al. (1970). "Bone and joint perfusion with antibiotics in the treatment of experimental staphylococcal infection in rabbits." J Bone Joint Surg Am, 52(7): p. 1424-1432.

Florschutz, A.V. et al. (2015). "Infection after primary anatomic versus primary reverse total shoulder arthroplasty." J Shoulder Elbow Surg, 24(8): p. 1296-1301.

Lescun, T.B. et al. (2000). "Continuous infusion of gentamicin into the tarsocrural joint of horses." Am J Vet Res, 61(4): p. 407-412.

Lescun, T.B. et al. (2006). "Treatment with continuous intrasynovial antimicrobial infusion for septic synovitis in horses: 31 cases (2000-2003)." J Am Vet Med Assoc, 228(12): p. 1922-1929.

Lloyd, K.C. et al. (1988). "Effect of gentamicin sulfate and sodium bicarbonate on the synovium of clinically normal equine antebrachiocarpal joints." Am J Vet Res, 49(5): p. 650-657.

Lloyd, K.C., et al. (1988). "Plasma and synovial fluid concentrations of gentamicin in horses after intra-articular administration of buffered and unbuffered gentamicin." Am J Vet Res, 49(5): p. 644-649.

Schneider, R.K. et al. (1992). "Open drainage, intra-articular and systemic antibiotics in the treatment of septic arthritis/tenosynovitis in horses." Equine Vet J, 24(6): p. 443-9. [Abstract: 2 pages].

Shelly, M. et al. (2011). "Renal Toxicity Related to Antibiotic-Containing Orthopedic Cement." Pharmacokinetics and Adverse Drug Reactions. 2 pages.

Thabe, H. et al. (2007). "Two-stage Reimplantation with An Application Spacer and Combined with Delivery of Antibiotics in the Management of Prosthetic Joint Infection" Oper. Orthop Traumatol, 1:78-100. [German language and English language].

Ure, K.J. et al. (1998). "Direct-exchange arthroplasty for the treatment of infection after total hip replacement. An average ten-year follow-up." J Bone Joint Surg Am, 80(7): p. 961-968.

Whitehair, K.J., et al. (1992). "Regional Limb Perfusion for Antibiotic Treatment of Experimentally Induced Septic Arthritis." Vet Surg, 21(5): p. 367-73. [Abstract: 2 pages].

Whiteside, L. et al. (2011). "Methicillin-resistant *Staphylococcus aureus* in TKA Treated With Revision and Direct Intraarticular Antibiotic Infusion." Clin Orthop Relat Res, 469:26-33.

Wroblewski, B.M. (1986). "One-stage Revision of Infected Cemented Total Hip Arthroplasty." Clin Orthop Relat Res, (211): p. 103-107.

Zavala, J.A. et al. (2012). "Management of deep infection after reverse total shoulder arthroplasty: a case series." J Shoulder Elbow Surg, 21(10): p. 1310-1315.

* cited by examiner

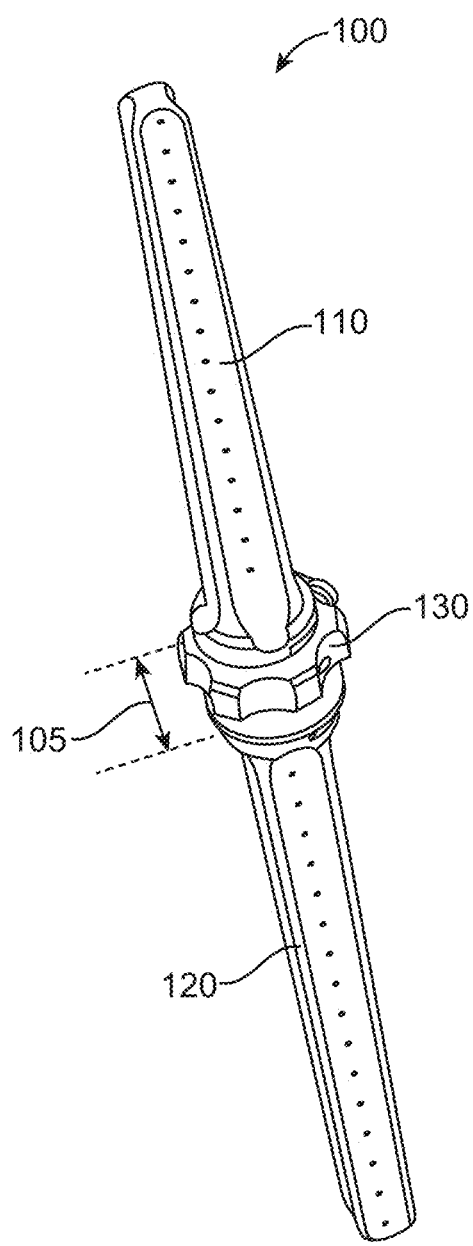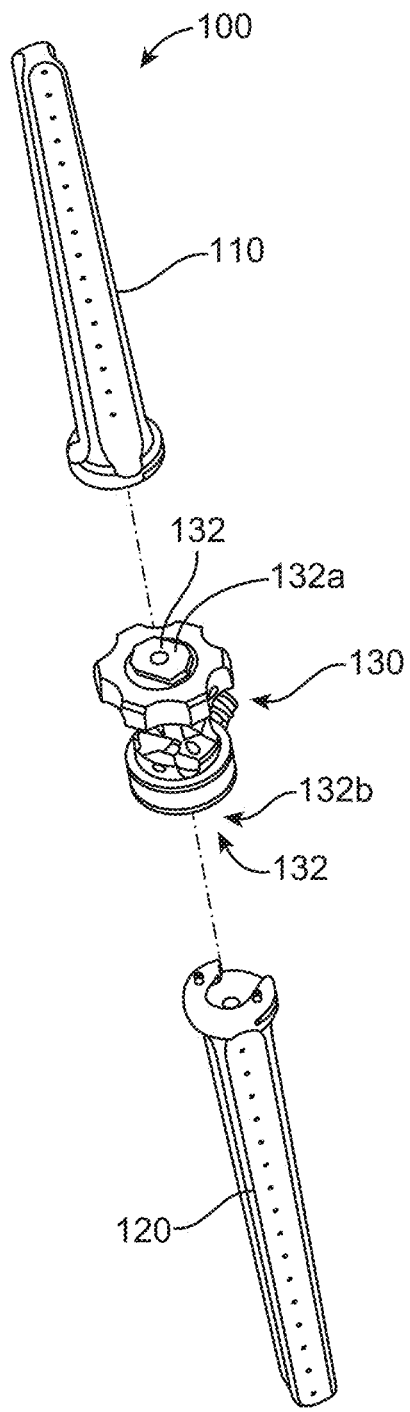
FIG. 1A                    FIG. 1B

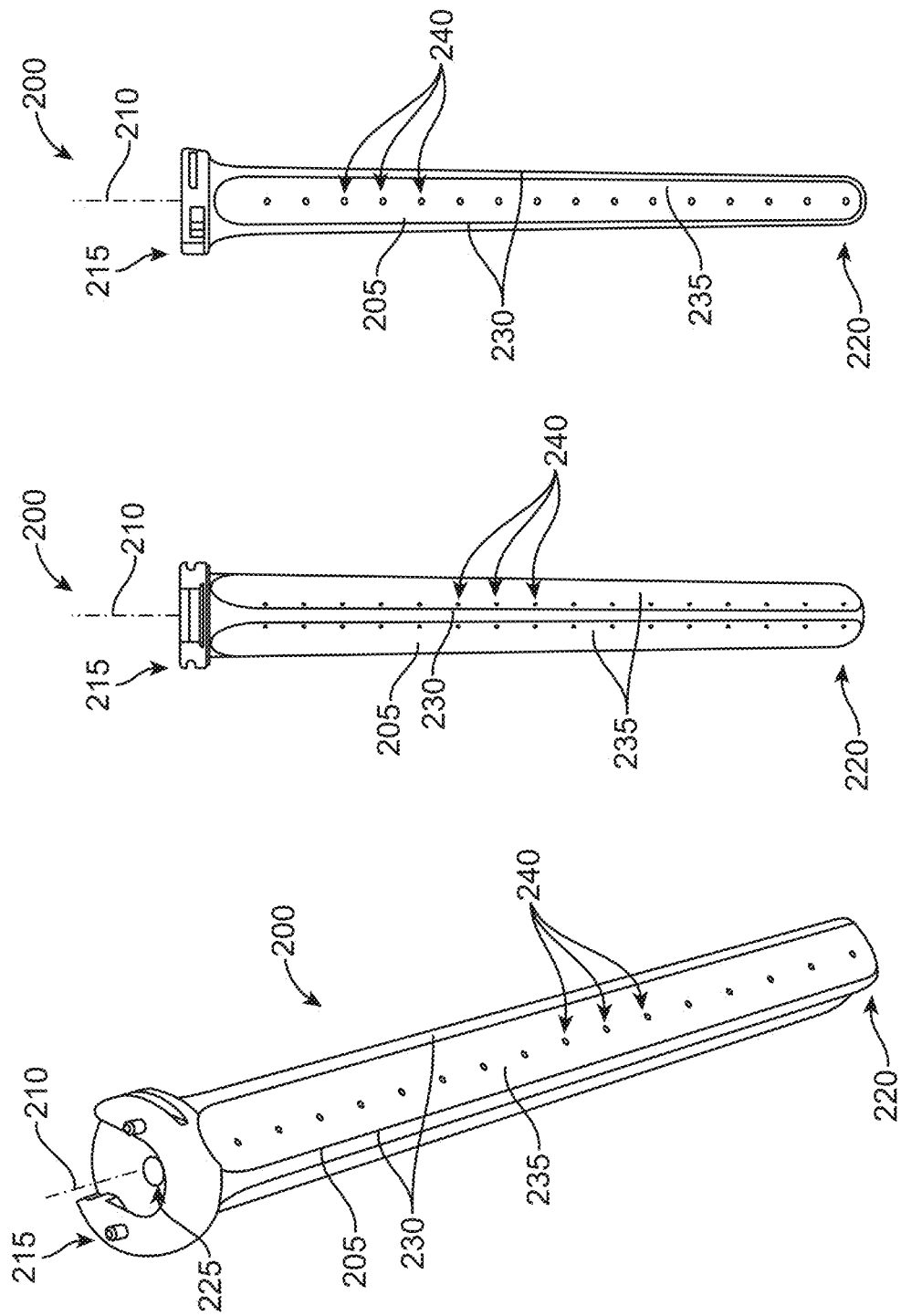

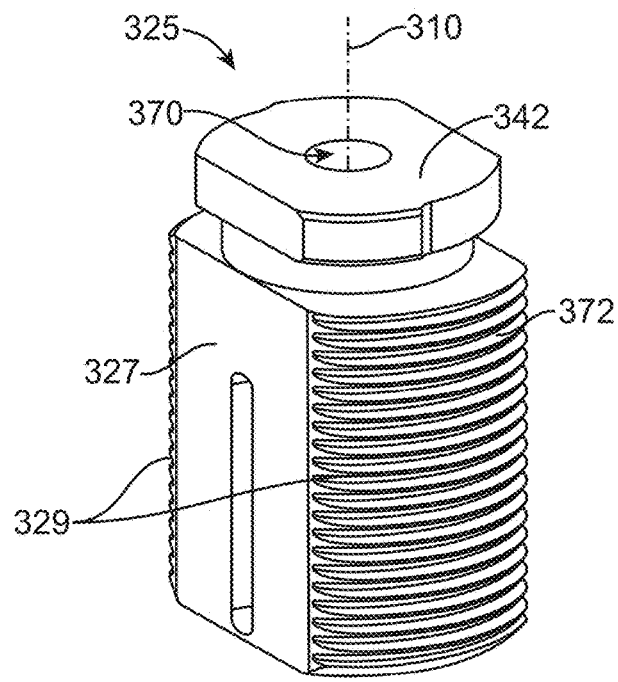
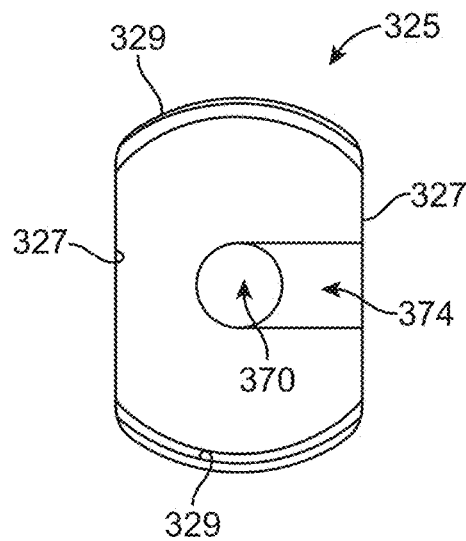
FIG. 8A          FIG. 8B
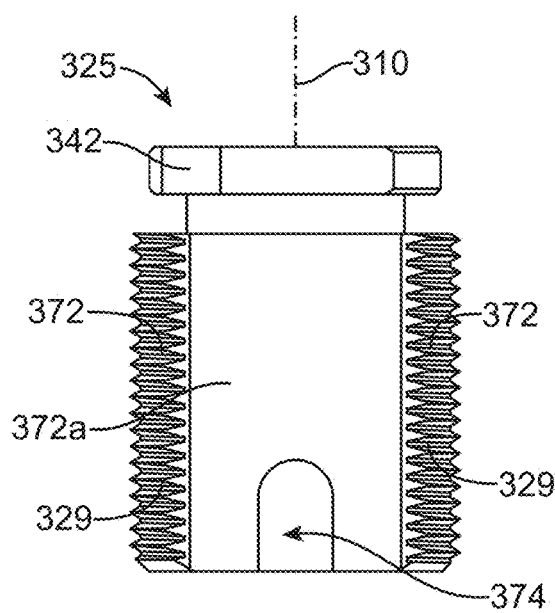
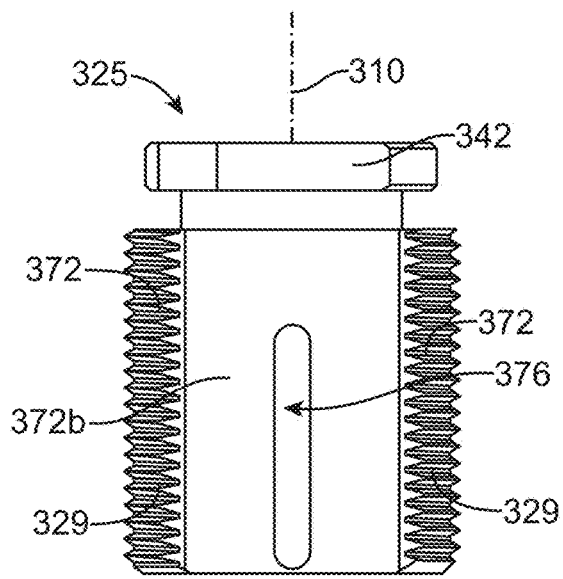
FIG. 8C          FIG. 8D

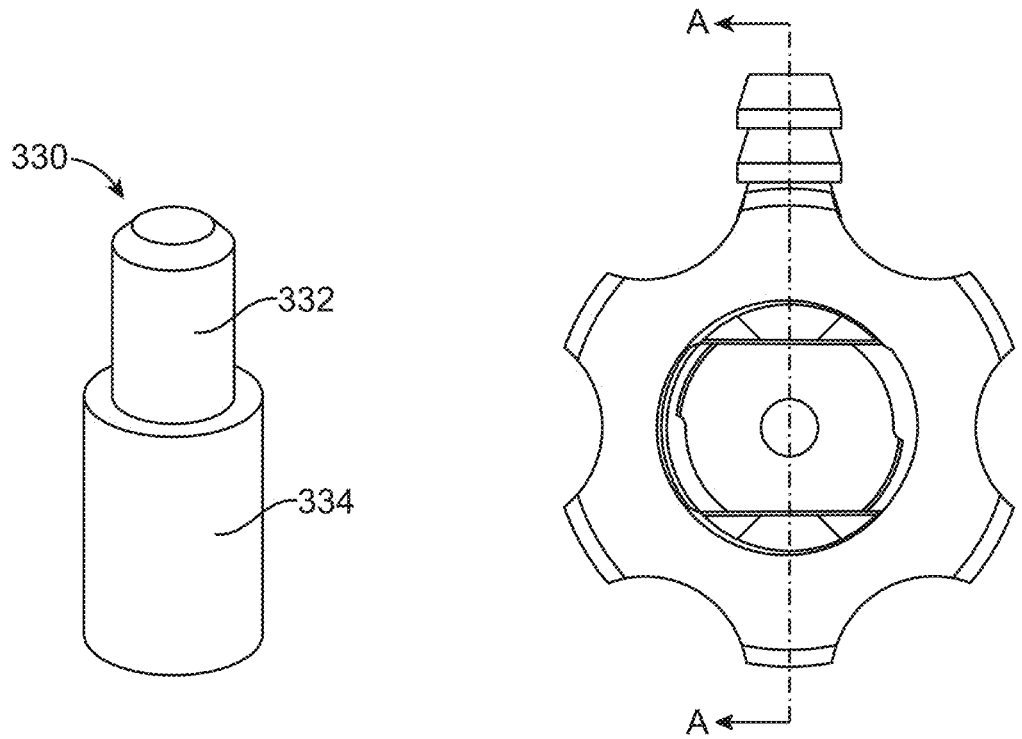
FIG. 9
FIG. 10A
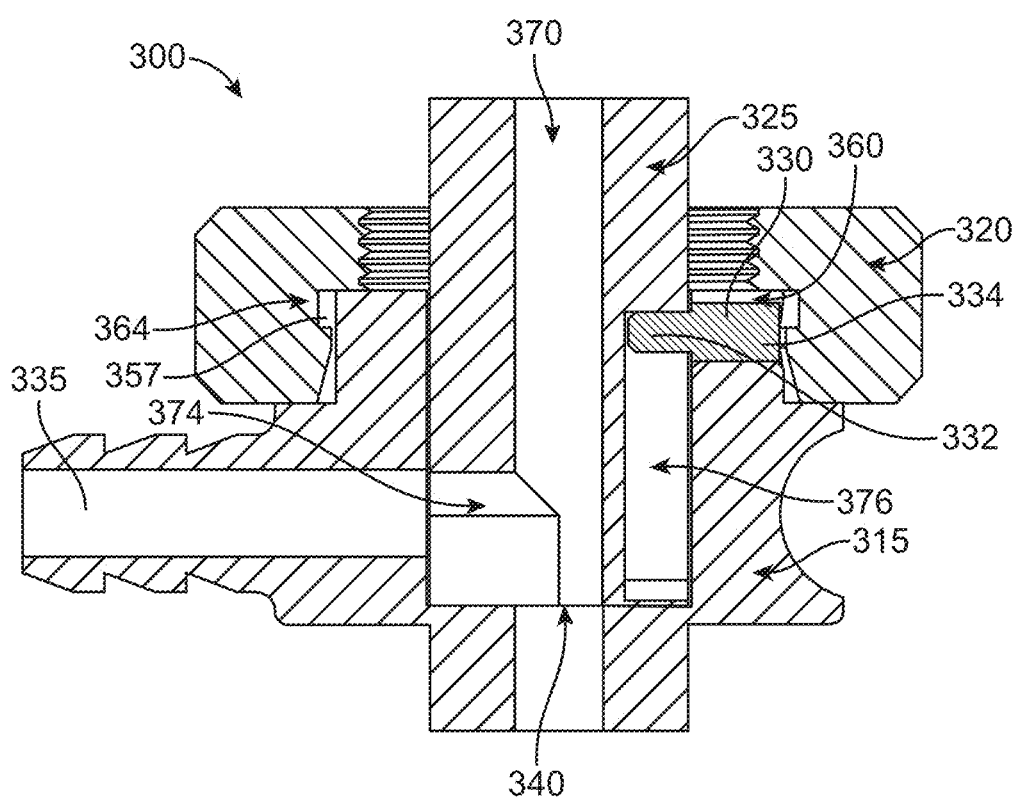
FIG. 10B

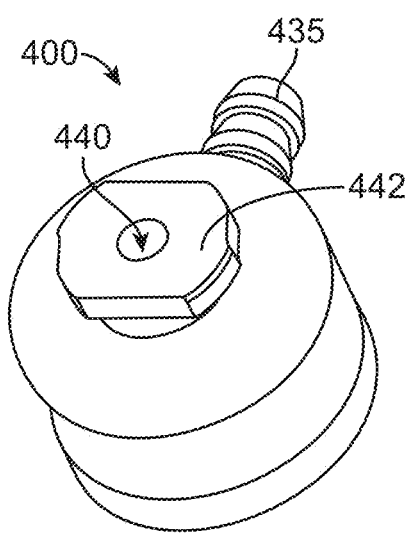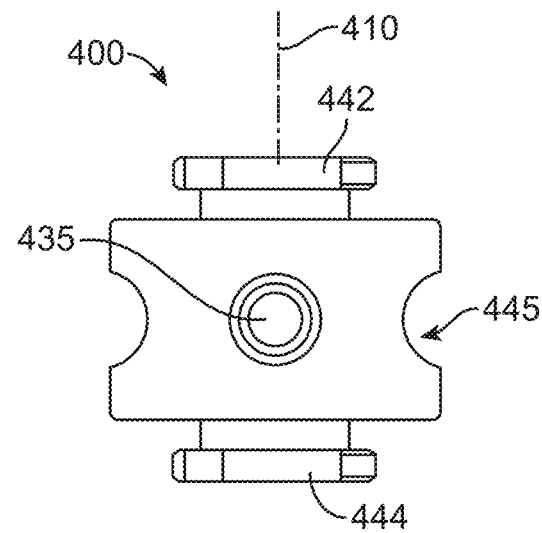
FIG. 11A  FIG. 11B
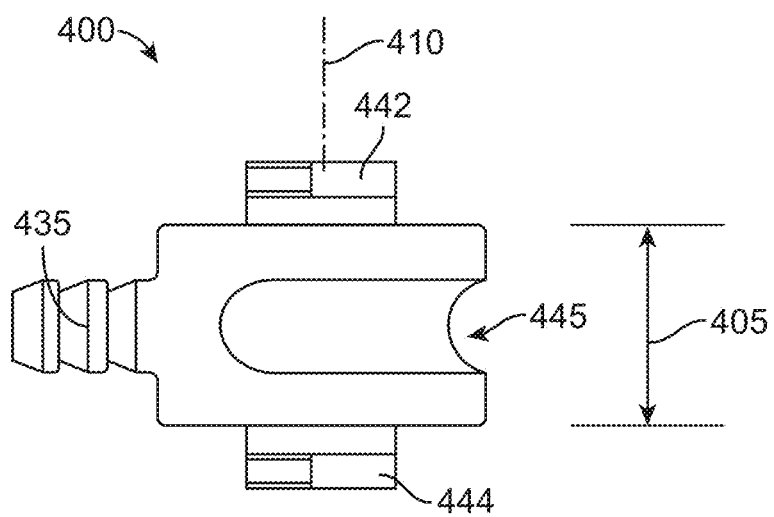
FIG. 11C

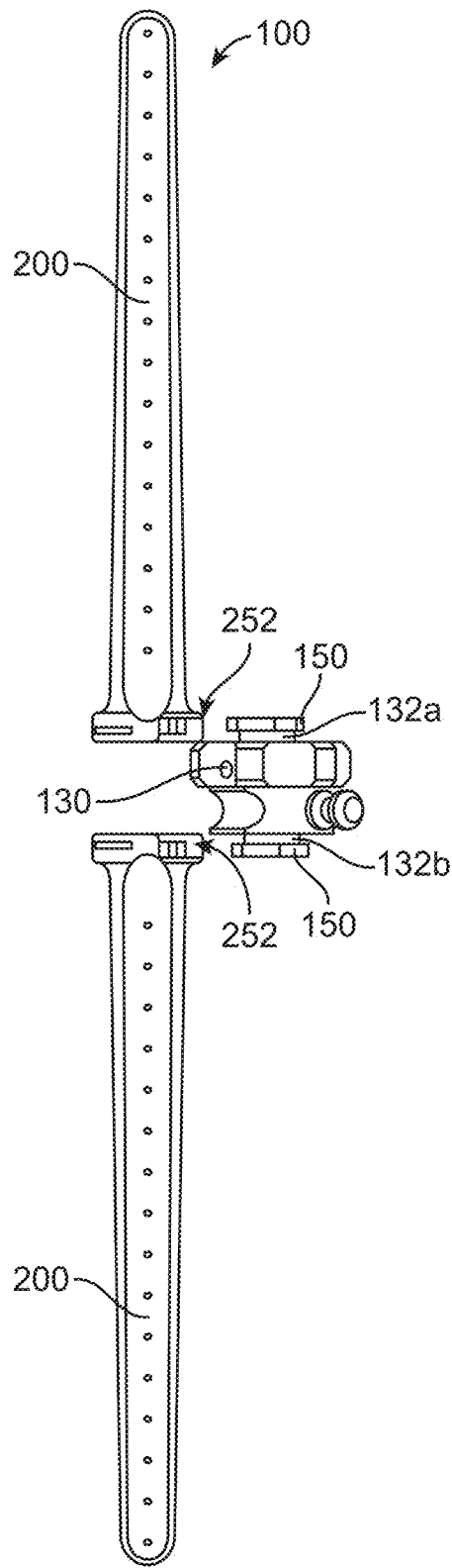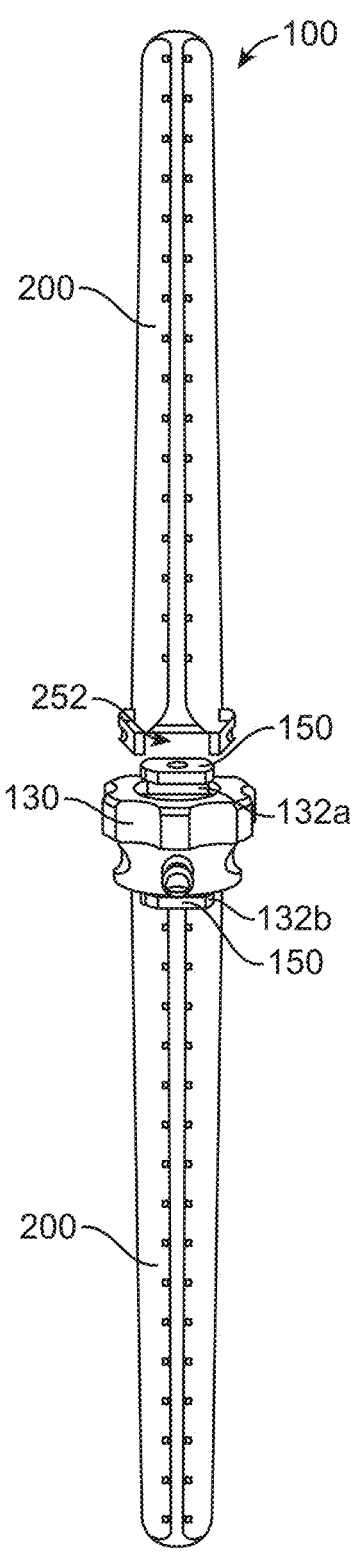
FIG. 12C
FIG. 12D

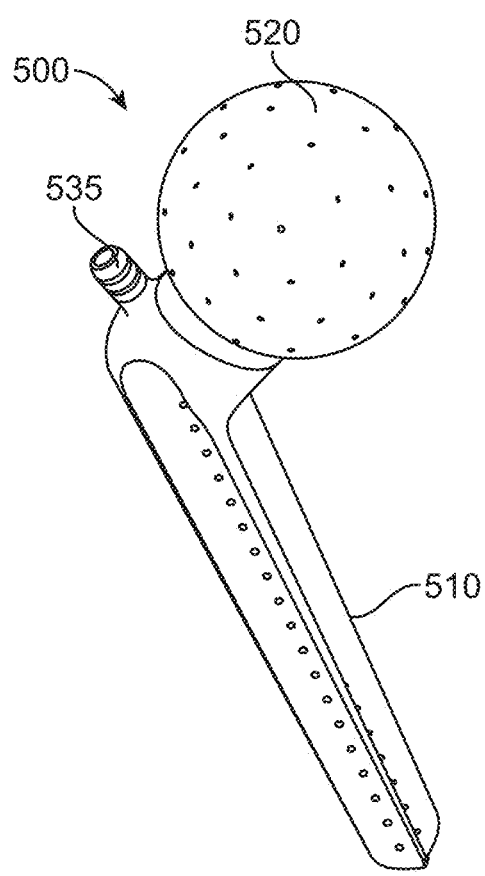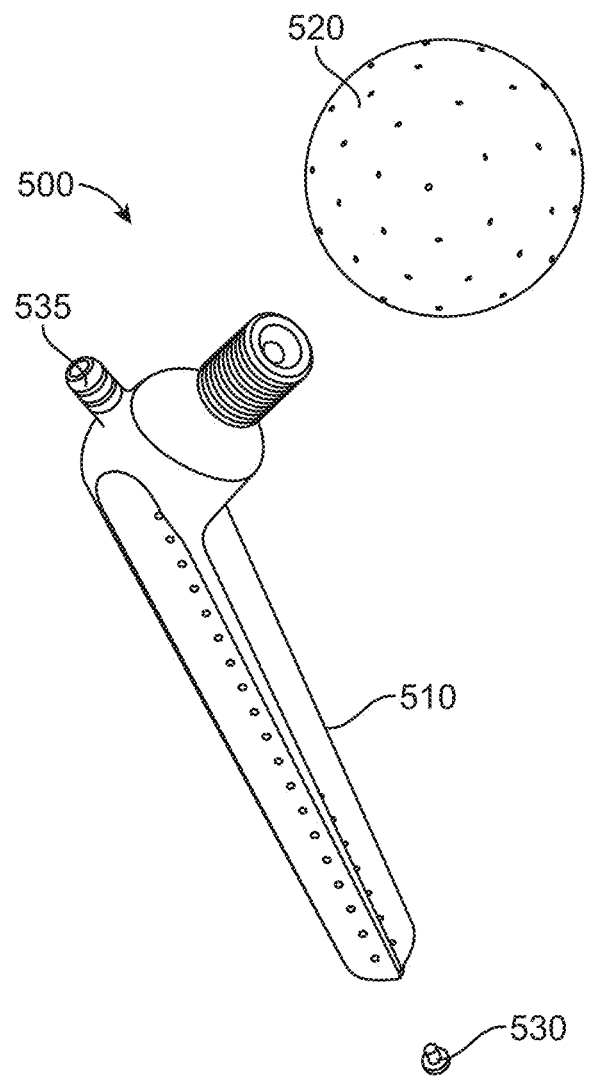
FIG. 17A
FIG. 17B

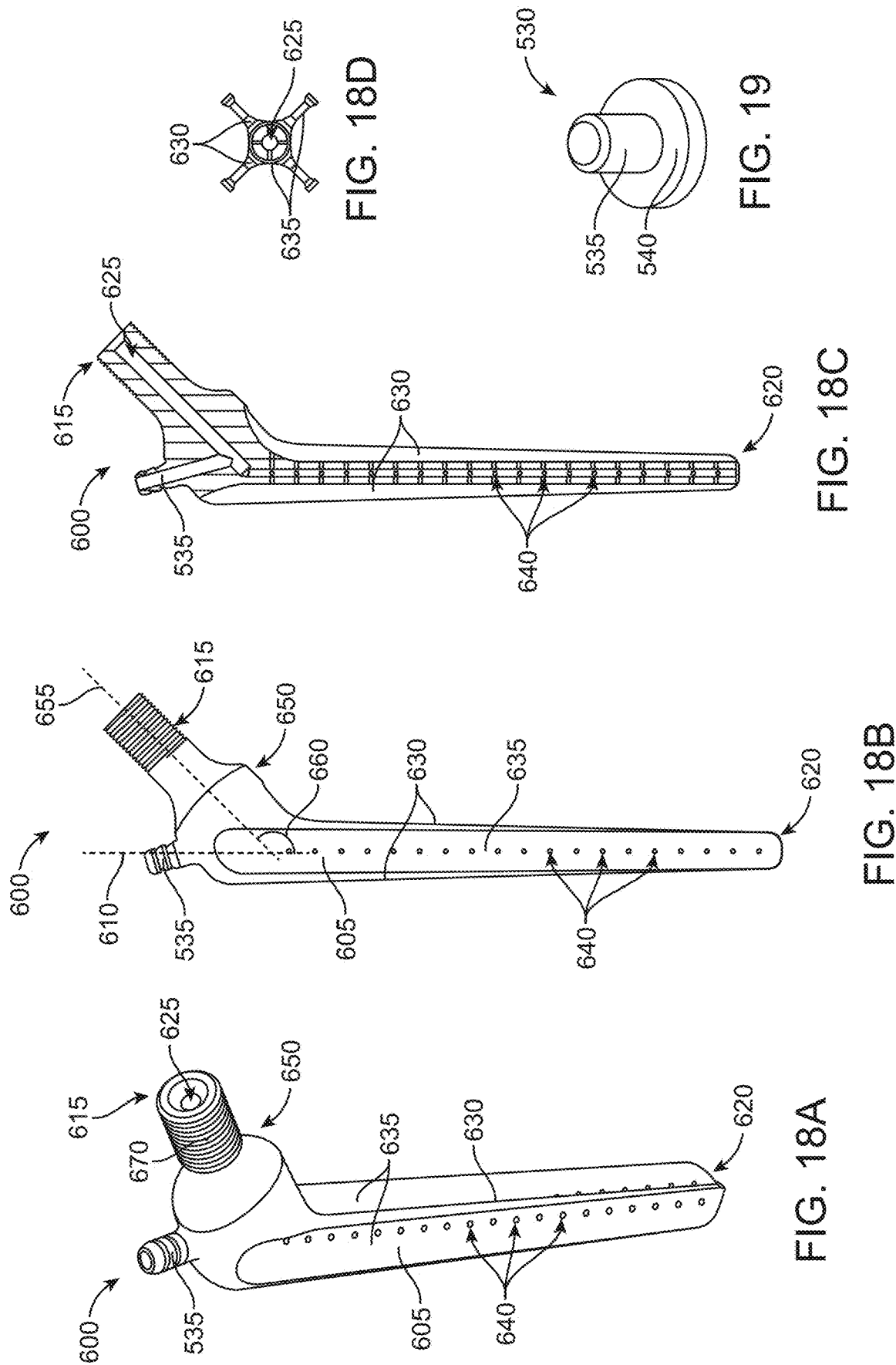

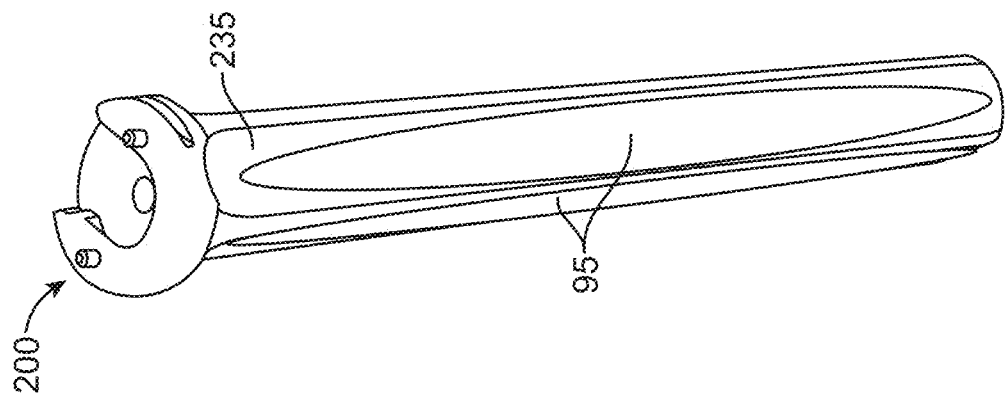
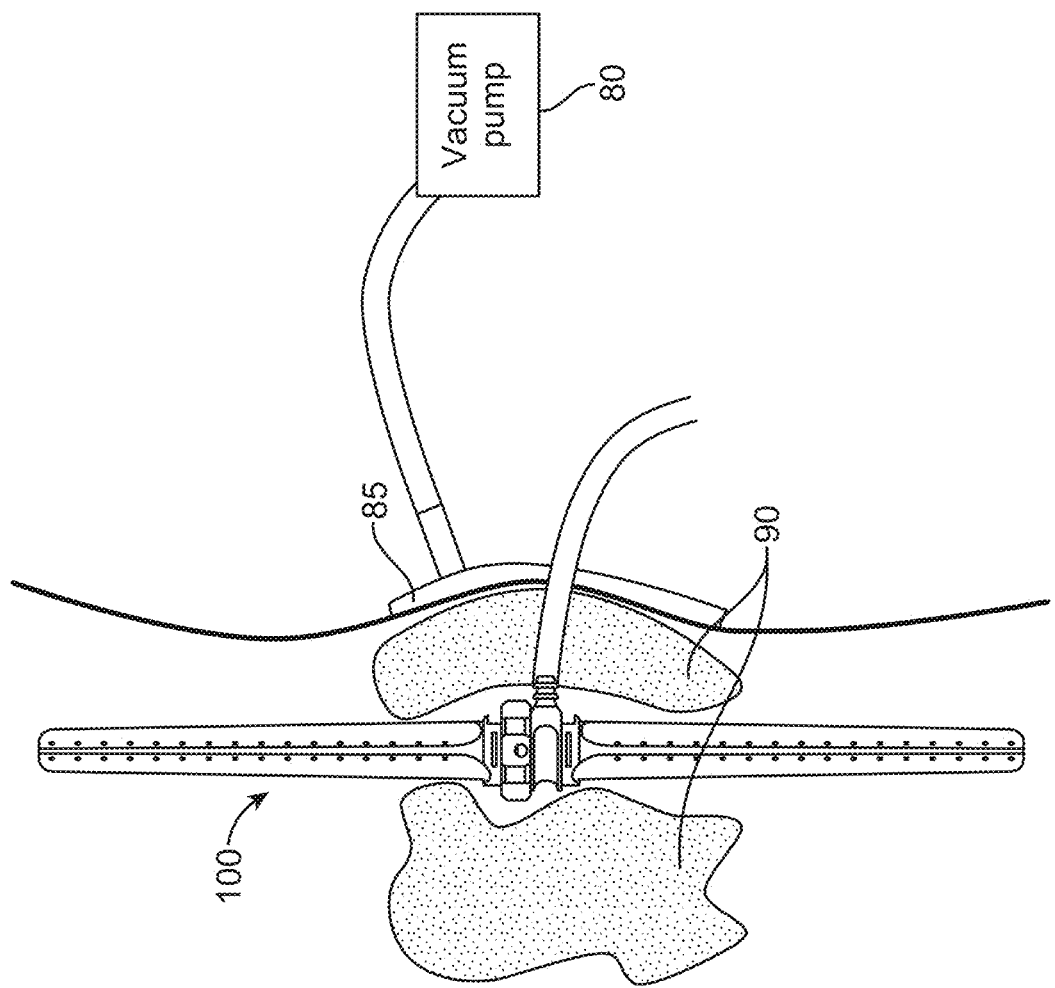
FIG. 28B
FIG. 28A

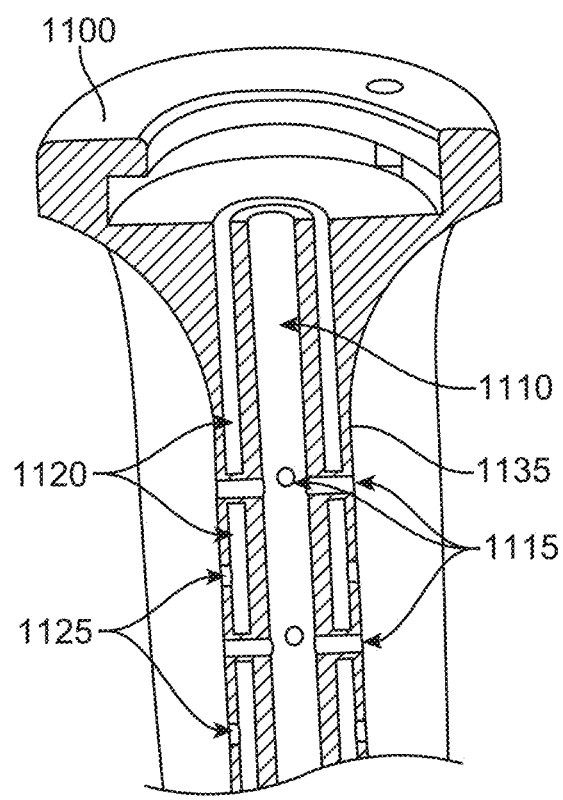 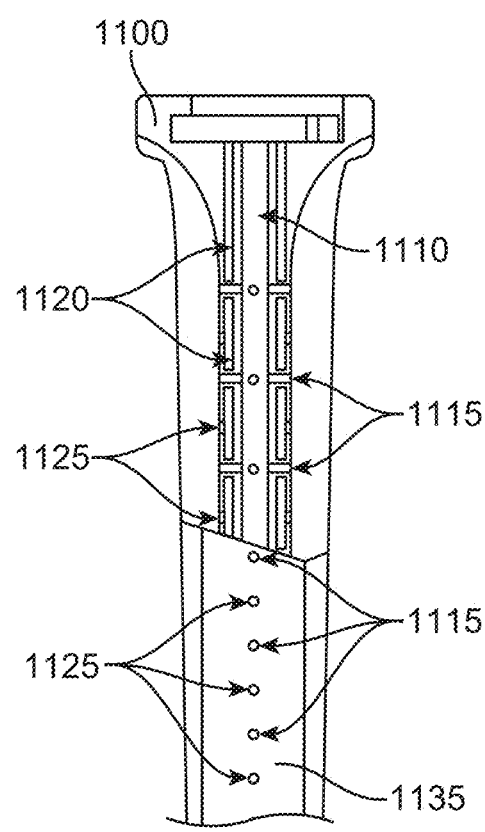
FIG. 32A
FIG. 32B

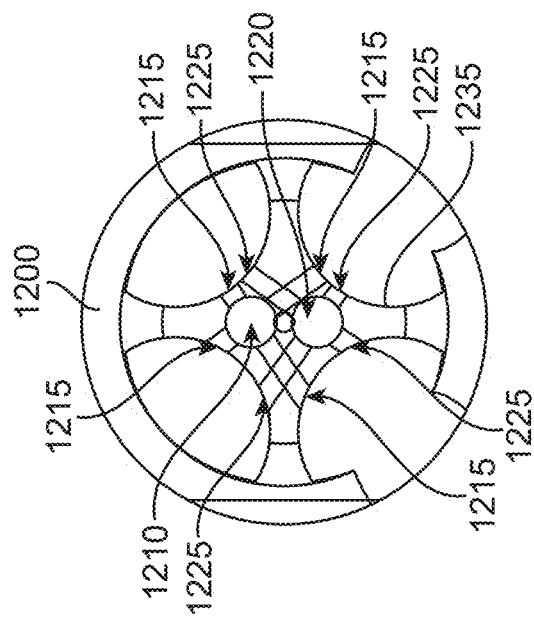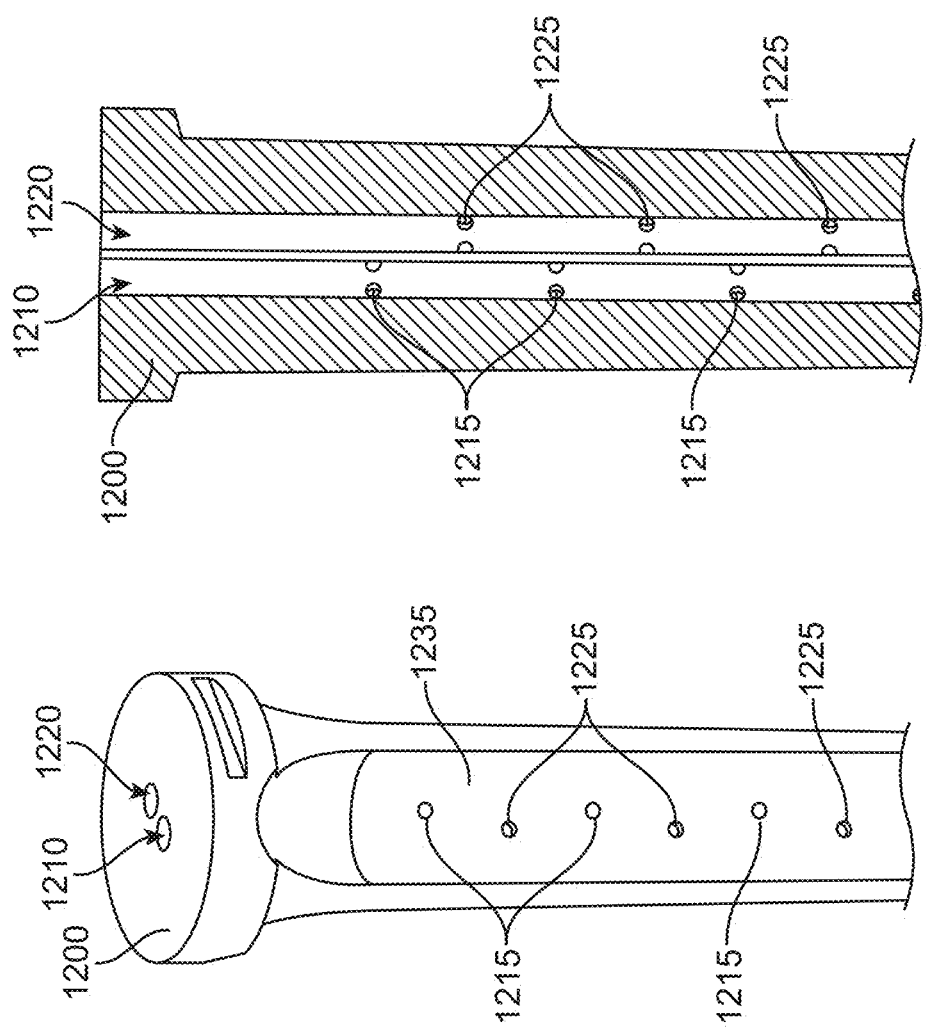
FIG. 33C
FIG. 33B
FIG. 33A

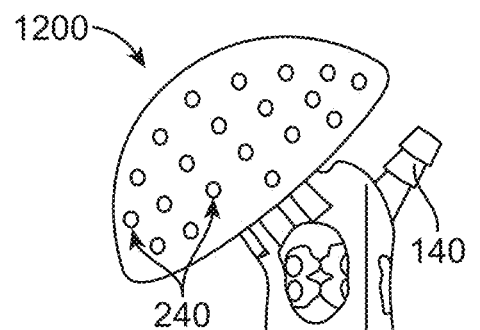
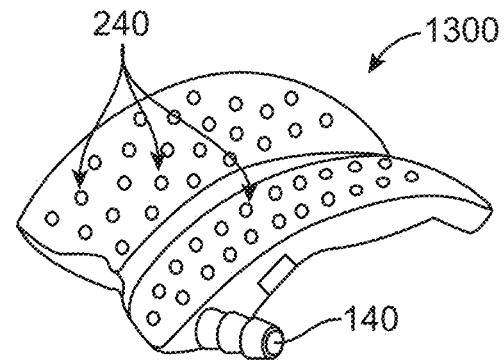
FIG. 35
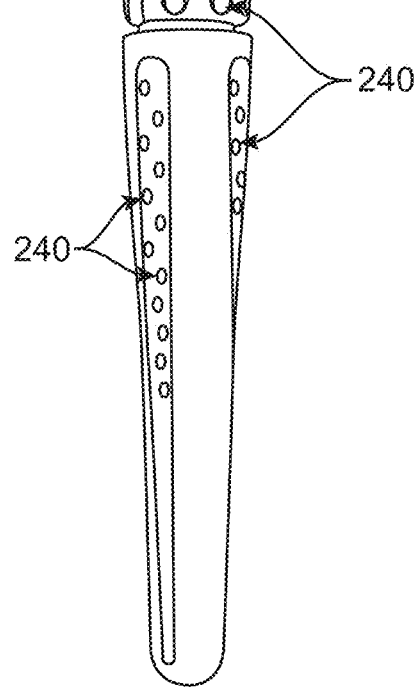
FIG. 34
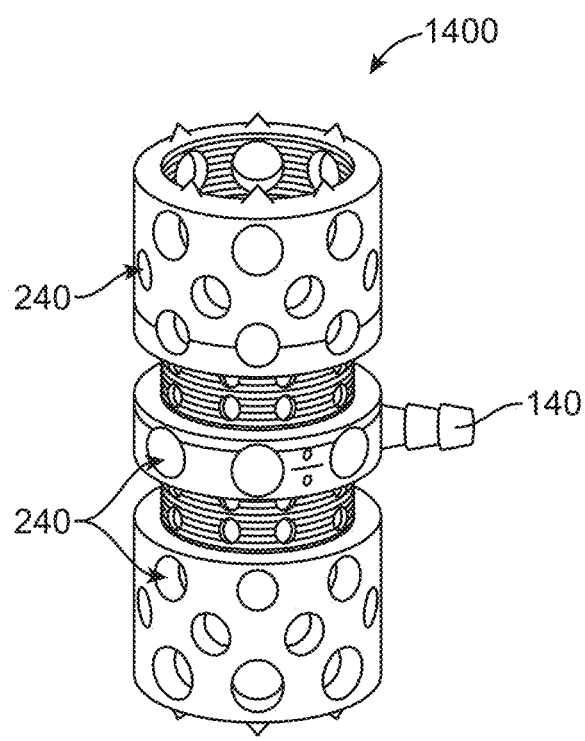
FIG. 36

TOTAL JOINT REPLACEMENT INFECTION CONTROL DEVICES AND METHODS

CROSS-REFERENCE

This application is a continuation of U.S. Non-Provisional application Ser. No. 16/513,599, filed Jul. 16, 2019, which is a divisional application of U.S. Non-Provisional application Ser. No. 14/841,529, filed Aug. 31, 2015, now U.S. Pat. No. 10,433,965, which claims the benefit of U.S. Provisional Application No. 62/180,986, filed on Jun. 17, 2015, entitled "Total Joint Replacement Infection Control Devices and Methods", the entire contents of which are incorporated herein by reference.

BACKGROUND OF THE INVENTION

1. Field of the Invention

A total joint replacement (TJR) is a medical procedure that involves the repair and replacement of joints, such as hips and knees. In these surgical procedures, the bones at the hip or knee joints receive orthopedic implants that mimic the structure of the joint that is replaced.

In some cases, infection occurs and this is can be a devastating complication of TJR surgeries. Unless an infection is properly diagnosed within the first two to four weeks following the original surgery (which is uncommon), the infected implant must be removed in combination with an extensive debridement of the surrounding joint tissue and bone.

The current standard of care for treatment of an infected TJR in the United States typically involves a two-stage re-implantation process. In the first stage of this process, the infected components are surgically exposed by incision. Scar tissue is then de-bulked and other soft tissue may be released, and sometimes an osteotomy is performed. This stage also includes the removal of all prosthetic components and foreign material including, for example, acrylic bone cement. After extensive joint debridement of infected soft tissue and bone, a spacer block consisting of heavily dosed antibiotic bone cement is placed temporarily into the joint space. The purpose of the antibiotic bone cement is to sterilize the joint environment and to serve as an antibiotic delivery system. Additionally, the bone cement acts as a spacer to preserve joint space and maintains ligament length. However, the antibiotic released by the bone cement is uncontrolled and is quite costly to use. In addition, more operating room time is necessary to prepare this spacer material. This increases the cost of the operation Following the removal of the infected implant and the insertion of the antibiotic bone cement spacer, the patient must generally wait between six and twelve weeks before the second stage of the procedure can be performed. This period of time is necessary so that medical professionals can be confident that the infection has been successfully eradicated. Only after the infectious condition has been eliminated, may the second stage proceed. During the second stage, the new prosthesis is re-implanted.

In other countries, such as throughout Europe, a one-stage re-implantation process has been popular. This involves the removal of the infected implant, as noted above, followed by aggressive debridement and then immediate re-implantation of a new implant. The success rate for this technique has typically been lower than the two-stage procedure. The one-state implantation process is generally reserved for patients who are considered to be too feeble or sick to undergo the traditional two-stage re-implantation process.

In certain situations, both one- and two-stage procedures can have disadvantages. For example, and as noted above, the two-stage re-implantation process requires six to twelve weeks between operations. This is a very difficult time for the patient as they do not have a functional joint in place and it is typically very painful to mobilize or ambulate with an antibiotic spacer. Articulating spacers are somewhat better than static spacers, but are also more expensive as well as more difficult and time-consuming to place during the original stage one procedure. From a health care standpoint, the two-stage procedure also requires two separate hospitalizations. Finally, from a surgeon's standpoint, a significant amount of scar tissue develops during the time span between the two procedures. This makes for a very difficult and time-consuming second stage operation. In addition, the two-stage re-implantation process involves not one, but two, very difficult and costly surgical procedures.

On the other hand, a one-stage re-implantation surgical protocol requires absolute identification of the infecting organism in order to proceed. Unfortunately, it is very difficult to achieve this absolute identification in the current health care system. In addition, a one-stage re-implantation protocol requires the use of fully-cemented components. Fully-cemented components are typically not favored by U.S. surgeons for revision surgery because they require a high amount of antibiotic which may structurally weaken the cement.

Moreover, and in both one-stage and two-stage re-implantation surgical protocols, the release of the antibiotic from the bone cement is completely uncontrolled. This is a significant disadvantage of both protocols and essentially acts to lengthen the time between the first and the second surgical procedures in the two-stage re-implantation process.

Thus, there remains a need for a device that may be employed during re-implantation surgical procedures that may be used to deliver antibiotic or other therapeutic agents in a controlled and titratable manner directly into the synovial joint cavity and adjoining medullary canals as a means of eliminating the infection following the removal of a previous orthopedic implant. In addition, there remains a need for such a device that can provide stability and maintain the physical dimensions of joint space and normal soft tissue envelope in any joint undergoing the re-implantation of an orthopedic implant. In addition, there remains a need for such a device that may be easily employed, facilitates the reduction in the time needed to conduct the stage one re-implantation surgery and that reduces the overall time between the first and second stages of a two-stage re-implantation surgical protocol. At least some of these will be addressed by the devices and methods described herein.

2. Description of the Background Art

Other patents which disclose devices and methods for delivery of an antibiotic to an intramedullary canal include: U.S. Pat. Nos. 8,900,323; 8,900,322; and 8,454,706.

SUMMARY OF THE INVENTION

The present invention generally relates to medical systems, devices and methods, and more particularly relates to orthopedic devices used to deliver a therapeutic agent to a joint or intramedullary canal in a bone.

In one aspect of the present invention, a therapeutic agent delivery system comprises a first intramedullary stem configured to be disposed in a first medullary canal of a first bone, a second intramedullary stem configured to be disposed in a second medullary canal of a second bone, and a coupling member coupled to the first intramedullary stem and the second intramedullary stem. Each of the first intramedullary stem and the second intramedullary stem comprises an elongate body having a longitudinal axis, a first end, a second end opposite the first end, and a channel extending between the first end and the second end. Each of the first intramedullary stem and the second intramedullary stem further comprises a plurality of protrusions extending radially outward from the elongate body, wherein adjacent protrusions define or more fluted regions therebetween. The plurality of protrusions are configured to engage the first medullary canal in a stable fashion, and one or more outlet holes are disposed in the one or more fluted regions, wherein the one or more outlet holes are in fluid communication with the channel. The coupling member may be coupled to the first end of the first intramedullary stem and the first end of the second intramedullary stem, wherein the coupling member holds the first and second intramedullary stems together and at a fixed distance. The coupling member may further comprise an inlet in fluid communication with the channels in the first and second intramedullary stems.

In some embodiments, the coupling member may comprise an adjustable height manifold configured to increase or decrease a distance between the first ends of the two intramedullary stems when the adjustable height manifold is actuated. The adjustable height manifold may comprise a housing with a central housing channel disposed therethrough, a rotating nut coupled to the housing, and an adjustable connector disposed in the housing channel. The adjustable connector may have an adjustable connector channel disposed therein. The inlet coupled to the housing may be fluidly connected to the adjustable connector channel, and the adjustable connector channel may be fluidly coupled with the channel in the first stem or the second stem. Rotation of the nut can extend or retract the adjustable connector relative to the housing. The rotating nut may be threadably engaged with the adjustable connector, and the adjustable connector may be slidably disposed in the housing channel, where rotation of the rotating nut moves the adjustable connector up or down in the housing channel without rotation of the adjustable connector.

In some embodiments, the coupling member may comprise a wedge element, wherein disposition of the wedge element between the first end of the first intramedullary stem and the first end of the second medullary stem adjusts a distance between the first ends of the two intramedullary stems.

The therapeutic agent delivery system may further comprise a source of the therapeutic agent for delivery to the medullary canals from the one or more outlet holes in the one or more fluted regions of the first and second stems. The therapeutic agent may be an antibiotic, wherein the antibiotic may comprise vancomycin, tobramycin, or a combination thereof.

In some embodiments, the first medullary canal may be in a femur and the first stem may be configured to be disposed therein. The second medullary canal may be in a tibia and the second stem may be configured to be disposed therein.

In some embodiments, the coupling member may be releasably coupled to the first and second intramedullary stems.

In some embodiments, the first stem may be identical to the second stem.

In some embodiments, the first stem or the second stem may comprise four fins equally spaced around the elongate body and extending along the longitudinal axis thereof. The first stem or the second stem may further comprise a plurality of outlet holes extending axially along a line substantially parallel to the longitudinal axis thereof.

In some embodiments, the coupling member may comprise a flanged region, wherein the first end of the first or second stem comprises a recessed region for receiving the flanged region, and wherein rotation of the flanged region relative to the recessed region can releasably lock the first end with the coupling member. One or more pins may be disposed in the first end of the first or second stem, and the one or more pins may protrude therefrom thereby engaging the flanged region and preventing further rotation of the first or second stem relative to the coupling member. In some embodiments, the coupling member may comprise a snap fit section or a dovetailed section for engaging a corresponding dovetailed section or a corresponding snap fit section on the first stem or the second stem.

In some embodiments, the channel may extend from the first end to the second end of the first or second stem, and the channel may extend through both the first end and the second end. The system may further comprise a plug disposed in the channel at the second end of the first stem or the second stem. In some embodiments, the channel may be a blind channel in the first stem or the second stem, the blind channel having a closed second end.

In some embodiments, the elongate body of the first stem or the second stem may be tapered.

In some embodiments, the coupling member may comprise a housing, a first stem connector configured to engage the first end of the first intramedullary stem, and a second stem connector configured to engage the first end of the second intramedullary stem. The first and second stem connectors may be disposed on opposite sides of the housing. The first stem connector may have an orientation relative to the second stem connector, wherein the orientation may remain the same during actuation of the adjustable height manifold.

In some embodiments, the coupling member may comprise a housing, wherein a concave groove is disposed circumferentially around at least a portion of the housing. The concave groove may be sized to receive a tubing.

The therapeutic agent delivery system may further comprise a cover disposed over the first stem or the second stem, or a sponge disposed in at least some of the one or more fluted regions of the first stem or the second stem. The cover or the sponge can be configured to facilitate even distribution of the therapeutic agent therefrom to the first or the second intramedullary canal.

The therapeutic agent delivery system may further comprise a pump configured to pump the therapeutic agent into the channel of the first or the second stem.

The therapeutic agent delivery system may further comprise a vacuum pump, the vacuum pump configured to remove unwanted fluids from the first or the second medullary canal via the one or more outlet holes or the channel in the first stem or the second stem.

In some embodiments, the plurality of protrusions in the first stem or the second stem may be spirally disposed therearound, or the one or more fluted regions in the first stem or the second stem may be spirally disposed therearound.

In some embodiments, the first stem or the second stem may have a surface area, and 50% or less of the surface area may be configured to contact bone in the first medullary canal or the second medullary canal.

The therapeutic agent delivery system may further comprise an outlet fluidly coupled to the first stem, the second stem, or the coupling member.

In another aspect of the present invention, a method for treating a joint comprises positioning a first intramedullary stem in a first medullary canal of a first bone, positioning a second intramedullary stem in a second medullary canal of a second bone, coupling the first intramedullary stem to the second intramedullary stem with a coupling member therebetween, and delivering a therapeutic agent to the first and second medullary canals.

In some embodiments, the coupling member may comprise an adjustable height manifold, and the method may further comprise actuating the adjustable height manifold, thereby adjusting a distance between a first end of the first intramedullary stem and a first end of the second intramedullary stem. Actuating the adjustable height manifold may comprise rotating a nut coupled to a housing of the adjustable height manifold, and rotating the nut can move an adjustable connector of the adjustable height manifold relative to the housing.

In some embodiments, the coupling member may comprise a wedge element having a fixed height, and the method may further comprise selecting a wedge element from a plurality of wedge elements having different fixed heights. Coupling the first stem to the second stem with the coupling member may comprise coupling the first intramedullary stem to the second intramedullary stem with the selected wedge element therebetween, thereby adjusting a distance between a first end of the first intramedullary stem and a first end of the second intramedullary stem.

In some embodiments, positioning the first intramedullary stem in the first medullary canal or positioning the second intramedullary stem in the second medullary canal may comprise engaging a plurality of protrusions on the first or second stem with bone lining the respective first or second medullary canal.

In some embodiments, delivering the therapeutic agent may comprise delivering an antibiotic, wherein the antibiotic may comprise vancomycin, tobramycin, or a combination thereof.

In some embodiments, delivering the therapeutic agent may comprise delivering the therapeutic agent from one or more outlet holes disposed in a fluted region of the first stem or the second stem.

In some embodiments, the first bone may be a femur and the second bone may be a tibia.

In some embodiments, coupling may comprise engaging a flanged region in the adjustable height manifold with a recessed region in the first end of the first stem or the second stem.

In some embodiments, delivering the therapeutic agent may comprise pumping the therapeutic agent from the first stem or the second stem to the respective first or second medullary canal.

The method may further comprise suctioning unwanted fluids from the first or the second medullary canal, wherein the unwanted fluids pass through one or more holes in the first stem or the second stem.

In some embodiments, positioning the first stem or the second stem may comprise positioning the first stem or the second stem in the respective medullary canal such that 50% or less of a surface area of the first stem or the second stem contacts bone in the respective first or second medullar canal.

In another aspect of the present invention, a therapeutic agent delivery system comprises a femoral head configured to be disposed in an acetabulum, and a femoral stem coupled to the femoral head, the femoral stem configured to be disposed in a femoral medullary canal. The system may further comprise an inlet coupled to the femoral stem, and a plurality of outlets in the femoral head or the femoral stem. The therapeutic agent may be introduced into the system from the inlet, and the therapeutic agent may be deliverable from the plurality of outlets into the acetabulum or the femoral medullary canal.

In some embodiments, the femoral stem may comprise a threaded neck region, the threaded neck region configured to be threadably engaged with the femoral head thereby allowing adjustment of a distance between the femoral head and the femoral stem.

In some embodiments, the femoral stem may comprise a plurality of protrusions extending axially along a longitudinal axis of the femoral stem.

In some embodiments, the femoral stem may comprise an elongate channel extending therethrough, the channel fluidly coupled with the inlet and the plurality of outlets. The elongate channel may be a through hole, wherein one end of the femoral stem comprises a plug.

In some embodiments, the femoral stem may be tapered.

In some embodiments, the plurality of outlets may be disposed in the femoral head. The femoral head may comprise a central channel, the central channel fluidly coupled with the plurality of outlets via a plurality of channels extending radially outward from the central channel.

The therapeutic agent delivery system may further comprise an outlet for fluid removal from the femoral head or the femoral stem.

The therapeutic agent delivery system may further comprise an acetabular cup coupled to the femoral head, wherein the therapeutic agent is delivered from the acetabular cup to the acetabulum.

In some embodiments, the plurality of outlets may comprise a plurality of holes having varying diameters.

In some embodiments, the femoral head may be at least partially hollow.

The therapeutic agent delivery system may further comprise a locking mechanism for locking the femoral head with the femoral stem.

In another aspect of the present invention, a method for treating a joint comprises positioning a femoral stem in a medullary canal of a femur, coupling a femoral head with the femoral stem, positioning the femoral head in an acetabulum, and delivering a therapeutic agent to the medullary canal and the acetabulum.

In some embodiments, the coupling may comprise adjusting a distance between the femoral head and the femoral head. In some embodiments, the coupling may comprise threadably engaging the femoral head with the femoral stem.

In some embodiments, positioning the femoral stem may comprise engaging a plurality of protrusions on the femoral stem with bone lining the medullary canal.

In some embodiments, delivering the therapeutic agent may comprise delivering an antibiotic, wherein the antibiotic may comprise vancomycin, tobramycin, or a combination thereof.

In some embodiments, delivering the therapeutic agent may comprise delivering the therapeutic agent from one or more outlet holes disposed in a fluted region of the femoral stem.

In some embodiments, delivering the therapeutic agent may comprise pumping the therapeutic agent from the femoral stem to the medullary canal or from the femoral head to the acetabulum.

The method may further comprise suctioning unwanted fluids from the medullary canal or the acetabulum.

In some embodiments, positioning the femoral stem may comprise positioning the femoral stem into the medullary canal such that 50% or less of a surface area of the femoral stem contacts bone in the medullary canal.

In another aspect of the present invention, a device for delivering a therapeutic agent to a joint in a patient comprises an implant having a plurality of outlets for delivering the therapeutic agent to the joint, wherein the joint is a shoulder joint, an ankle joint, or a spinal joint.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A is a perspective view of an exemplary therapeutic agent delivery system for a knee;

FIG. 1B is an exploded view of the therapeutic agent delivery system of FIG. 1A;

FIG. 2A is a perspective view of an exemplary intramedullary stem;

FIGS. 2B and 2C are side views of an exemplary intramedullary stem;

FIG. 8A is a perspective view of an exemplary embodiment of an adjustable connector of the adjustable height manifold of FIGS. 4A-4B;

FIG. 8B is a bottom view of the adjustable connector of FIG. 8A;

FIGS. 8C and 8D are side views of the adjustable connector of FIG. 8A;

FIG. 9 shows an exemplary embodiment of a manifold pin of the adjustable height manifold of FIGS. 4A-4B;

FIG. 10A is a top view of the assembled adjustable height manifold in the collapsed configuration, as shown in FIG. 4A;

FIG. 10B is a vertical cross sectional view of the assembled adjustable height manifold of FIG. 10A;

FIG. 11A is a perspective view of an exemplary embodiment of a fixed height wedge;

FIGS. 11B and 11C are side views of the fixed height wedge of FIG. 11A;

FIGS. 12A-12H illustrate an exemplary mechanism for coupling an intramedullary stem to a coupling member;

FIG. 17A is a perspective view of an exemplary therapeutic agent delivery system for a hip;

FIG. 17B is an exploded view of the therapeutic agent delivery system of FIG. 17A;

FIG. 18A is a perspective view of an exemplary embodiment of a femoral stem;

FIG. 18B is a side view of the femoral stem of FIG. 18A;

FIG. 18C is a side cross-sectional view of the femoral stem of FIG. 18A;

FIG. 18D is a bottom view of the femoral stem of FIG. 18A;

FIG. 19 shows an exemplary embodiment of a stem plug;

FIGS. 28A and 28B illustrate the use of negative pressure wound therapy with an intramedullary device;

FIGS. 32A and 32B illustrate an exemplary configuration for the internal channels of an intramedullary device;

FIGS. 33A-33C illustrate another exemplary configuration for the internal channels of an intramedullary device; and FIGS. 34-36 show exemplary embodiments of therapeutic agent delivery systems.

DETAILED DESCRIPTION OF THE INVENTION

Figure 3A:
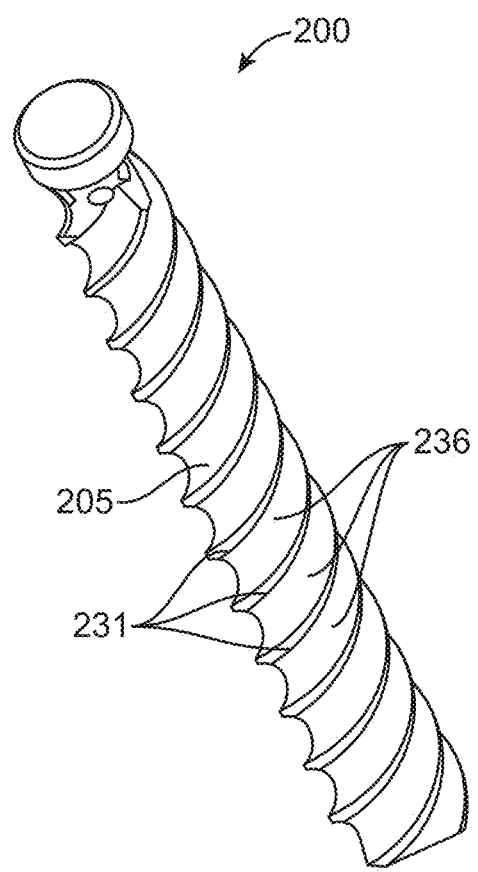
FIGS. 3A and 3B show alternative embodiments of the elongate body of an intramedullary stem.

Specific embodiments of the disclosed device, delivery system, and method will now be described with reference to the drawings. Nothing in this detailed description is intended to imply that any particular component, feature, or step is essential to the invention.

Described herein are therapeutic agent delivery systems that may be used in a knee joint, a hip joint, or any other joint. For example, the therapeutic agent delivery system may be used to treat a shoulder or ankle joint, or a portion of the spine. One of skill in the art will appreciate that other joints may also be treated with the systems, devices, and methods disclosed herein. Optionally in any embodiment, the therapeutic agent delivery system may comprise one or more intramedullary stems, configured to be disposed stably in a medullary canal of a bone. The intramedullary stem may be configured to deliver the therapeutic agent to the medullary canal, the joint space, or a combination thereof. Optionally, in any embodiment, an intramedullary stem is coupled to another component, such as another intramedullary stem or a femoral head, in a way that allows the distance between the stem and the other component to be adjusted to fit a patient, or the distance therebetween may be fixed.

The therapeutic agent delivered by the delivery systems described herein may comprise any fluid. For example, the therapeutic agent may comprise an antibiotic fluid such as a vancomycin or tobramycin, combinations thereof, or other antibiotics commonly used to treat implant-associated infections. One of skill in the art will appreciate that any therapeutic agent may be also be delivered alone, or in combination with an antibiotic or other therapeutic agent. Other exemplary therapeutic agents may include saline or other fluids used to irrigate the joint or medullary canals being treated.

Therapeutic Agent Delivery System for Knee

FIGS. 1A and 1B show an exemplary therapeutic agent delivery system 100 for a knee. FIG. 1A shows the components of the delivery system assembled together, while FIG. 1B shows the components of the delivery system disassembled and aligned for assembly. The delivery system 100 comprises a first intramedullary stem 110, a second intramedullary stem 120, and a coupling member 130. Each of the two intramedullary stems 110 and 120 can be configured be disposed in a medullary canal of a bone. For example, the first intramedullary stem 110 can be configured to be disposed in the medullary canal of a femur of a patient, while a second intramedullary stem 120 can be configured to be disposed in the medullary canal of a tibia of the patient. The coupling member 130, configured to be disposed in the joint space, can couple the two stems in a stable configuration, while maintaining a desired distance 105 between the two stems throughout the length of use of the therapeutic agent delivery system in a patient.

The first intramedullary stem 110 and the second intramedullary stem 120 may be any intramedullary stem as described herein. The two stems may be two identical stems, or they may be two different stems, configured to have one or more differences in dimensions, configurations, or features. For example, the delivery system may comprise a first intramedullary stem specifically configured to engage a femur, and a second intramedullary stem specifically configured to engage a tibia. The two stems may differ in one or more dimensions, such as length, diameter, or degree of taper. Alternatively or in combination, the two stems may differ in one or more configurations or features as described herein (e.g., configuration of the stem channel, number, shape, and size of the protrusions, the fluted regions, and/or the outlet holes, etc.).

The coupling member 130 may comprise any coupling member as described herein, such as an adjustable height manifold or a fixed height wedge. In many embodiments of the delivery system 100, the coupling member 130 can be configured to allow the distance 105 between the two stems to be adjusted, so as to accommodate the anatomy of the patient. The coupling member can be configured to fluidly couple to a source of a therapeutic agent and receive the therapeutic agent, and distribute the therapeutic agent to the intramedullary stems for delivery to the medullary canals.

The first stem 110 and the second stem 120 may be releasably coupled to the coupling member 130. Each of the first stem and the second stem may be configured to couple to a stem connector 132 of the coupling member. The first stem may couple to a first stem connector 132a, and the second stem may couple to a second stem connector 132b. Various mechanisms for the connection between the stem and the coupling member are described herein, any of which may be incorporated into the coupling member 130 for coupling with the first stem or the second stem. The first stem and the second stem may couple to the first stem connector and the second stem connector, respectively, via identical mechanisms or via different mechanisms. Accordingly, the first stem connector 132a and the second stem connector 132b of the coupling member may be identical or different. In preferred embodiments, the first stem and the second stem are identical, such that the coupling member accordingly comprises two identical stem connectors configured to couple to the first stem and the second stem via identical mechanisms.

Intramedullary Stem

FIGS. 2A-2C show an exemplary intramedullary stem 200, suitable for incorporation with a therapeutic agent delivery system for a knee. FIG. 2A is a perspective view, and FIGS. 2B and 2C are side views of the intramedullary stem 200. Each intramedullary stem 200 comprises an elongate body 205 having a longitudinal axis 210, the elongate body having a first end 215 and a second end 220 opposite the first end. The first, or proximal, end may be configured to couple to a coupling member 130, such as an adjustable height manifold or a fixed height wedge as described herein. The second, or distal, end may be disposed in the medullary canal of a bone. The elongate body 205 comprises a stem channel 225 extending between the first end 215 and the second end 220, the stem channel configured to deliver the therapeutic agent through the stem and to the medullary canal. The first end 215 of the intramedullary stem 200 may be configured to couple the stem to a coupling member. The first end may comprise any mechanism for connecting the stem to the coupling member (e.g., flanged region, dovetail joints, snap buckle, winged nut, etc.), as described in further detail herein.

The intramedullary stem 200 may comprise a plurality of protrusions 230, protruding radially outward from the elongate body 205. The plurality of protrusions may comprise any number of protrusions having any appropriate shape, size, or configuration to engage the medullary canal in a stable fashion. For example, the protrusions may comprise elongate fins extending along the longitudinal length of the elongate body, as shown in FIGS. 2A-2C. In one exemplary embodiment, the plurality of protrusions may comprise four fins, spaced equally at about 90° about the longitudinal axis 210 of the elongate body. The plurality of protrusions 230 and the elongate body 205 may be formed separately and coupled together. Alternatively or in combination, the plurality of protrusions 230 may be formed by removing material from the elongate body 205, such that the plurality of protrusions and the elongate body are formed as a single member. Adjacent protrusions 230 may define one or more fluted regions 235 therebetween, the fluted regions radially recessed compared to the protrusions. The fluted regions may form a concave recessed region between adjacent protrusions.

The plurality of protrusions and fluted regions can be configured to minimize the surface area of the stem contacting the bone lining the medullary canal, such that the area of the bone flushed with the therapeutic agent may be maximized. For example, the plurality of protrusions and fluted regions can be configured such that less than 50% of the surface area of the stem is in contact with the bone lining the medullary canal. Of course this is not intended to be limiting and one of skill in the art will appreciate that any percentage of the surface area of the stem may contact the bone. The stem may comprise a plurality of identical fluted regions defined by a plurality of elongate fins, distributed symmetrically about the longitudinal axis 210 of the stem, as shown in FIGS. 2A-2C. Alternatively, a plurality of fluted regions may be distributed asymmetrically about the longitudinal axis of the stem, and/or may have different shapes or sizes as described in further detail herein.

An intramedullary stem 200 may further comprise a plurality of outlet holes 240 in fluid communication with the stem channel 225. The plurality of outlet holes 240 may be configured to deliver the therapeutic agent, distributed through the stem channel 225, to the medullary canal, as well as adjacent tissue including the joint. The plurality of outlet holes may be disposed in a fluted region 235, so as to deliver the therapeutic agent to the area of the bone not in contact with the intramedullary stem. The plurality of outlet holes may comprise any number of outlet holes having any appropriate size, shape, or distribution. For example, the plurality of outlet holes may include a plurality of equally sized and spaced holes that extend axially along a line substantially parallel to the longitudinal axis 210 of the stem, as shown in FIGS. 2A-2C. The plurality of outlet holes may be arranged in various configurations, as described in further detail herein. The plurality of outlet holes may comprise holes having an identical shape and/or size, or holes having various shapes and/or sizes. Varying the hole size may allow further fluid control of therapeutic agent as it exits different regions of the stem.

The stem channel 225 may be a through hole that extends from the first end 215 to the second end 220 through both the first end and the second end, such that the elongate body comprises an open second or distal end. The system may further comprise a plug (not shown) configured to couple to the open second end of the stem, so as to close the second end and thereby create a blind channel. Alternatively, the stem channel 225 may be a blind channel, wherein the second end of the elongate body is closed. In configurations wherein the second end is open, the therapeutic agent may exit the stem channel into the medullary canal through the second end and/or through a plurality of outlet holes disposed along the elongate body 205 as described herein. If the stem comprises only the stem channel 225 extending through the first and second ends, without the plurality of outlet holes, the therapeutic agent may exit the stem channel only through the second end. In configurations wherein the second end of the stem is closed, the therapeutic agent may exit the stem channel into the medullary canal only through the plurality of outlet holes.

The intramedullary stem 200 may be tapered to fit the medullary canal. For example, the elongate body 205 and/or the plurality of protrusions 230 may be tapered from the first end 215 to the second end 220, as shown, so as to have a smaller radial cross-sectional area at the second end than at the first end. For example, the taper may comprise a gradual taper, wherein the extent of the taper may be preferably in a range from about 0.1° to about 10°, more preferably about 0.5° to about 5°, and even more preferably about 1° to about 5°, or about 1° to about 4°, or about 2° or about 3°. The taper may be adjusted to accommodate a medullary canal of a specific type of bone.

The exemplary embodiment of FIGS. 2A-2C may comprise one or both of two intramedullary stems of a therapeutic agent delivery system for a knee as shown in FIGS. 1A and 1B. Preferably, the therapeutic agent delivery system for a knee comprises two identical intramedullary stems, such as the exemplary embodiment of FIGS. 2A-2C.

Figure 3B:
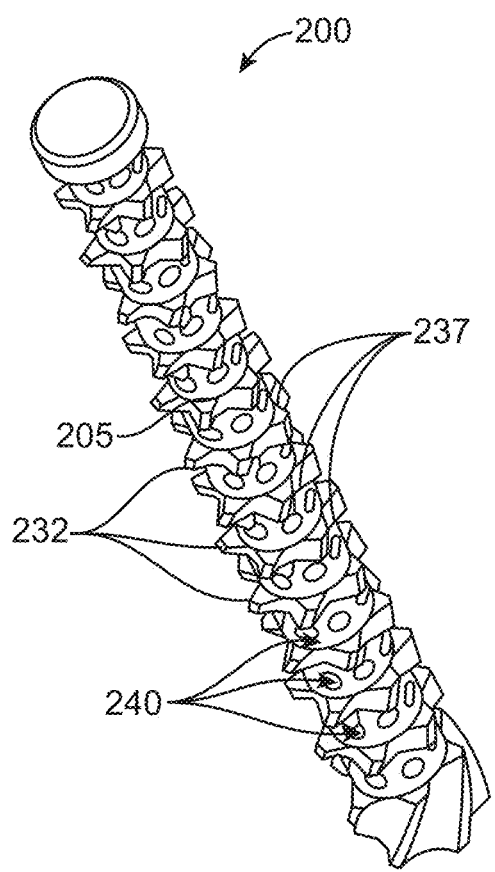

FIGS. 3A and 3B show alternative embodiments of the elongate body 205 of the intramedullary stem 200 of FIGS. 2A-2C. FIG. 3A shows an elongate body 205 comprising one or more protrusions 231 spirally disposed around the elongate body 205 along the longitudinal length of the body. Adjacent spiral or helical protrusions 231 define one or more fluted regions 236 therebetween, also spirally disposed around the elongate body. FIG. 3B shows an elongate body 205 comprising a plurality of protrusions 232 resulting from cutting away or otherwise removing portions of the spirally disposed protrusions 231 shown in FIG. 3A. For example, as shown, a plurality of radial cuts may be made to elongate body to define the plurality of protrusions 232. A plurality of fluted regions 237 may be defined between remaining portions of adjacent helical protrusions. Cutting away or removing portions of the spiral protrusions 231 as shown in FIG. 3B can further decrease the contact area between the stem and the bone, thus allowing the therapeutic agent to flow more freely along the medullary canal.

In the embodiment of FIG. 3A, a plurality of outlet holes (not shown) may extend along a helical or spiral line, such as along the helical or spiral fluted regions 236. In the embodiment shown in FIG. 3B, the plurality of outlet holes 240 may disposed in the fluted regions 237, such that the holes extend about a plurality of rings around the circumference of the elongate body.

Adjustable Height Manifold

Figure 4A:
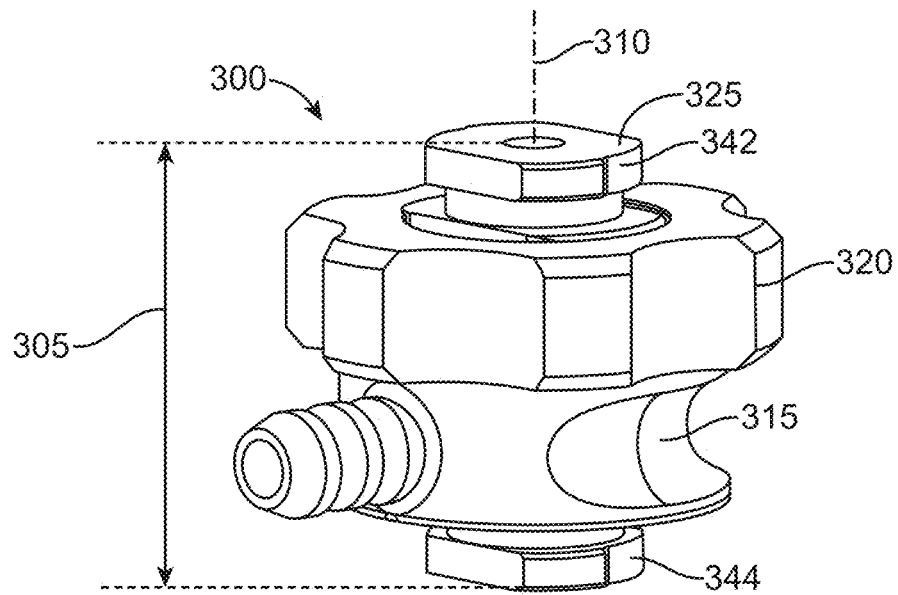
FIG. 4A shows an exemplary embodiment of an adjustable height manifold in a collapsed configuration.
Figure 4B:
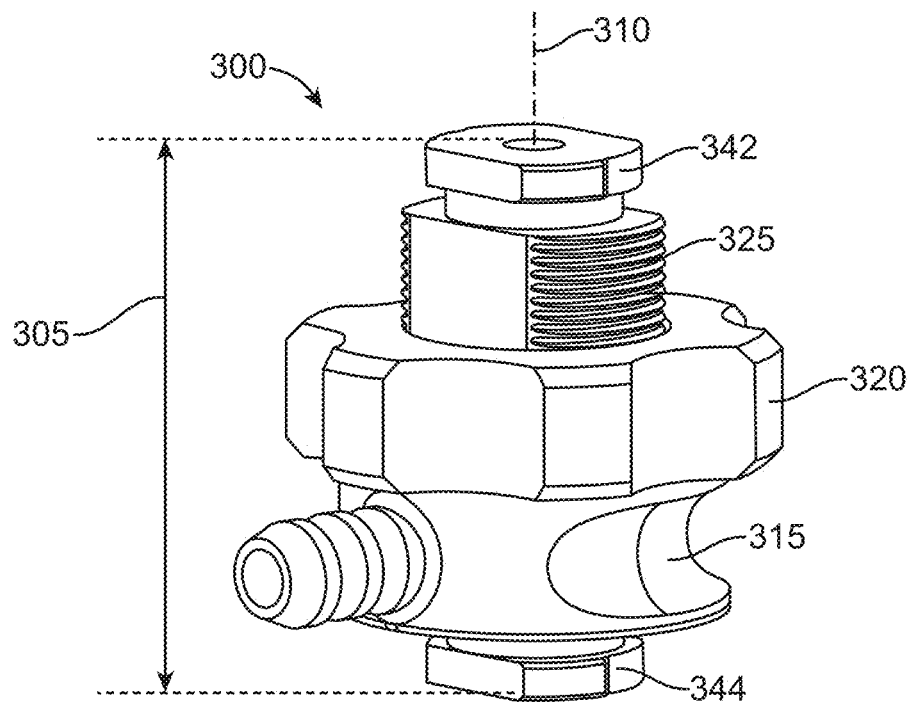
FIG. 4B shows the adjustable height manifold of FIG. 4A in an extended configuration.

FIGS. 4A and 4B show an adjustable height manifold 300 suitable for incorporation with a therapeutic agent delivery system for a knee such as in FIGS. 1A-1B. The adjustable height manifold 300 is one example of a coupling member that can couple the two intramedullary stems in a stable configuration, while maintaining a desired distance between the two stems throughout the length of use of the therapeutic agent delivery system in a patient. The adjustable height manifold further enables the adjustment of the distance between the two stems, such that the delivery system may be configured to optimally accommodate the anatomy of the patient. The adjustable height manifold 300 may comprise a housing 315, a rotating nut 320, and an adjustable connector 325. The rotating nut 320 and adjustable connector 325 may be coupled to the housing 315, and configured so as to allow the manifold height 305 to be increased or decreased, based on the desired set distance between the two stems for a patient. Rotating the nut 320 in clockwise and counterclockwise directions can collapse or extend the manifold, by translating the adjustable connector along a longitudinal axis 310 of the manifold. FIG. 4A shows the adjustable height manifold 300 in a collapsed configuration, such that the manifold height 305 is relatively short and the manifold can thus fit a patient who requires a shorter set distance between the two knee stems. FIG. 4B shows the adjustable height manifold 300 in an extended configuration, such that the manifold height 305 is relatively long and the manifold can thus fit a patient who requires a longer set distance between the two knee stems.

The adjustable height manifold 300 further comprises a first stem connector 342 and a second stem connector 344, disposed on opposite sides of the housing. The first stem connector 342 may be configured to couple to a first end of a first intramedullary stem, and the second stem connector 344 may be configured to couple to a first end of a second intramedullary stem. The first stem connector 342 may be coupled to the adjustable connector 325, while the second stem connector 344 may be coupled to the housing 315. Each stem connector may comprise a connection mechanism to couple to a corresponding connection mechanism disposed on the first end of the intramedullary stem. The first and second stem connectors may comprise different connection mechanisms, or they may comprise identical connection mechanisms. In preferred embodiments, the first and second stem connectors comprise identical connection mechanisms, and have a fixed orientation relative to one another, such that the orientation remains the same during actuation of the adjustable height manifold to adjust the manifold height. The fixed orientation of the two stem connectors relative to one another can allow proper and simultaneous coupling of the manifold to each stem during the implantation of the delivery system in a patient using the same actuation motion for both stems.

Figure 5:
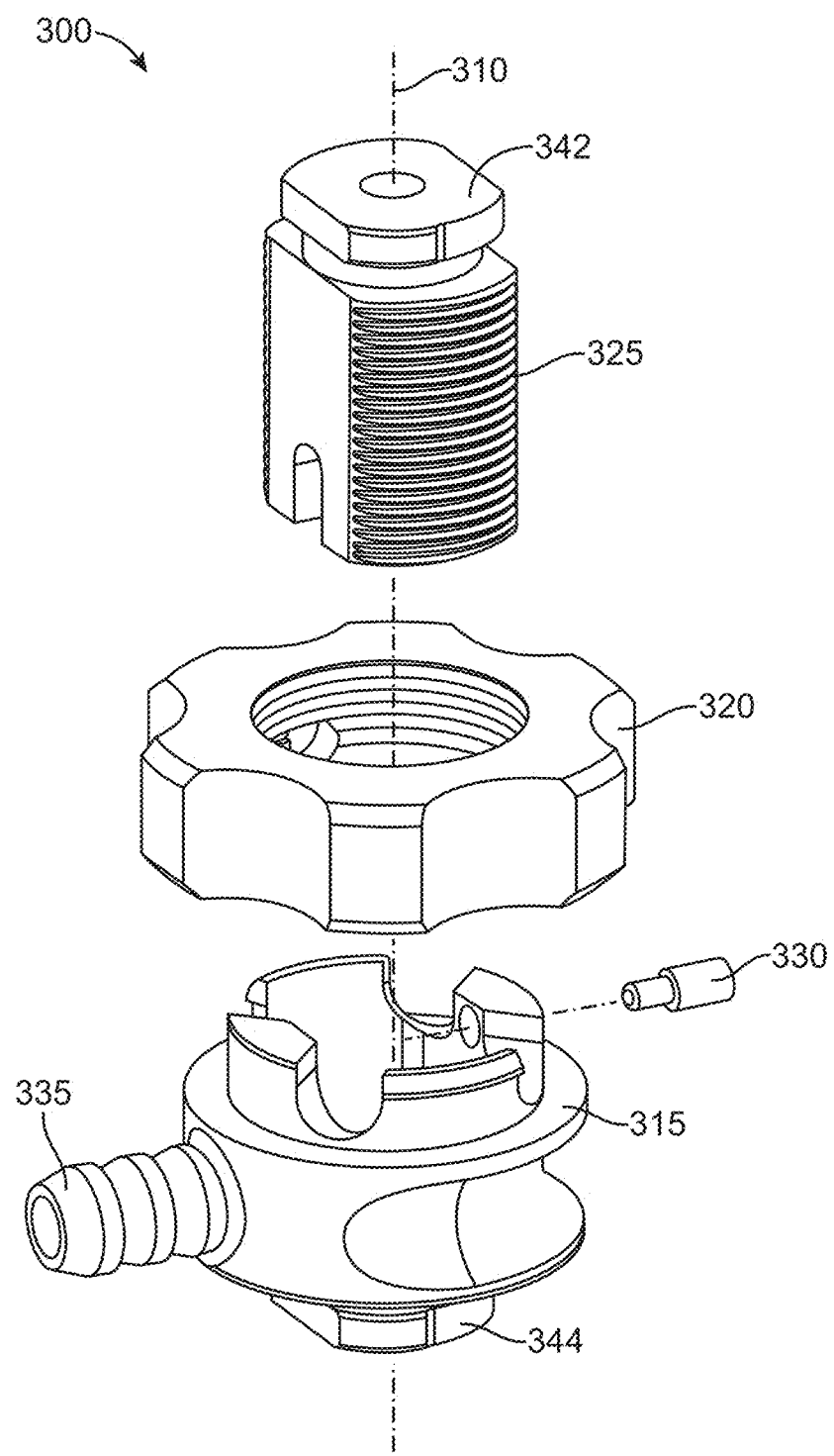
FIG. 5 is an exploded view of the adjustable height manifold of FIG. 4A.

FIG. 5 is an exploded view of the adjustable height manifold 300 of FIGS. 4A-4B. The adjustable height manifold 300 comprises a housing 315, a rotating nut 320 having a scalloped outer surface to provide gripping regions for an operator's fingers and internal threads, and an adjustable connector 325, wherein the three components are axially aligned along a longitudinal axis 310 of the manifold. The manifold further comprises a manifold pin 330, configured to secure the coupling of the adjustable connector the housing and control the range of motion of the adjustable connector. The adjustable connector comprises a first stem connector 342, configured to couple to a first intramedullary stem. The housing comprises a second stem connector 344, configured to couple to a second intramedullary stem. The housing further comprises an inlet 335 coupled thereto, the inlet configured to fluidly couple to a source of the therapeutic agent (not shown) to be delivered to the patient. The housing is configured to couple to the rotating nut and slidably receive the adjustable connector. The rotating nut is configured to threadably engage the adjustable connector, so as to cause the adjustable connector to extend outwards from housing along the longitudinal axis 310, or retract inwards into the housing along the longitudinal axis when the nut is rotated.

Figure 6A:
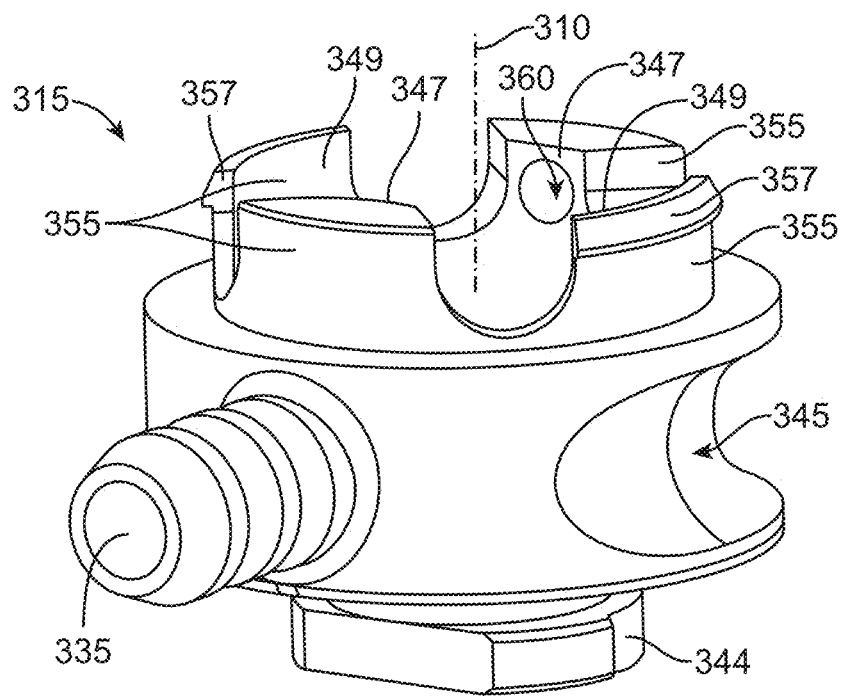
FIG. 6A is a perspective view of an exemplary embodiment of a housing of the adjustable height manifold of FIG. 4A.
Figure 6B:
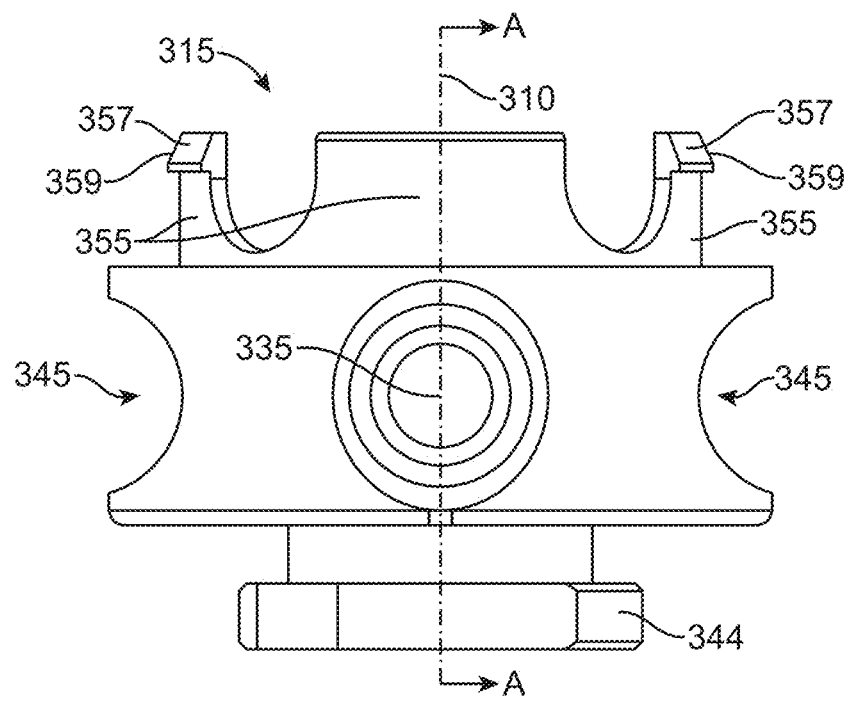
FIG. 6B is a side view of the housing of FIG. 6A.
Figure 6C:
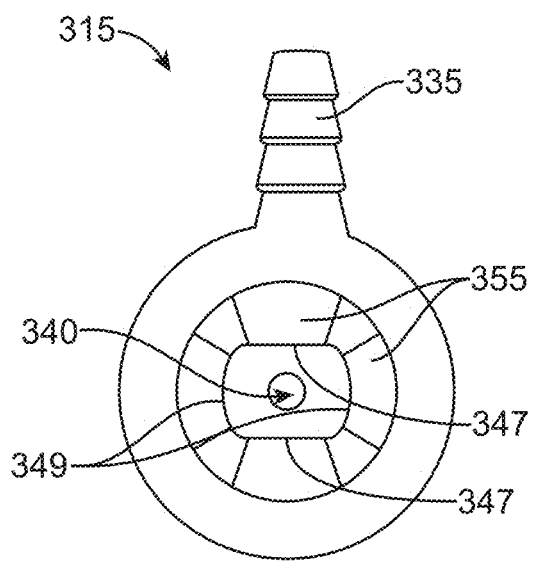
FIG. 6C is a top view of the housing of FIG. 6A.
Figure 6D:
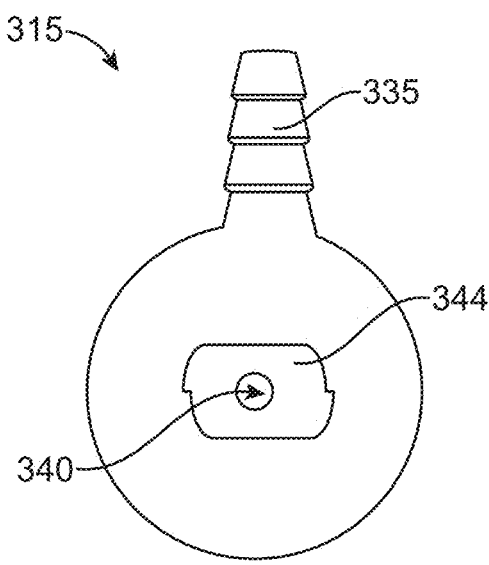
FIG. 6D is a bottom view of the housing of FIG. 6A.
Figure 6E:
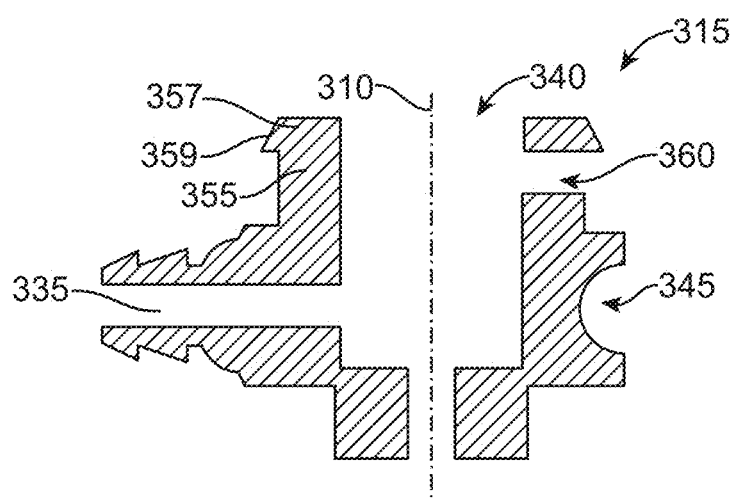
FIG. 6E is a vertical cross sectional view of the housing of FIG. 6A.

FIGS. 6A-6E show an exemplary embodiment of a housing 315 of the adjustable height manifold 300 of FIGS. 4A-4B. FIG. 6A is a perspective view, FIG. 6B is a side view, FIG. 6C is a top view, FIG. 6D is a bottom view, and FIG. 6E is a vertical cross sectional view (cross section A-A of FIG. 6B) of the housing 315. The housing 315 comprises an inlet 335 to fluidly couple to a source of the therapeutic agent, and a housing channel 340 (best seen in FIG. 6E) extending along the longitudinal axis 310 through the housing. The housing channel 340 is in fluid communication with the inlet 335, such that the therapeutic agent added to the therapeutic agent delivery system through the inlet can be distributed to other components of the delivery system through the housing channel. The inlet 335 may comprise a barbed outer surface, to securely engage the inner surface of a tube (best seen in FIG. 28A) supplying the therapeutic agent. The housing may further comprise a concave groove 345, disposed at least partially or completely about the circumference of the housing thereby minimizing profile of the tubing/housing assembly. The groove can allow for placement of tubing supplying the therapeutic agent, coupled to the inlet 335.

The housing 315 further comprises a second stem connector 344, configured to couple to an intramedullary stem such as any intramedullary stem described herein. The housing channel 340 can extend through the stem connector 344, such that the housing channel can be fluidly coupled to a stem channel of a stem coupled to the stem connector. The stem connector 344 may comprise any mechanism for connecting the coupling member to the stem (e.g., flanged region, dovetail joints, snap buckle, winged nut, etc.), as described in further detail herein.

The housing channel 340 may be configured to have a geometry that allows the adjustable connector disposed in the channel to slide axially along the longitudinal axis 310, while preventing the adjustable connector from rotating within the channel. For example, the channel 340 may comprise two flat inner surfaces 347 disposed opposite one another, configured to interface with two flat side surfaces of the of adjustable connector. The channel may further comprise two rounded side inner surfaces 349, configured to interface with two corresponding rounded surfaces of the adjustable connector. For example, the rounded inner surfaces 347 may comprise concave surfaces, while the rounded side surfaces of the adjustable connector may comprise convex surfaces. The interfacing of the flat inner surfaces of the housing channel with the flat side surfaces of the adjustable connector can prevent the adjustable connector from rotating therein, ensuring that the adjustable connector moves only slidably, not rotatably, within the housing channel. Preventing rotation of the adjustable connector, which comprises the first stem connector 342, can ensure that the orientation of the second stem connector 344 remains fixed with respect to the orientation of the first stem connector, even when the rotating nut 320 is rotated. The fixed orientation of the first and second stem connectors with respect to one another can ensure that the manifold can easily couple to both the first stem and the second stem. For example, the manifold can be inserted into the space between the first and second stems and then rotated in one direction to couple to both stems. Such a configuration of the stem connectors can facilitate the implantation of the delivery system in a patient, by obviating the potential need to rotate one or more intramedullary stems after the stems have already been inserted into the patient's medullary cavities.

The housing may further comprise one or more prongs 355, disposed about the periphery of the housing channel 340 and projecting longitudinally from housing. The prongs may comprise four prongs as shown in FIGS. 6A-6E, each internal surface of the prong configured to engage each of the four sides of the adjustable connector to be disposed in the housing channel. Two of the prongs, disposed opposite one another, can be configured to have the flat inner surfaces 347 of the housing channel, while two of the remaining prongs, also disposed opposite one another, can be configured to have the rounded inner surfaces 349 of the housing channel. One or more of the prongs may further comprise an outward facing lip 357 disposed at the edge of the prong. The lip 357 may be configured to engage a corresponding manifold groove in the rotating nut as described in further detail herein, so as to securely couple the rotating nut to the housing and prevent axial movement of the rotating nut along the longitudinal axis 310 during rotation of the nut. The lip 357 may further comprise chamfers 359, configured to facilitate the coupling of the rotating nut to the housing by guiding the lip into the manifold groove of the nut.

The housing may further comprise a housing pin hole 360, configured to receive a portion of the manifold pin. The pin hole 360 may be disposed on a prong 355 configured to engage the rotating nut, such that the pin hole 360 can be aligned with a nut pin hole in the rotating nut also configured to receive the manifold pin. When fully assembled, the manifold pin can be disposed partially in the housing and partially in slot in the adjustable connector disposed within the housing channel, to create a hard stop to prevent the manifold assembly from coming apart, as described in further detail herein. The housing pin hole 360 may be dimensioned to ensure the retention of the manifold pin within the pin hole. For example, the housing pin hole can have a diameter that is substantially equal to the diameter of the portion of the manifold pin configured to be disposed in the housing, such that the pin can be press fit into the housing pin hole.

Figure 7A:
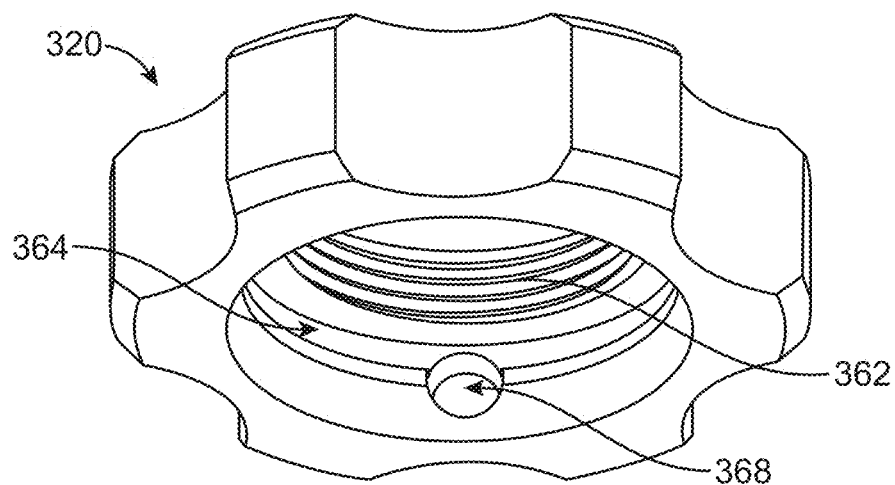
FIG. 7A is a perspective view of an exemplary embodiment of a rotating nut of the adjustable height manifold of FIGS. 4A-4B.
Figure 7B:
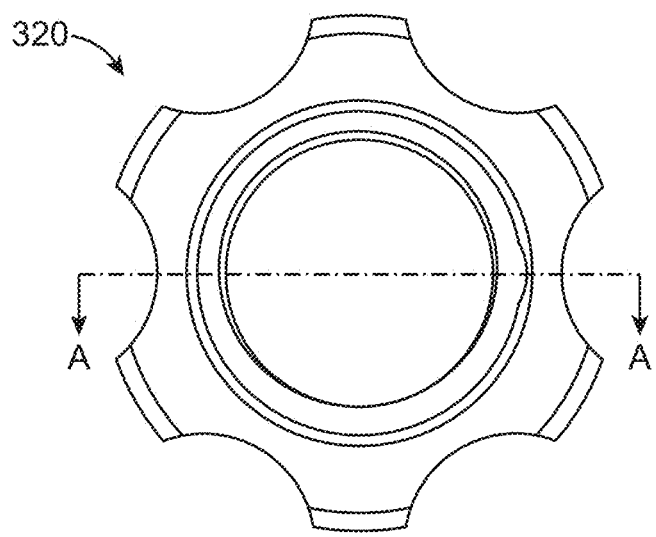
FIG. 7B is a top view of the rotating nut of FIG. 7A.
Figure 7C:
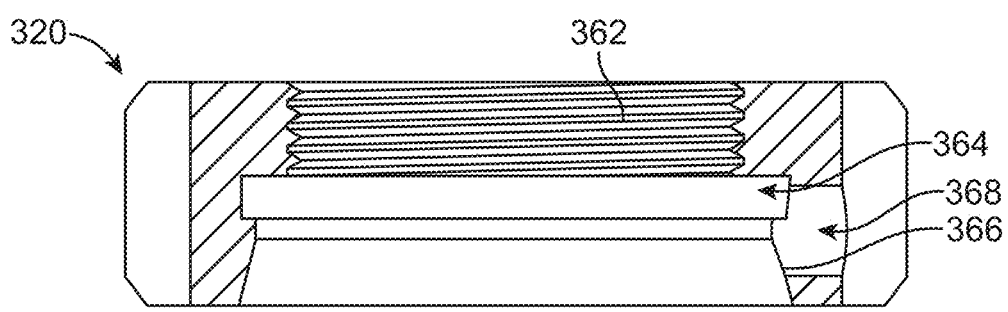
FIG. 7C is a vertical cross sectional view of the rotating nut of FIG. 7A.

FIGS. 7A-7C show an exemplary embodiment of a rotating nut 320 of the adjustable height manifold 300 of FIGS. 4A-4B. FIG. 7A is a perspective view, FIG. 7B is a top view, and FIG. 7C is a vertical cross sectional view (cross section A-A of FIG. 7B) of the rotating nut 320. The rotating nut 320 comprises a plurality of threads 362 disposed on a portion of its inner surface. The threads 362 may be configured to engage corresponding threads on a portion of the adjustable connector, such that rotation of the nut 320 about the adjustable connector can cause axial movement of the adjustable connector along the longitudinal axis of the manifold. The nut 320 may further comprise a manifold groove 364 disposed circumferentially about the inner surface of the nut. The manifold groove may be configured to receive one or more lips disposed on one or more prongs of the housing as described herein, so as to lock the nut onto the housing while still allowing rotation of the nut relative to the housing. The nut may further comprise chamfers 366 disposed below the manifold groove, extending circumferentially about the inner surface of the nut. The chamfers 366 can be configured to correspond to the chamfers of a housing lip, so as to guide the lip into the manifold groove. The nut may further comprise a nut pin hole 368 disposed on a portion of the nut below the threads 362, the nut pin hole configured to receive the manifold pin therethrough. During assembly of the manifold, the manifold pin may be pushed into and completely through the body of the rotating nut, to dispose the pin partially within the housing and partially within the adjustable connector and thereby avoiding physical obstruction of the rotation of the nut by the pin. Accordingly, when the manifold is completely assembled, the manifold pin does not traverse any portion of the rotating nut, such that the rotating nut can rotate freely. The nut pin hole 368 may be dimensioned to facilitate the insertion of the manifold pin into and through the pin hole. For example, the nut pin hole can have a diameter that is greater than the diameter of the largest portion of the manifold pin, such that the pin can easily pass through the nut pin hole.

FIGS. 8A-8D show an exemplary embodiment of an adjustable connector 325 of the adjustable height manifold 300 of FIGS. 4A-4B. FIG. 8A is a perspective view, FIG. 8B is a bottom view, and FIGS. 8C and 8D are side views. The adjustable connector 325 comprises an adjustable connector channel 370 extending axially along the longitudinal axis 310. The channel 370 extends through the length of the adjustable connector, and is configured to be in fluid communication with the housing channel 340 and hence with the inlet 335 fluidly coupled to the housing channel. The adjustable connector further comprises a first stem connector 342, configured to couple to an intramedullary stem such as any intramedullary stem described herein. The connector channel 370 extends axially through the stem connector 342, such that the channel 370 is in fluid communication with the stem channel of the stem coupled to the first stem connector 342. The stem connector 342 may comprise any mechanism for connecting the coupling member to the stem (e.g., flanged region, dovetail joints, snap buckle, winged nut, etc.), as described in further detail herein.

The adjustable connector may further comprise threads 372 configured to engage corresponding threads of the rotating nut, such that rotation of the nut can cause vertical movement of the adjustable connector into or out of the housing. The adjustable connector may comprise two flat side surfaces 327 and the two rounded side surfaces 329, wherein the flat side surfaces may be configured to interface with the flat inner surfaces of the housing channel, and wherein the rounded side surfaces may be configured to interface with the rounded inner surfaces of the housing channel. As described herein, such a configuration can prevent the adjustable connector from rotating when the rotating nut is rotated, ensuring that the orientation of the adjustable connector and hence the first stem connector 342 remains constant with respect to the orientation of the second stem connector. Moreover, this translates the rotational actuation of the nut into linear motion of the adjustable connector.

FIG. 8C shows the proximal flat side surface 327a of the adjustable connector, configured to be oriented proximally with respect to the inlet of the housing. The proximal flat side surface can be configured to have an open slot 374 that extends through the bottom of the adjustable connector. The open slot 374 may be fluidly coupled to the adjustable connector channel 370, as best seen in FIG. 8B showing the bottom view of the adjustable connector. The open slot 374 may be configured such that when the assembled manifold is in the collapsed configuration as shown in FIG. 4A, the open slot is aligned with the inlet so as to fluidly couple the inlet to the adjustable connector channel 370. When the assembled manifold is in the extended position as shown in FIG. 4B, the open bottom of the open slot 374 can ensure that the inlet remains in fluid communication with the housing channel, and thereby with the adjustable connector channel.

FIG. 8D shows the distal flat side surface 327b of the adjustable connector, configured to be oriented distally with respect to the inlet of the housing. The distal flat side surface comprises a closed slot 376, configured to engage a portion of the manifold pin retained in the housing. As described herein, the manifold pin may be coupled to the manifold assembly after the housing, rotating nut, and adjustable connector are assembled together. After full assembly, the manifold pin may be partially disposed in the housing, and partially disposed in the closed slot 376 of the adjustable connector. The manifold pin can be configured to remain engaged in the closed slot 376 during retraction or extension of the adjustable connector. The closed slot may be configured to have a width that is greater than the diameter of the portion of the manifold pin disposed in the slot, so as to facilitate the movement of the adjustable connector. When the assembled manifold is in the collapsed configuration as shown in FIG. 4A, the manifold pin may be aligned with the top of the closed slot 376. When the assembled manifold is in the extended configuration as shown in FIG. 4B, the manifold pin may be aligned with the bottom of the closed slot 376. The bottom of the closed slot 376 provides a hard stop to the extension of the adjustable connector from the housing, preventing the adjustable connector from extending any further. Thus, the closed slot 376 and the manifold pin can prevent the manifold assembly from coming apart.

FIG. 9 shows an exemplary embodiment of a manifold pin 330 of the adjustable height manifold 300 of FIGS. 4A-4B. The manifold pin 330 may comprise a small diameter portion 332 and a large diameter portion 334. The small diameter portion 332 may be configured to engage the closed slot in the adjustable connector, while the large diameter portion 334 may be configured to be disposed in the manifold pin hole in the housing. As described herein, the manifold pin may be coupled to the manifold assembly by inserting the pin through the nut pin hole in the rotating nut. To facilitate the insertion of the manifold pin through the rotating nut, the large diameter portion 334 may have a diameter smaller than the diameter of the nut pin hole. To ensure the retention of the manifold pin within the housing, the large diameter portion 334 may have a diameter that is substantially equal to the diameter of the housing pin hole, such that the large diameter portion press fits into the housing pin hole. To facilitate translational motion of the adjustable connector within the housing channel, the small diameter portion 322 may have a diameter that is smaller than the width of the closed slot of the adjustable connector.

FIG. 10A is a top view and FIG. 10B is a vertical cross sectional view (cross section A-A of FIG. 10A) of the assembled adjustable height manifold 300 in the collapsed configuration, as shown in FIG. 4A. The housing 315 is coupled to the rotating nut 320 via engagement of a lip 357 with a manifold groove 364 of the nut. The adjustable connector 325 is slidably disposed in the housing channel 340, and threadably engaged with the rotating nut 320. The large diameter portion 334 of the manifold pin 330 is disposed in the housing pin hole 360, while the small diameter portion 332 is disposed within the closed slot 376 of the adjustable connector. When the rotating nut is rotated clockwise or counterclockwise, the adjustable connector can slide up or down within the housing channel without rotating. The manifold pin can control the extent to which the adjustable connector may be extended, by providing a hard stop when the pin hits the bottom of the closed slot 376. The inlet 335 of the housing can be coupled to a source of a therapeutic agent to be delivered to the patient. The inlet can be fluidly connected to the housing channel 340 either directly or indirectly through the open slot 374 of the adjustable connector. When the manifold is in a collapsed configuration, the inlet can be fluidly coupled to the housing channel indirectly, through the open slot 374 of the adjustable connector. When the manifold is in an extended configuration, the inlet may be fluidly coupled directly to the housing channel. The housing channel can be fluidly connected to the adjustable connector channel 370, so as to fluidly connect to the stem channel of the first stem, coupled to the first stem connector of the adjustable connector. The housing channel can also be fluidly connected to the stem channel of the second stem, coupled to the second stem connector of the housing. Thus, the therapeutic agent provided via the inlet 335 can be distributed to the first and second intramedullary stems coupled to the manifold.

Fixed Height Wedge

FIGS. 11A-11C show a fixed height wedge 400 suitable for incorporation with a therapeutic agent delivery system for a knee. FIG. 11A shows a perspective view, and FIGS. 11B and 11C show side views of the wedge 400. The fixed height wedge 400 is one example of a coupling member 130 that can couple the two intramedullary stems in a stable configuration, while maintaining a desired distance between the two stems throughout the length of use of the therapeutic agent delivery system in a patient. The wedge provides a relatively simpler connection between two intramedullary stems, wherein the wedge comprises a single, monolithic component rather than an assembly of a plurality of components. While the wedge height 405 of a wedge is fixed, the wedge may be provided in multiple sizes having various wedge heights, and the most appropriate size may be selected for each patient according to the patient's anatomy.

The fixed height wedge 400 comprises a first stem connector 442 configured to couple to a first intramedullary stem, and a second stem connector 444 configured to couple to a second intramedullary stem. The first and second stem connectors may comprise any mechanism for connecting the stem to the coupling member (e.g., flanged region, dovetail joints, snap buckle, winged nut, etc.), as described in further detail herein. The wedge further comprises an inlet 435, configured to be coupled to a source of a therapeutic agent to be delivered to the patient. The inlet 435 can be fluidly connected to a wedge channel 440 extending along the longitudinal axis 410 of the wedge, through both the first stem connector and the second stem connector. Thus, the therapeutic agent provided through the inlet can be distributed via the wedge channel to the intramedullary stems coupled to the wedge.

The fixed height wedge 400 may additionally comprise one or more of any applicable structures and features described in relation to the adjustable height manifold 300. For example, the wedge may comprise a concave groove 445, analogous to the concave groove 345 described in relation to the housing of the adjustable height manifold. Similarly to the concave groove 345, concave groove 445 may be disposed partially about the circumference of the wedge, so as to provide for placement of tubing coupled to the inlet.

Coupling Mechanisms

Figure 12A:
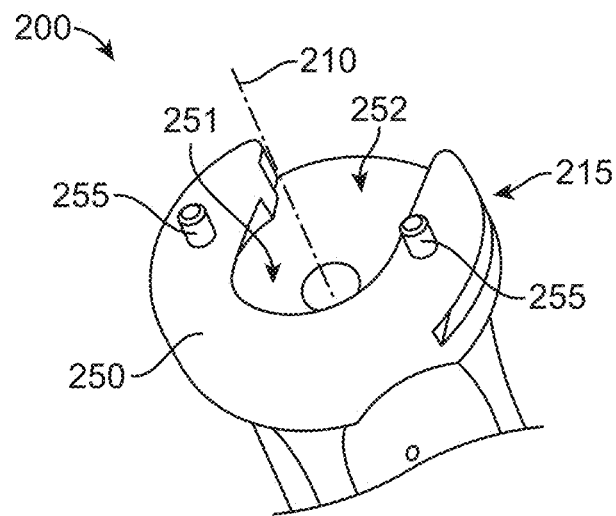
Figure 12B:
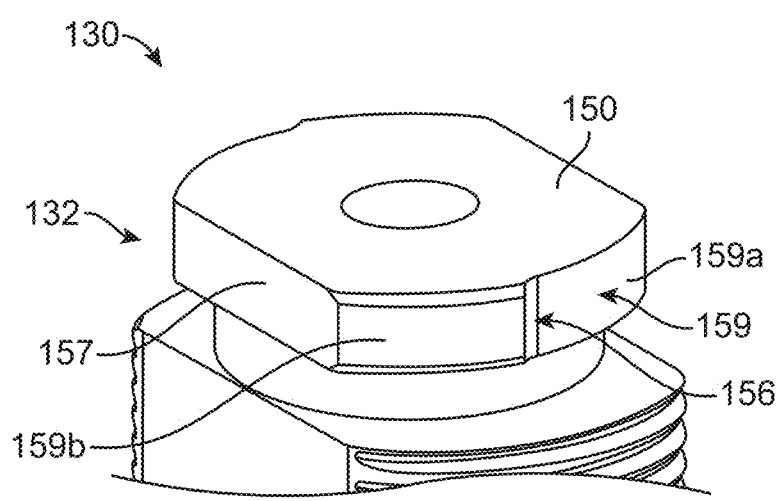
Figures 12E, 12F:
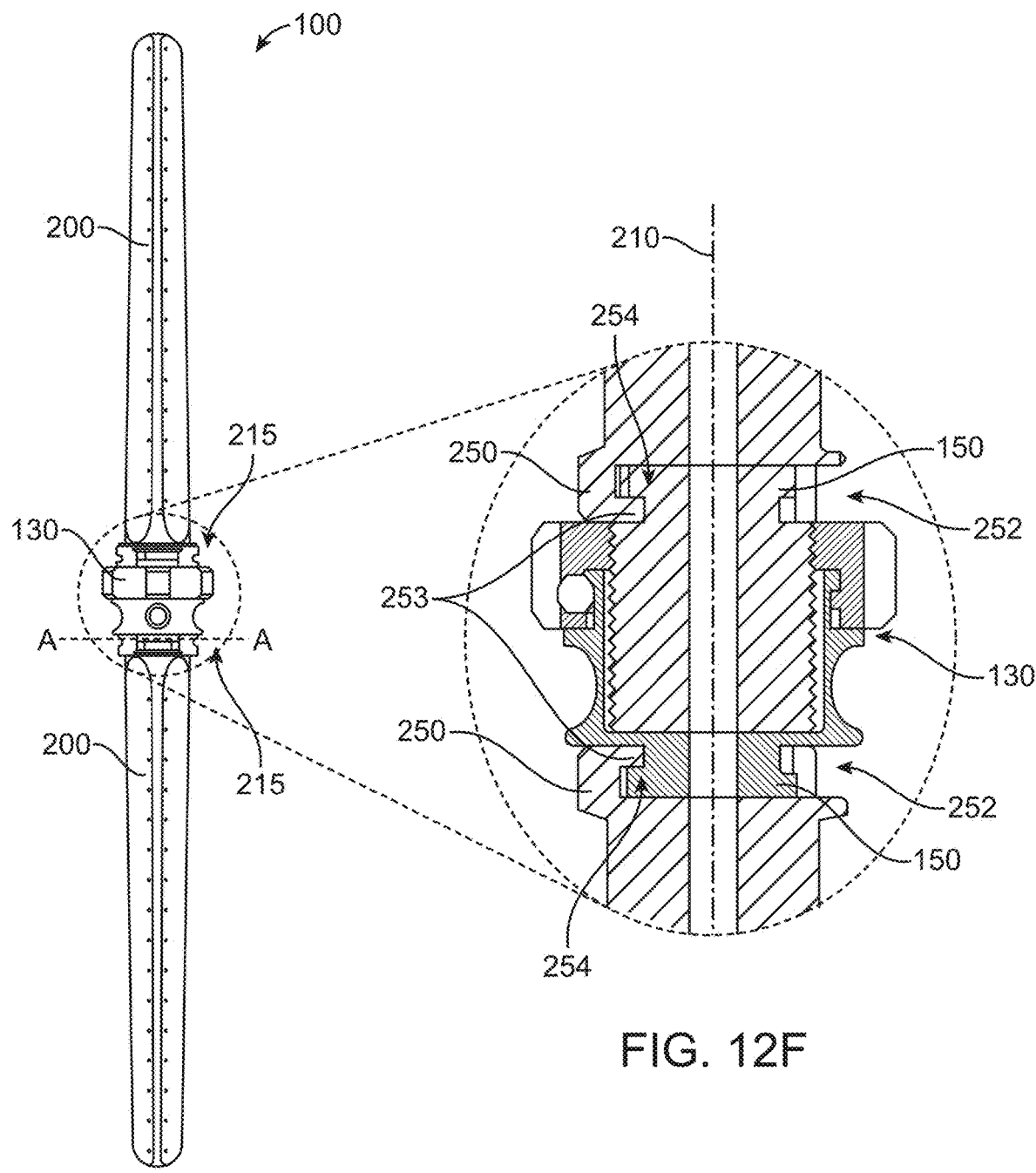
Figure 12G:
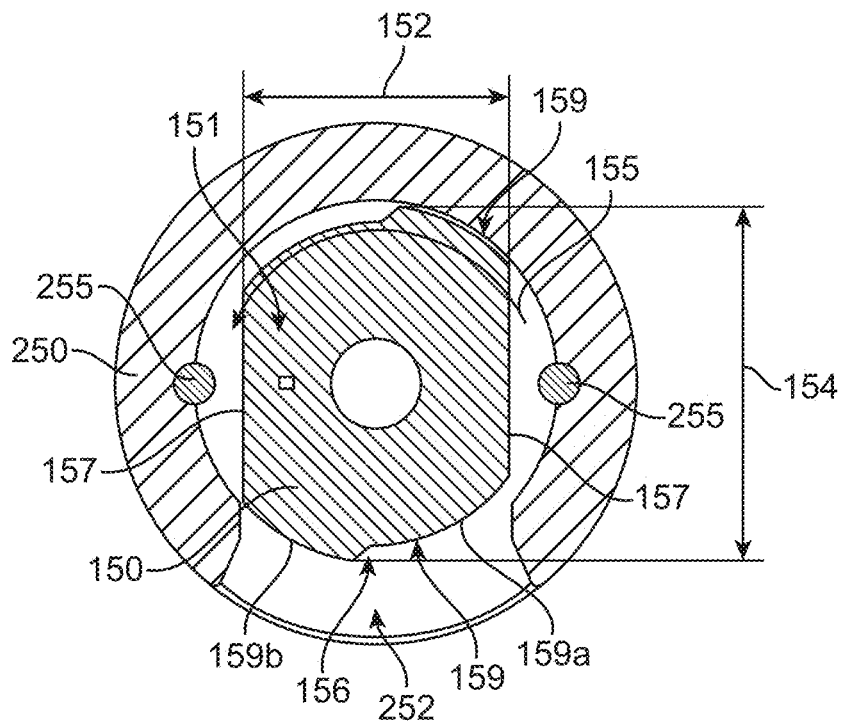
Figure 12H:
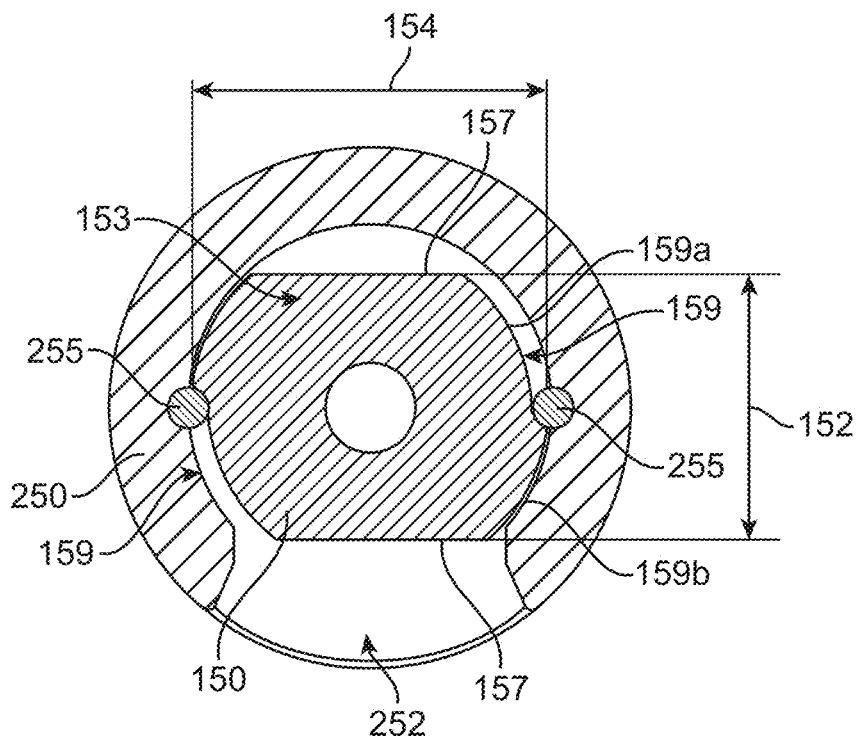

FIGS. 12A-12H illustrate an exemplary mechanism for coupling an intramedullary stem 200 to a coupling member 130. The stem 200 may comprise any embodiment of an intramedullary stem as described herein, and the coupling member 130 may comprise any embodiment of a coupling member as described herein. The stem 200 comprises a first end 215 configured to engage the coupling member, and the coupling member 130 comprises a stem connector 132 configured to engage the first end of the stem. The stem connector 132 may be any stem connector coupled to any coupling member as described (e.g., stem connector 342, 344, 442, 444, etc.). FIG. 12A is a perspective view of the first end 215 of the intramedullary stem 200. FIG. 12B is a perspective view of the stem connector 132 of the coupling member 130. FIGS. 12C and 12D are side views of a therapeutic agent delivery system 100 before assembly. FIG. 12E is a side view of an assembled delivery system 100 comprising two stems 200 and a coupling member 130 coupled together. FIG. 12F is an enlarged vertical cross sectional view of the portion of the assembled system 100 as indicated in FIG. 12C. FIGS. 12G and 12H are radial cross sections of the assembled system 100 along line A-A as indicated in FIG. 12E, at different steps of the assembly.

As shown in FIG. 12A, the first end 215 comprises a raised portion 250 disposed about a portion of the periphery of the first end. The raised portion 250 defines a rounded cavity 251 therein, configured to receive a flanged region 150 of the coupling member 130 as shown in FIG. 12B. The raised portion 250 has a circumferential opening 252 configured to receive the flanged region 150 of the coupling member therethrough. The raised portion 250 further comprises a recessed lip 253 defining a recessed region 254, as best seen in FIG. 12F. The recessed region 254 can receive and retain the flanged region 150, so as to limit axial movement of the coupling member along the longitudinal axis 210 of the stem. As shown in FIGS. 12E and 12F, the flanged region 150 can have a length 154 that is longer than the width 152. The flanged region can further comprise two flat edges 157 extending along the length 154 of the flanged region, and two rounded edges 159 extending about the width 152 of the flanged region. The circumferential opening 252 may have a width that is greater than or equal to the width 152 of the flanged region 150, but less than the length 154 of the flanged region, such that the flanged region can only enter the circumferential opening in the vertical orientation 151 with respect to the circumferential opening 252, as shown in FIG. 12G.

FIGS. 12C and 12D show the delivery system 100 before assembly, wherein the coupling member 130 is aligned for insertion into the space between two intramedullary stems 200. The flanged regions 150 of the first stem connector 132a and second stem connector 132b are in the vertical orientation with respect to the circumferential openings 252 of the raised portions of the intramedullary stems. While aligned in this orientation, the coupling member may be pushed into the space between the two intramedullary stems such that the flanged regions are inserted through the circumferential openings of each stem, and captured into the recessed regions of the raised portions as shown in FIGS. 12E, 12F, and 12G.

Once the flanged region 150 is placed within the rounded cavity 251, the flanged region may be rotated in the direction shown by arrow 155, as shown in FIG. 12G. The flanged region may be rotated until the flanged region is disposed in the horizontal orientation 153 with respect to the circumferential opening 252, as shown in FIG. 12H. In the horizontal orientation, the flanged region can be prevented from sliding out of the rounded cavity through the circumferential opening, since the length 154 of the flanged region is greater than the size of the opening 252. The first end 215 may further comprise one or more pins 255 disposed therein, configured to further secure the coupling between the stem and the stem connection. For example, the first end 215 may comprise two pins 255, each pin angularly spaced at about 90° from the center of the circumferential opening 252. Each rounded edge 159 of the flanged region 150 may comprise a smaller diameter edge 159a and a larger diameter edge 159b, such that a notch 156 is created at the intersection of edges 159a and 159b. As described, the flanged region 150 may be inserted through the opening 252 in the vertical orientation 151 as shown in FIG. 12G, and subsequently rotated in the direction shown by arrow 155, within the recessed region 254 of the first end 215. As the flanged region rotates, the pin 255 can slide against the smaller diameter edge 159a, until the pin hits the notch 156 created by the larger diameter edge 159b. The pins may be configured, for example, to allow the flanged region to rotate by about 90° or a quarter turn before hitting the pins. The engagement of the notch 156 with the pin 255 can prevent further rotation of the stem relative to the coupling member. The pins 255 can thus provide a hard stop to the rotation of the flanged region, ensuring that the final orientation of the flanged region is the horizontal orientation 153, which can prevent the flanged region from sliding out of the rounded cavity as described herein.

Figure 13A:
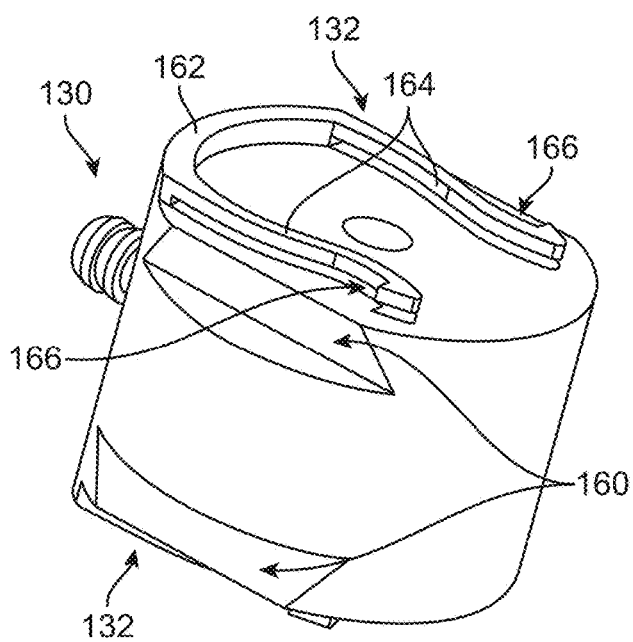
FIGS. 13A-13C illustrate another exemplary mechanism for coupling an intramedullary stem to a coupling member.
Figure 13B:
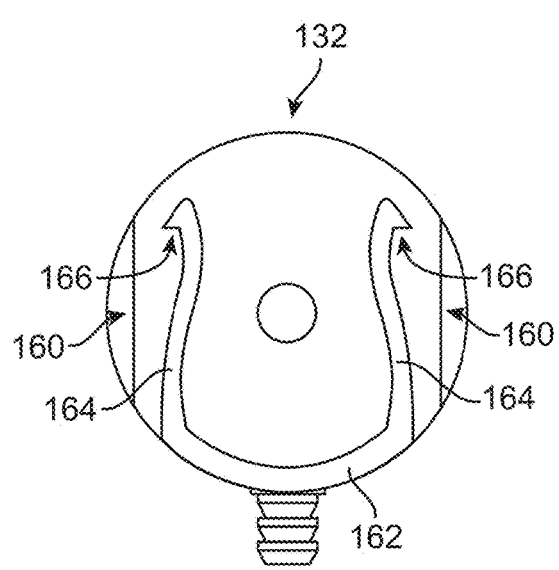
Figure 13C:
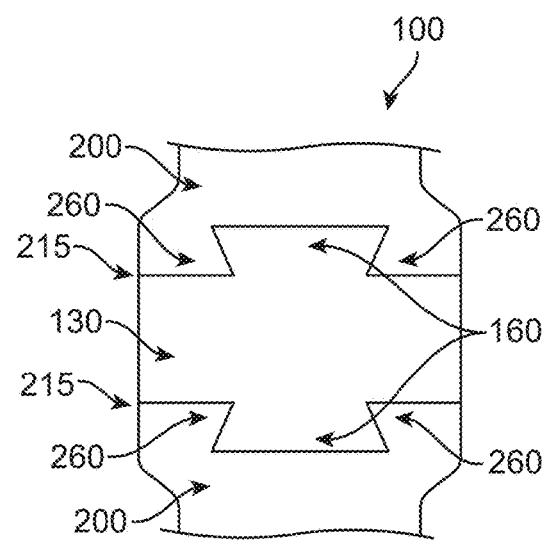

FIGS. 13A-13C illustrate another exemplary mechanism for coupling an intramedullary stem to a coupling member 130. FIG. 13A shows a perspective view and FIG. 13B shows a top view of the coupling member 130 comprising the exemplary connection mechanism. FIG. 13C shows a side view of a portion of an assembled delivery system 100, comprising two stems 200 and a coupling member 130 coupled together. The stem 200 may comprise any embodiment of an intramedullary stem as described herein, and the coupling member 130 may comprise any embodiment of a coupling member as described herein. The stem 200 comprises a first end 215 configured to engage the coupling member, and the coupling member 130 comprises a stem connector 132 configured to engage the first end of the stem. The stem connector 132 may be any stem connector coupled to any coupling member as described (e.g., stem connector 342, 344, 442, 444, etc.). Each stem connector 132 may comprise one or more dovetailed regions 160, configured to engage one or more corresponding dovetailed regions 260 of the first end 215 of the stem 200. Each stem connector 132 may further comprise a snap buckle 162, configured to engage a corresponding snap buckle (not shown) disposed on the first end 215 of the stem. The snap buckle 162 can comprise flexible stems 164 that can tension centrally when the coupling member 130 is inserted slidingly into the stems 200. The coupling member can snap into place when the coupling member is pushed past the notch 166 within the stems.

Figure 14A:
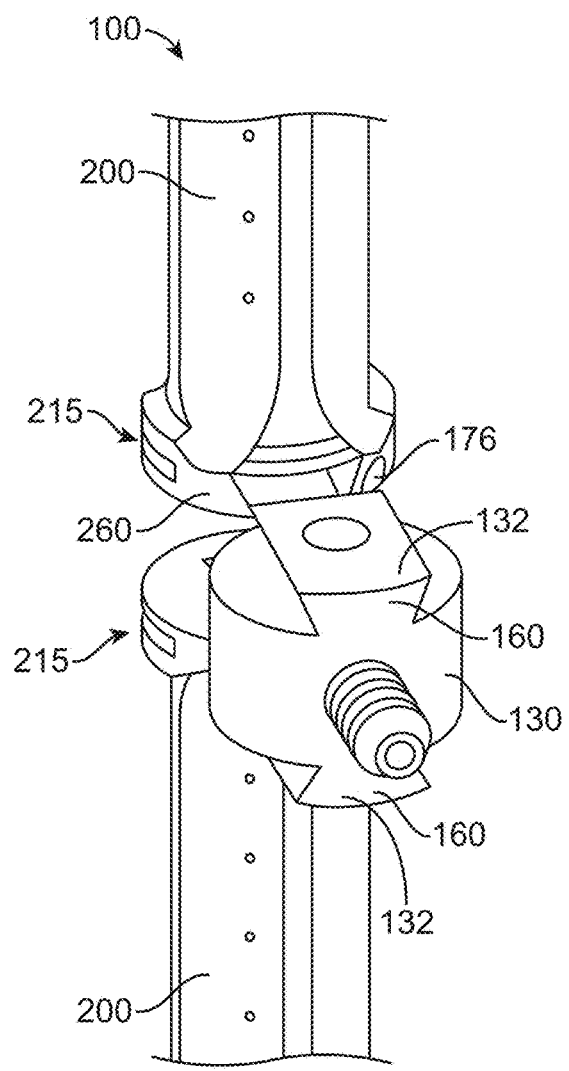
FIGS. 14A-14D illustrate another exemplary mechanism for coupling an intramedullary stem to a coupling member.
Figure 14B:
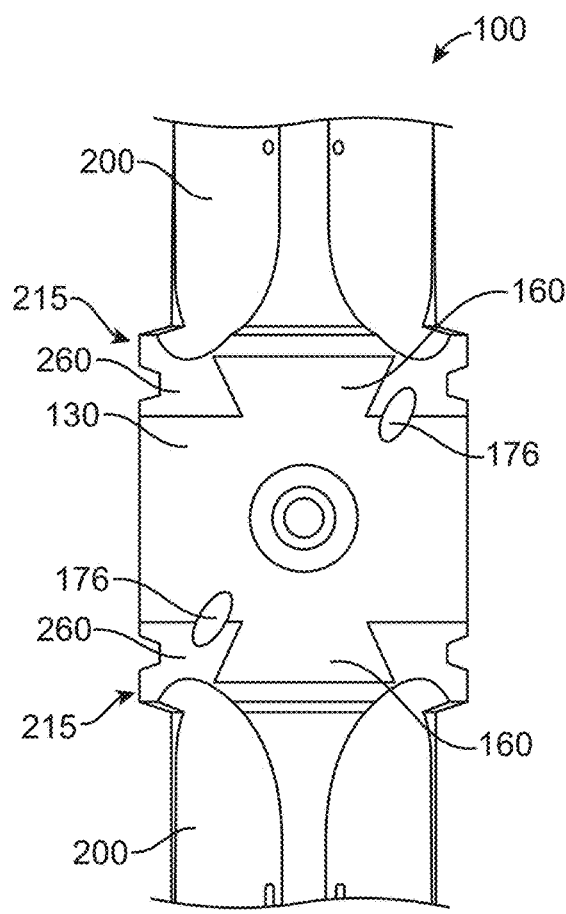

FIGS. 14A and 14B illustrate another exemplary mechanism for coupling an intramedullary stem 200 to a coupling member 130. FIG. 14A shows the first step of assembly of the stems and the coupling member using the exemplary mechanism, and FIG. 14B shows the second step of the assembly. The stem 200 may comprise any embodiment of an intramedullary stem as described herein, and the coupling member 130 may comprise any embodiment of a coupling member as described herein. The stem 200 comprises a first end 215 configured to engage the coupling member, and the coupling member 130 comprises a stem connector 132 configured to engage the first end of the stem. The stem connector 132 may be any stem connector coupled to any coupling member as described (e.g., stem connector 342, 344, 442, 444, etc.). Each stem connector 132 may comprise one or more dovetailed regions 160, configured to engage one or more corresponding dovetailed regions 260 of the first end 215 of the stem 200. FIG. 14A shows the coupling member 130 aligned for insertion into the space between two intramedullary stems 200, wherein the dovetailed regions 160 of the coupling member are aligned with the corresponding dovetailed regions 260 of the stems. The coupling member may be pushed into the space between the two stems such that the dovetailed regions 160 are engaged within the dovetailed regions 260 of the stems. Optionally, the first end 215 of each stem may comprise a raised portion with a circumferential opening similarly as in the embodiment of FIGS. 12A-12H, wherein the dovetailed region 260 is disposed within the rounded cavity defined within the raised portion. In such a configuration, the coupling member may be pushed into the space between the two stems until the dovetailed regions 160 hit a hard stop against the raised portions of the stems. The coupling member 130 or the intramedullary stem 200 may further comprise one or more turn stops 176, configured to hold the coupling member in place once the coupling member is coupled to the stem. FIG. 14B shows the assembled delivery system 100, wherein each stem 200 comprises a turn stop 176 configured to hold the coupling member 130. Each turn stop can be rotatable, such that the position of the turn stop with respect to the stem and the coupling member can be adjusted. During the step of assembly as shown in FIG. 14A, each turn stop may be rotated such that the turn stop does not extend beyond the first end 215 of each stem, thereby allowing the dovetailed region 160 of the coupling member slidingly engage the dovetailed region 260 of the stem without any physical obstruction from the turn stop. Once the coupling member is coupled to the stem, the turn stop may be rotated into the position shown in FIG. 14B, such that the length of the turn stop extends over the junction between the stem and the coupling member. The turn stop can thus prevent the coupling member from sliding out of engagement with the intramedullary stem.

Figure 14C:
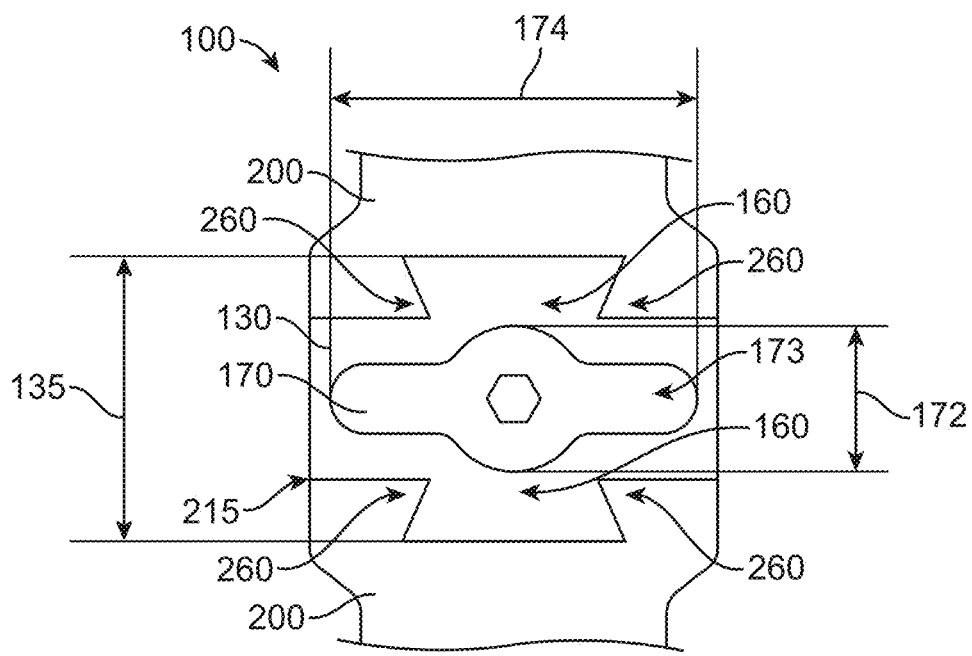
Figure 14D:
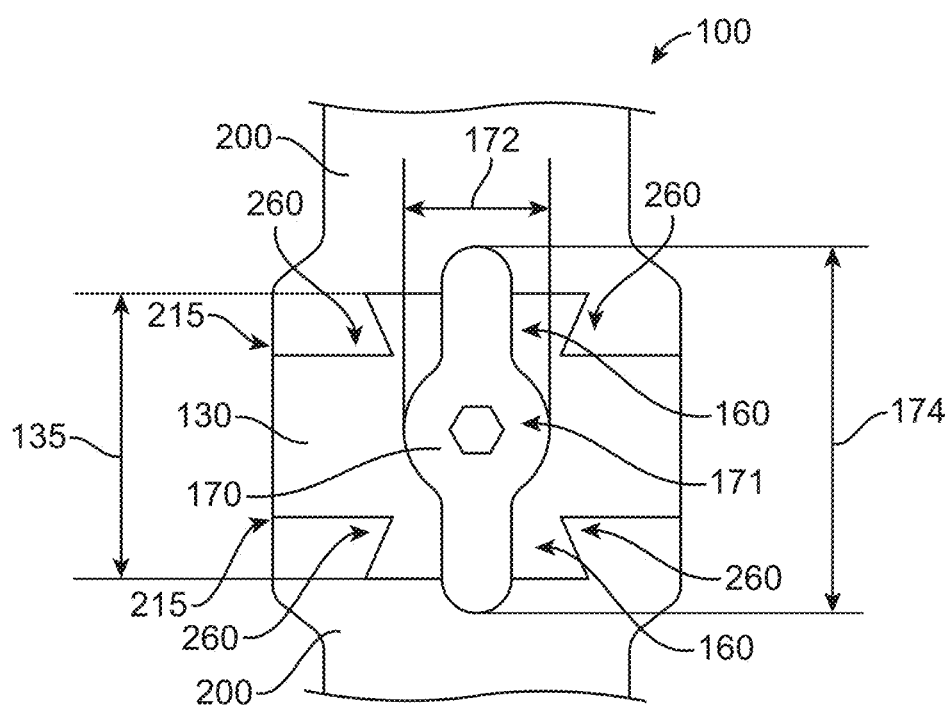

FIGS. 14C and 14D show a variation of the embodiment shown in FIGS. 14A and 14B. Instead of turn stops, the coupling member 130 may comprise a winged nut 170, rotatably fixed onto an anterior portion of the coupling member. The winged nut 170 can be configured to have a length 174 that is greater than the width 172. The length 174 of the nut can be greater than the height 135 of the coupling member. During assembly, the coupling member 130 may be slidingly inserted into the stems 200 with the winged nut 170 in the horizontal orientation 173 as shown in FIG. 14A. Subsequently, the winged nut 170 may be rotated to so as to be in the vertical orientation 171 as shown in FIG. 14B, such that the length 174 of the nut extends over the junction between the dovetailed regions 160 and 260. In the vertical orientation, the winged nut can prevent the coupling member 130 from sliding out of the stems 200.

Method of Use of Therapeutic Agent Delivery System for Knee

Figure 15:
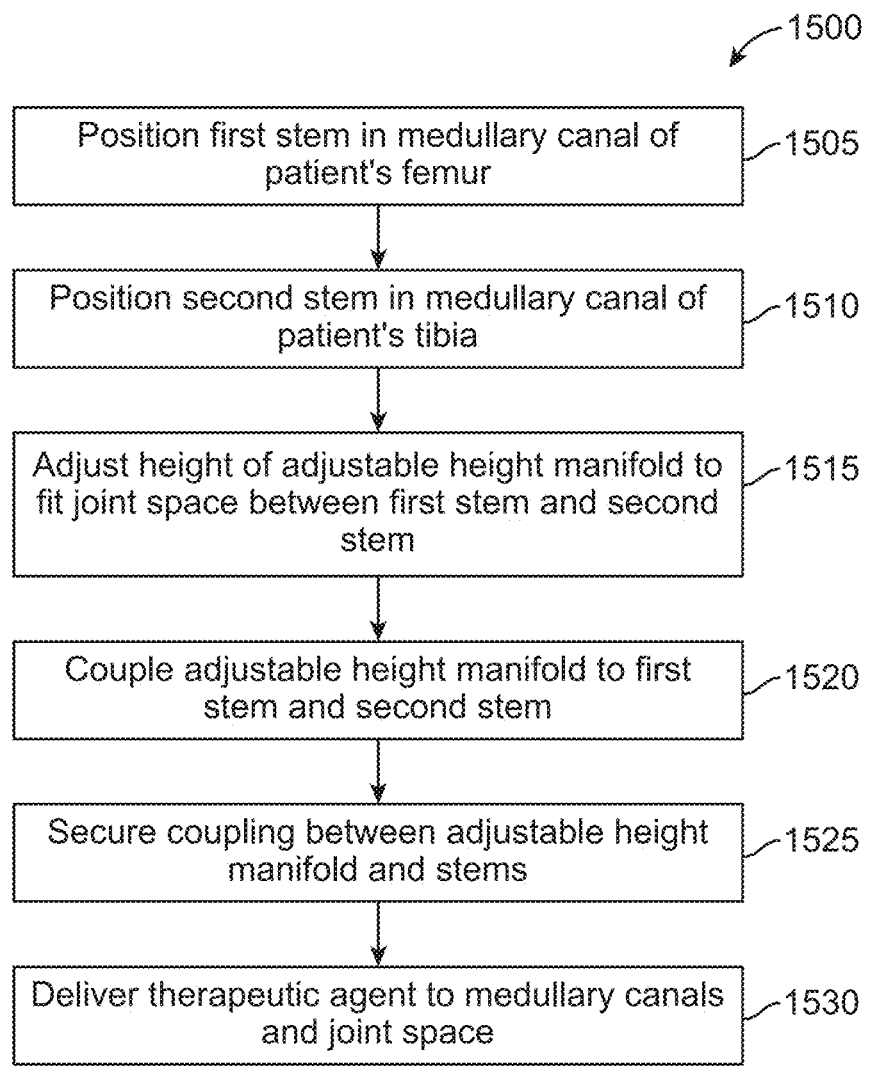
FIG. 15 shows a method of treating a knee with a therapeutic agent delivery system.

FIG. 15 illustrates a method 1500 of treating a patient's knee using the therapeutic agent delivery system for a knee as described herein. In step 1505, a first intramedullary stem is positioned in the medullary canal of the femur of the patient. In step 1510, a second intramedullary stem is positioned in the medullary canal of the tibia of the patient. In step 1515, the height of an adjustable height manifold is adjusted to fit the joint space between the first stem and the second stem. In step 1520, the adjustable height manifold is coupled to the first stem and the second stem. The adjustable height manifold may be inserted in the joint space between the first stem and the second stem in a specific orientation appropriate for the connection mechanism used. For example, if the adjustable height manifold comprises stem connections with flanged regions as described herein, configured to engage corresponding rounded cavities of the stems, the adjustable height manifold may be inserted by leading with the two rounded edges of the flanged region. In step 1525, the coupling between the adjustable height manifold and the first and second stems is further secured, via appropriate steps for the connection mechanism used. For example, if the adjustable height manifold comprises the flanged region as described herein, the manifold may be rotated to securely engage the flanged region into the corresponding cavity of the stems. If the adjustable height manifold and the stems comprise dovetailed regions with turn stops as described herein, the turn stops may be rotated to extend over the junction between the stem and the manifold, so as to prevent de-coupling of the manifold from the stems. In step 1530, the therapeutic agent is delivered to the medullary canals of the femur and the tibia and the joint space.

Figure 16:
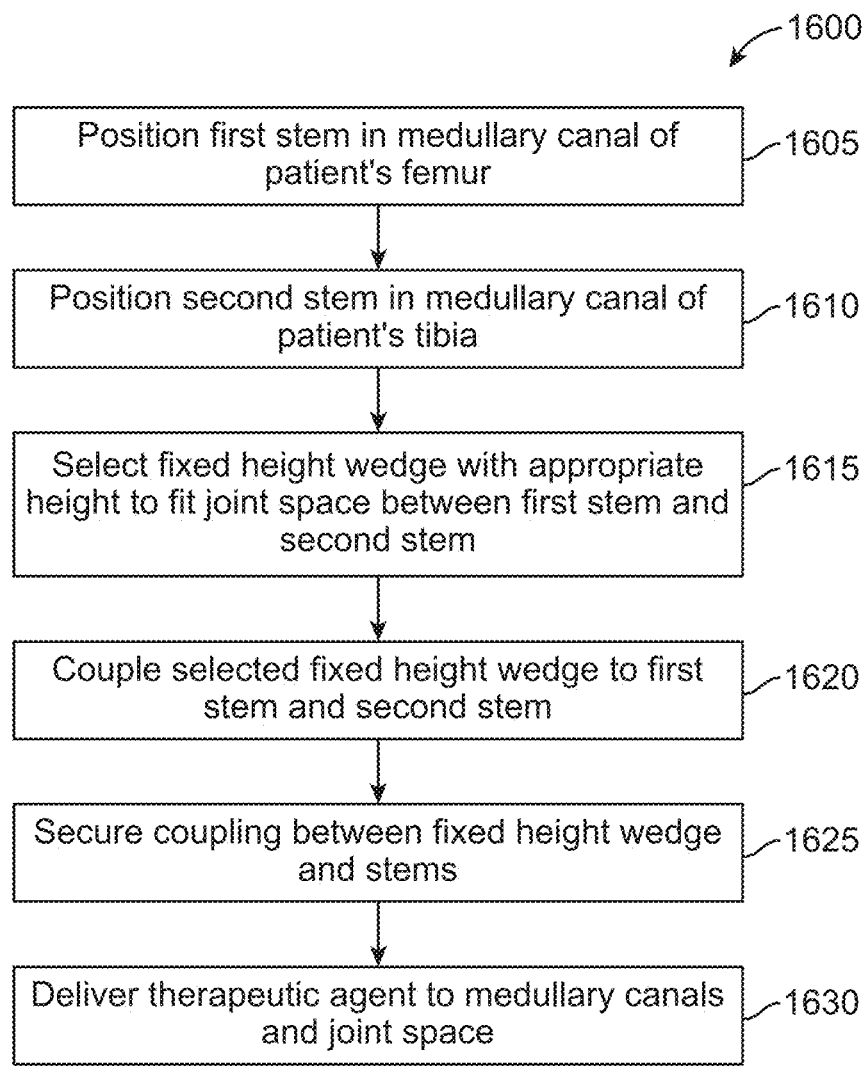
FIG. 16 shows a method of treating a knee with a therapeutic agent delivery system.

FIG. 16 illustrates a method 1600 of treating a patient's knee using the therapeutic agent delivery system for a knee as described herein. In step 1605, a first intramedullary stem is positioned in the medullary canal of the femur of the patient. In step 1610, a second intramedullary stem is positioned in the medullary canal of the tibia of the patient. In step 1615, a fixed height wedge with an appropriate height to fit the joint space between the first stem and the second stem is selected. In step 1620, the fixed height wedge is coupled to the first stem and the second stem, wherein the fixed height wedge may be inserted into the joint space between the first and second stems in a specific orientation appropriate for the connection mechanism used. For example, if the fixed height wedge comprises stem connections with flanged regions as described herein, configured to engage corresponding rounded cavities of the stems, the fixed height wedge may be inserted by leading with the two rounded edges of the flanged region. In step 1625, the coupling between the fixed height wedge and the first and second stems is further secured, via appropriate steps for the connection mechanism used. For example, if the fixed height wedge comprises the flanged region as described herein, the fixed height wedge may be rotated to securely engage the flanged region into the corresponding cavity of the stems. If the fixed height wedge and the stems comprise dovetailed regions with turn stops as described herein, the turn stops may be rotated to extend over the junction between the stem and the fixed height wedge, so as to prevent de-coupling of the fixed height wedge from the stems. In step 1630, the therapeutic agent is delivered to the medullary canals of the femur and the tibia and the joint space.

The steps of methods 1500 and 1600 are provided as examples of methods of using a therapeutic agent delivery system in accordance with embodiments. A person of ordinary skill in the art will recognize many variations and modifications of methods 1500 and 1600 based on the disclosure provided herein. For example, some steps may be added or removed. One or more steps may be performed in a different order than as illustrated in FIGS. 15 and 16. Some of the steps may comprise sub-steps. Many of the steps may be repeated as many times as appropriate or necessary.

Therapeutic Agent Delivery System for Hip

FIGS. 17A and 17B show an exemplary therapeutic agent delivery system 500 for a hip. FIG. 17A is a perspective view of the assembled delivery system, while FIG. 17B is an exploded perspective view of the system. The delivery system 500 comprises a femoral stem 510 and a femoral head 520. The femoral stem 510 can be configured to disposed in a femoral medullary canal of a patient. The femoral head 520 can be configured to be disposed in an acetabulum of the patient. The femoral stem may comprise an inlet 535 configured to couple to a source of a therapeutic agent to be delivered to the patient. The inlet can be fluidly coupled to a channel in the femoral stem, so as to allow the therapeutic agent to be distributed in the femoral medullary canal. The femoral stem and the femoral head may be configured to removably couple together so as to fluidly connect the femoral stem channel to one or more channels in the femoral head, such that the therapeutic agent can also be distributed in the acetabular joint space. The femoral stem and the femoral head may be configured to couple in a stable configuration, so as to maintain a desired distance between the femoral stem and the femoral head through the length of use of the therapeutic agent delivery system in the patient. Optionally, the femoral stem and the femoral head may be connected in a fashion that allows the distance between the stem and the head to be adjusted to fit the anatomy of the patient. The system 500 may further comprise a stem plug 530, configured to couple to an end of the femoral stem.

Femoral Stem

FIGS. 18A-18D show an exemplary femoral stem 600 suitable for incorporation with a therapeutic agent delivery system for a hip. FIG. 18A is a perspective view, FIG. 18B is a side view, FIG. 18C is a bottom view, and FIG. 18D is a side cross-sectional view of the femoral stem 600. The femoral stem 600 comprises an elongate body 605 having a longitudinal axis 610, the elongate body having a first end 615 and a second end 620 opposite the first end. The elongate body comprises a neck region 650 disposed near the first end 615, wherein the neck region may be configured to couple to the femoral head. The second end 620 may be configured be disposed in the femoral medullary canal. The femoral stem 600 further comprises an inlet 535, configured to be coupled to a source of the therapeutic agent. The inlet 535 is in fluid communication with a stem channel 625 extending between the first end 615 and the second end 620, as best seen in FIG. 18D. The stem channel can be configured to deliver the therapeutic agent through the stem and to the medullary canal. Further, the stem channel can be configured to fluidly couple to one or more channels in the femoral head.

The elongate body 605 may have one or more structures or features that are similar to the intramedullary stem 200 described previously. For example, the femoral stem 600 may comprise a plurality of protrusions 630, protruding radially outward from the elongate body 605. The plurality of protrusions may comprise any number of protrusions having any appropriate shape, size, or configuration to engage the medullary canal in a stable fashion. For example, the protrusions may comprise elongate fins extending along the longitudinal length of the elongate body, as shown in FIGS. 18A-18D. In one exemplary embodiment, the plurality of protrusions may comprise four fins, spaced equally at about 90° about the longitudinal axis 610 of the elongate body. Of course this is not intended to be limiting, and the number of fins may be any number, such as three fins spaced approximately 120 degrees apart, five fins spaced approximately 72 degrees apart, etc. The plurality of protrusions 630 and the elongate body 605 may be formed separately and coupled together. Alternatively or in combination, the plurality of protrusions 630 may be formed by removing material from the elongate body 605, such that the plurality of protrusions and the elongate body are formed as a single member. Adjacent protrusions 630 may define one or more fluted regions 635 therebetween, the fluted regions radially recessed compared to the protrusions.

The plurality of protrusions and fluted regions can be configured to minimize the surface area of the stem contacting the bone lining the medullary canal, such that the area of the bone flushed with the therapeutic agent may be maximized. For example, the plurality of protrusions and fluted regions can be configured such that less than 50% of the surface area of the stem is in contact with the bone lining the medullary canal. Of course this is not intended to be limiting and one of skill in the art will appreciate that any percentage of surface area of the stem may contact the bone. The stem may comprise a plurality of identical fluted regions defined by a plurality of elongate fins, distributed symmetrically about the longitudinal axis 610 of the stem, as shown in FIGS. 18A-18D. Alternatively, a plurality of fluted regions may be distributed asymmetrically about the longitudinal axis of the stem, and/or may have different shapes or sizes. For example, the elongate body 605 may comprise protrusions and fluted regions as described in relation to FIGS. 3A and 3B.

The femoral stem 600 may further comprise a plurality of outlet holes 640 in fluid communication with the stem channel 625. The plurality of outlet holes 640 may be configured to deliver the therapeutic agent, distributed through the stem channel 625, to the femoral medullary canal, as well as adjacent tissue including the joint. The plurality of outlet holes may be disposed in a fluted region 635, so as to deliver the therapeutic agent to the area of the bone not in contact with the femoral stem. The plurality of outlet holes may comprise any number of outlet holes having any appropriate size, shape, or distribution. For example, the plurality of outlet holes may include a plurality of equally sized and spaced holes that extend axially along a line substantially parallel to the longitudinal axis 610 of the stem, as shown in FIGS. 18A-18D. Alternatively, the plurality of outlet holes may extend along a helical or spiral line as shown in FIG. 3A, or the holes may extend about a plurality of rings around the circumference of the elongate body, as shown in FIG. 3B. The plurality of outlet holes may comprise holes having an identical shape and/or size, or holes having various shapes and/or sizes. Varying the hole size may allow further fluid control of therapeutic agent as it exits different regions of the stem.

The stem channel 625 may be a through hole that extends from the first end 615 to the second end 620 through both the first end and the second end, such that the elongate body comprises an open second or distal end. The system may further comprise a plug, shown in FIG. 19, configured to couple to the open second end of the stem, so as to close the second end and thereby create a blind channel. Alternatively, the stem channel 625 may be a blind channel, wherein the second end of the elongate body is closed. In configurations wherein the second end is open, the therapeutic agent may exit the stem channel into the medullary canal through the second end and/or through a plurality of outlet holes disposed along the elongate body 605 as described herein. If the stem comprises only the stem channel 625 extending through the first and second ends, without the plurality of outlet holes, the therapeutic agent may exit the stem channel only through the second end. In configurations wherein the second end of the stem is closed, the therapeutic agent may exit the stem channel into the medullary canal only through the plurality of outlet holes.

The neck region 650 extends along a neck axis 655, disposed at an angle 660 with respect to the longitudinal axis 610 of the elongate body 605. The angle 660 may be in a range from about 120° to about 160°, about 130° to about 150°, about 140° to about 150°, or about 145°. The neck region may comprise one or more connection mechanisms or features to couple to the femoral head. For example, as shown, the neck region may comprise a plurality of threads 670, configured to threadably engage complementary threads on the femoral head.

The femoral stem 600 may be tapered to fit the medullary canal. For example, the elongate body 605 and/or the plurality of protrusions 630 may be tapered from the first end 615 to the second end 620, as shown, so as to have a smaller radial cross-sectional area at the second end than at the first end. For example, the taper may comprise a gradual taper, wherein the extent of the taper may be in a range from about 0.1° to about 10°, about 0.5° to about 5°, about 1° to about 5°, about 1° to about 4°, or about 2° or about 3°. The taper may be adjusted to accommodate a medullary canal of a specific type of bone.

FIG. 19 shows a stem plug 530 suitable for incorporation with any therapeutic agent delivery system as described herein. The stem plug 530 may comprise a smaller diameter region 535 and a larger diameter region 540. The smaller diameter region may be configured to be press-fit into an open second end of an elongate body of any intramedullary stem or hip stem as described herein.

Femoral Head

Figure 20A:
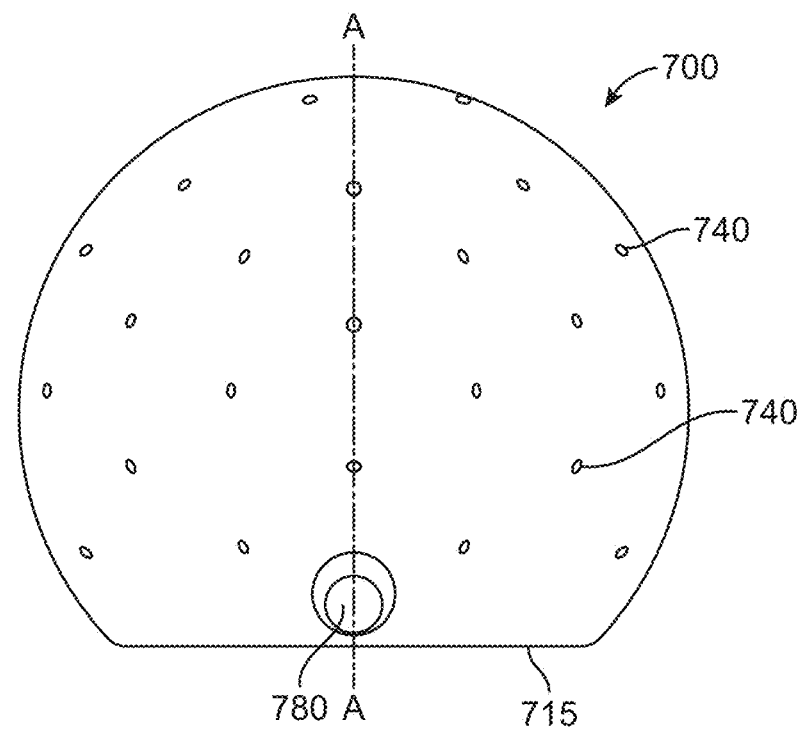
FIG. 20A is a side view of an exemplary embodiment of a femoral head.
Figure 20B:
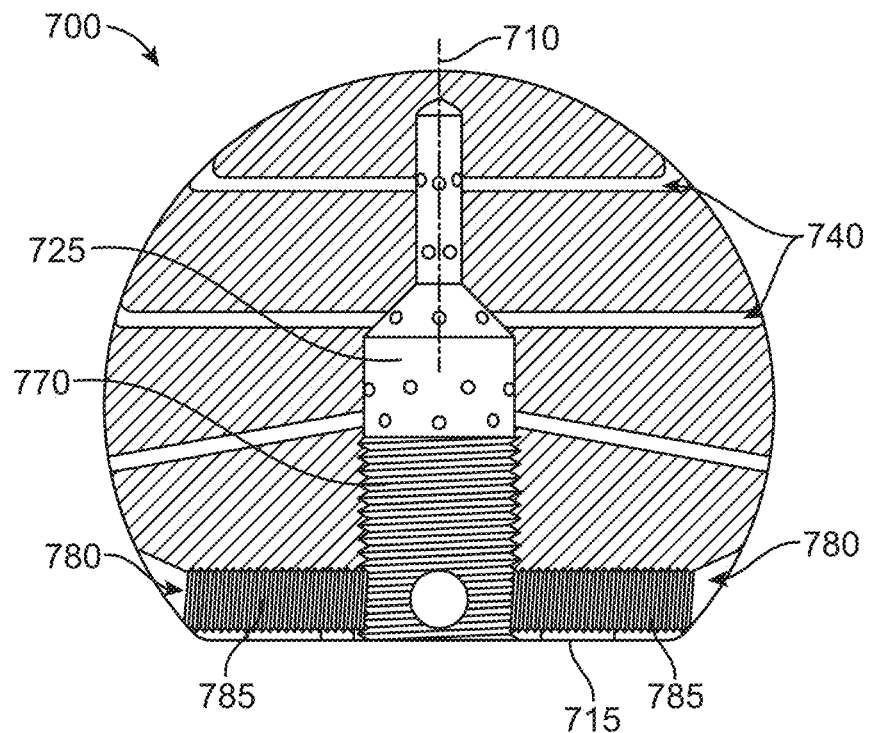
FIG. 20B is a side cross-sectional view of the femoral head of FIG. 20A.

FIGS. 20A and 20B show an exemplary embodiment of a femoral head 700, suitable for incorporation with a therapeutic agent delivery system for a hip. FIG. 20A is a side view, and FIG. 20B is a side cross-sectional view of the femoral head 700, along line A-A as shown in FIG. 20A. The femoral head 700 can comprise the shape of a truncated sphere, wherein the truncated base 715 of the head is configured to couple to the femoral stem. The femoral head 700 comprises a head central channel 725, extending axially along a central axis 710 of the femoral head. The central channel 725 is configured couple to the neck of the femoral stem, and thereby be in fluid communication with the hip stem channel when the femoral head is connected to the femoral stem. The femoral head further comprises a plurality of outlet holes 740, fluidly coupled to the central channel 725. The outlet holes may be configured to extend radially outwards from the central channel. Thus, a therapeutic agent may be supplied to the delivery system via an inlet of the femoral stem, move through the stem channel into the central channel 725 of the femoral head, and exit into the acetabular joint space through the outlet holes 740.

The base 715 may comprise one or more mechanisms for coupling the femoral head to the neck region of the femoral stem. For example, as shown, a portion of the central channel 725 near the base 715 may comprise a plurality of threads 770, configured to threadably engage a plurality of complementary threads of the femoral stem neck. A threaded connection between the femoral head and the femoral stem neck can allow the distance between the femoral head and the femoral stem to be adjusted to fit the patient's anatomy. Optionally, the femoral head may be further configured to receive one or more set screws near the base, wherein the set screws can fix the distance between the femoral head and the femoral stem once the distance is appropriately set. For example, as shown in FIG. 20B, the base may comprise two set screw receiving regions 780, wherein each set screw receiving region comprises a plurality of threads 785 to engage a set screw having complementary threads. The set screw receiving regions can extend radially outwards from the central channel, such that the ends of the set screws can be directly or indirectly coupled to the neck of the femoral stem disposed within the central channel. While FIG. 20B shows two set screw receiving regions radially offset from one another by about 180°, the femoral head may comprise any number of set screws distributed in any appropriate configuration. For example, the femoral head may comprise three set screw receiving regions radially offset from one another by about 120°, or four set screw receiving regions radially offset from one another by about 90°.

Figure 21A:
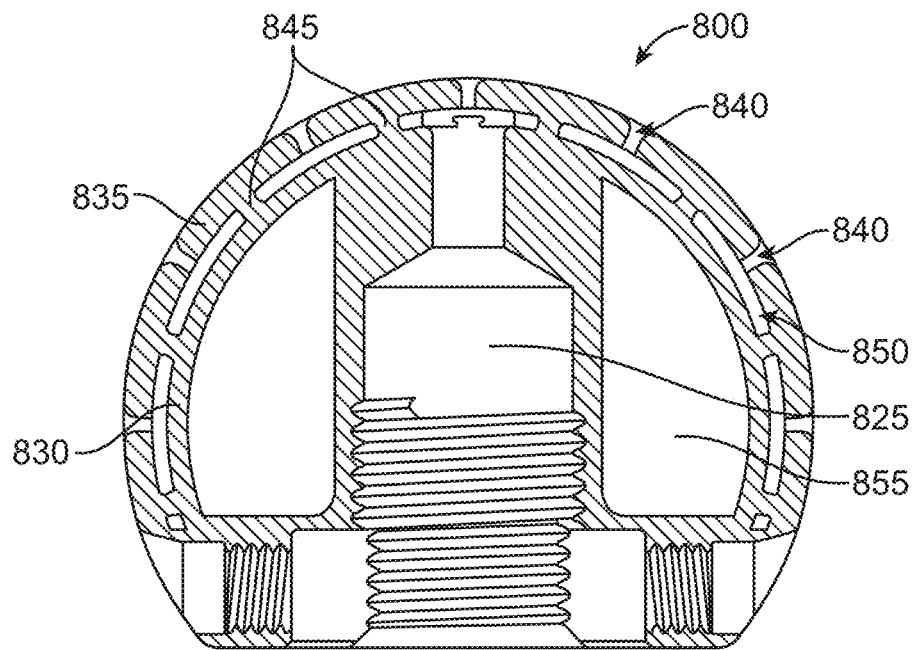
FIGS. 21A and 21B are side cross-sectional views of another exemplary embodiment of a femoral head.
Figure 21B:
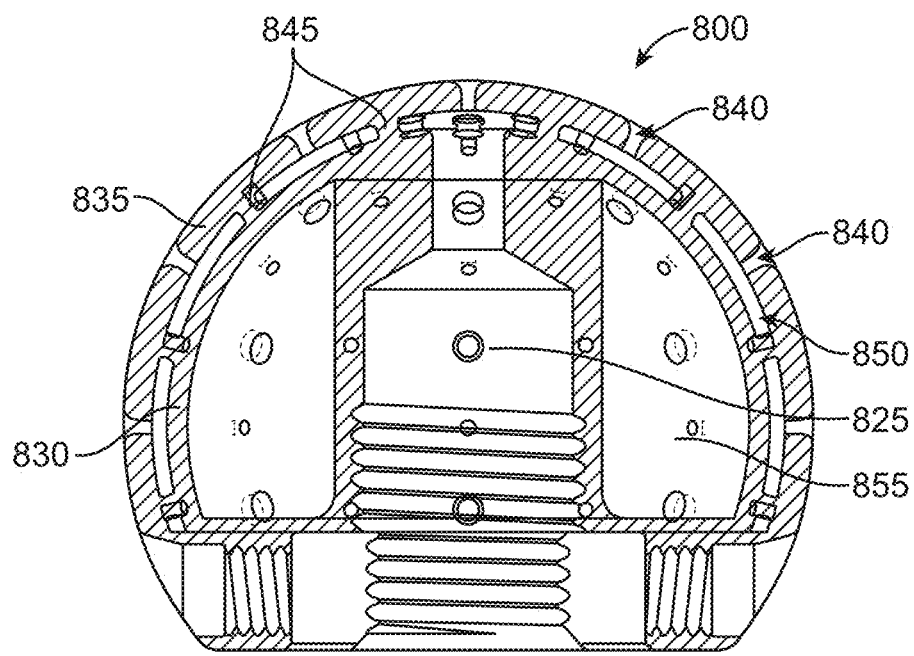

FIGS. 21A and 21B show another exemplary embodiment of a femoral head 800, suitable for incorporation with a therapeutic agent delivery system 500 for a hip. The femoral head 800 is partially hollowed, so as to reduce the material mass and weight of the femoral head. The femoral head 800 comprises a central channel 825, configured to be in fluid communication with the stem channel of the femoral stem as described herein. The femoral head further comprises an inner shell 830 and an outer shell 835, wherein the inner and outer shells are thin, truncated spherical shells disposed about the periphery of the femoral head. The inner shell 830 is connected to the material disposed about and defining the central channel 825. The outer shell 835 is connected to the inner shell 830 via a plurality of support struts 845 extending between the inner shell and the outer shell. The inner shell defines an inner cavity 855 between the inner shell and the material defining the central channel. The inner cavity 855 is hollow, and configured to be sealed against the central channel and the inner shell, such that no fluid can enter the inner cavity during use of the delivery system. The inner shell and the outer shell define an outer cavity 850 therebetween, wherein the outer cavity 850 is fluidly coupled to the central channel 825. The outer shell comprises a plurality of outlet holes 840, such that fluid in the outer cavity 850 can exit the femoral head through the outlet holes. Thus, the therapeutic agent supplied through an inlet of a femoral stem can move through the stem channel into the central channel 825 of the femoral head 800, into the outer cavity 850, and through the outlet holes 840 into the acetabular joint space. Components of the femoral head 800 may be formed via 3D printing or laser sintering.

Figure 22:
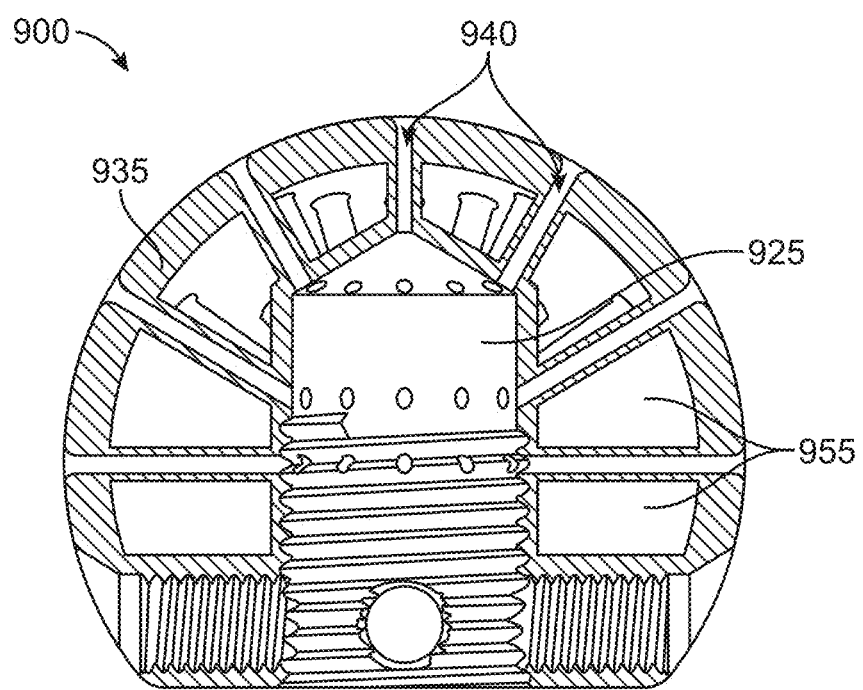
FIG. 22 is a side cross-sectional view of another exemplary embodiment of a femoral head.

FIG. 22 shows another exemplary embodiment of a femoral head 900, suitable for incorporation with a therapeutic agent delivery system for a hip. The femoral head 900 comprises a central channel 925, configured to be in fluid communication with the stem channel of the femoral stem as described herein. The femoral head further comprises a plurality of hollow tubes 940 extending radially outwards from the central channel 925 and fluidly coupled to the central channel. The femoral head further comprises an outer shell 935, a thin, truncated spherical shell disposed about the periphery of the femoral head. The outer shell 935 is coupled to the plurality of hollow tubes 940, such that the hollow tubes 940 extend through the thickness of the outer shell. The hollow tubes, the outer shell, and the material disposed about defining the central channel together define a plurality of inner cavities 855, which are hollow and configured to be fluidly sealed, such that no fluid can enter the inner cavities during use of the delivery system. Thus, the therapeutic agent supplied through an inlet of a femoral stem can move through the stem channel into the central channel 925 of the femoral head 900, into the plurality of hollow tubes 940, and into the acetabular joint space. The internal diameter of the hollow tubes and/or the thickness of the hollow tubes may be varied to control the flow of fluid within the femoral head, and to adjust the amount of support provided by the hollow tubes to the outer shell to protect the integrity of the outer shell.

Coupling Mechanisms

Figure 23A:
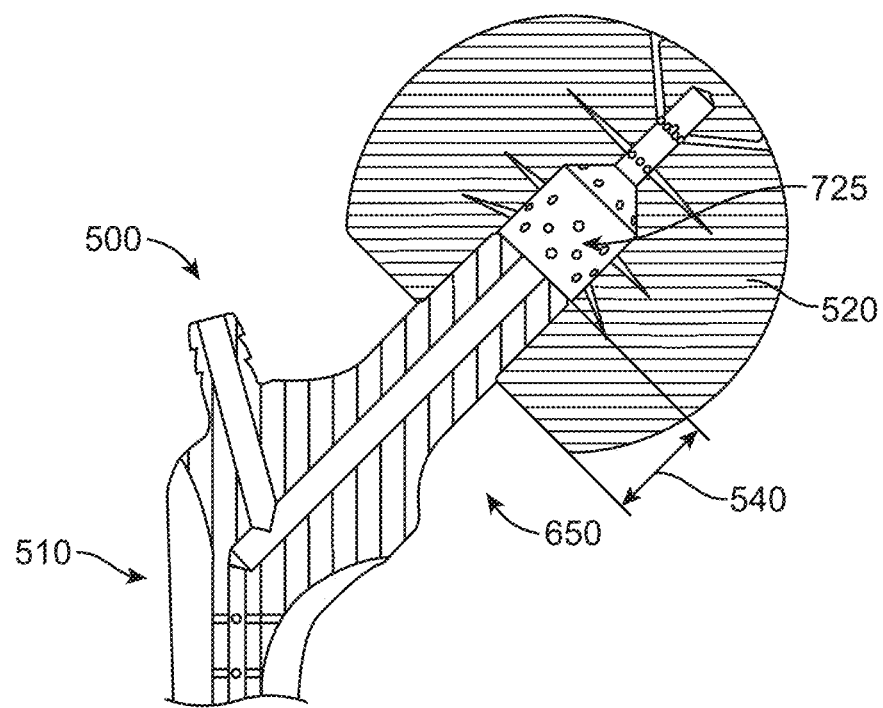
FIGS. 23A and 23B show exemplary mechanisms for coupling a femoral head to a femoral stem.
Figure 23B:
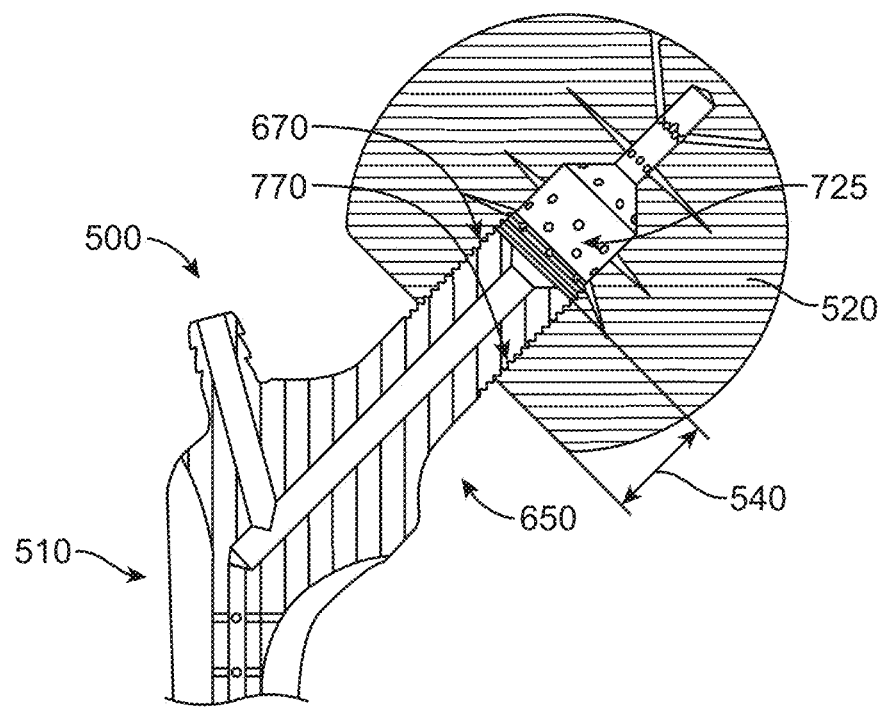

FIGS. 23A and 23B show exemplary mechanisms for coupling a femoral head 520 to a femoral stem 510. The femoral head 520 may comprise any femoral head as described herein, such as femoral heads 700, 800, and 900 described in relation to FIGS. 20A-22. The femoral stem 510 may comprise any femoral stem as described herein, such as any embodiment of the femoral stem 600 described herein. FIG. 23A is a side cross sectional view of a femoral head 520 coupled fixedly to a femoral stem 510. The neck region 650 of the stem is fixedly coupled to a portion of the central channel 725 of the femoral head, such that the length 540 of the neck that engages the femoral head is fixed. For example, the neck 650 may be press-fitted into the central channel 725, such that the neck advances into the central channel by a pre-determined length. The neck 650 may comprise regions having different diameters so as to create a notch between the regions, wherein the notch can provide a stop against the femoral head surface when the neck 650 has been advanced into the central channel by the pre-determined length. In a delivery system incorporating such a connection mechanism, the distance between the femoral head and the femoral stem is fixed. FIG. 23B is a side cross sectional view of a femoral head 520 coupled adjustably to a femoral stem 510. The neck region 650 of the stem is adjustably coupled to a portion of the central channel 725, for example via engagement of threads 670 disposed on the neck 650 of the stem with complementary threads 770 disposed on a portion of the central channel 725. The length 540 of the neck that engages the central channel can thereby be increased or decreased by threadably rotating the femoral head about the femoral stem. As the femoral head is rotated to axially translate the head farther away from the femoral stem, the length 540 decreases, and the distance between the femoral head and the femoral stem increases such that the delivery system can be suitable for patients requiring a longer set distance between the femur and the acetabulum. As the femoral head is rotated to axially translate the head closer to the femoral stem, the length 540 increases, and the distance between the femoral head and the femoral stem decreases such that the delivery system can be suitable for patients requiring a shorter set distance between the femur and the acetabulum. In a delivery system incorporating such a connection mechanism, the distance between the femoral head and the femoral stem can be thus adjusted to accommodate the anatomy of a patient.

Figure 24A:
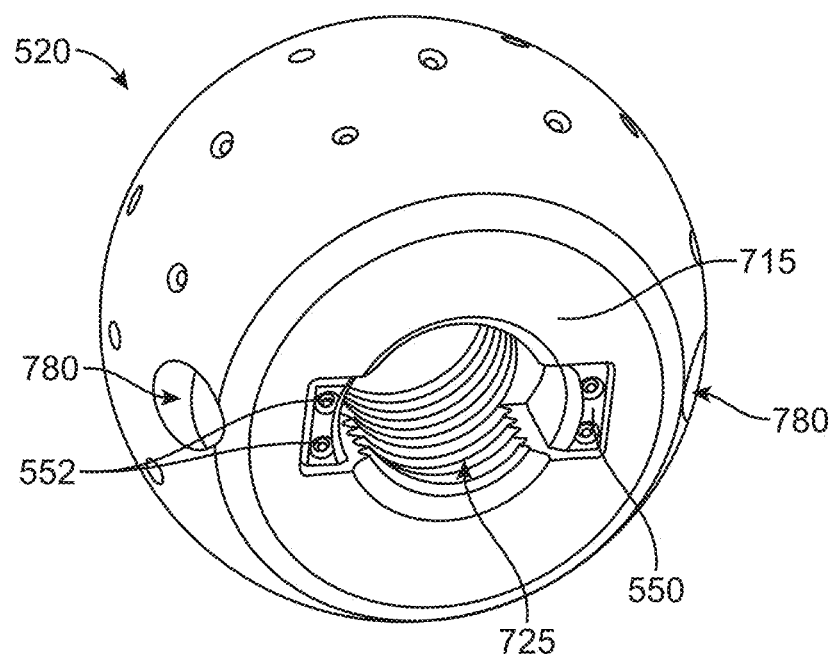
FIGS. 24A and 24B show an exemplary mechanism for locking a set distance between a femoral head and a femoral stem.
Figure 24B:
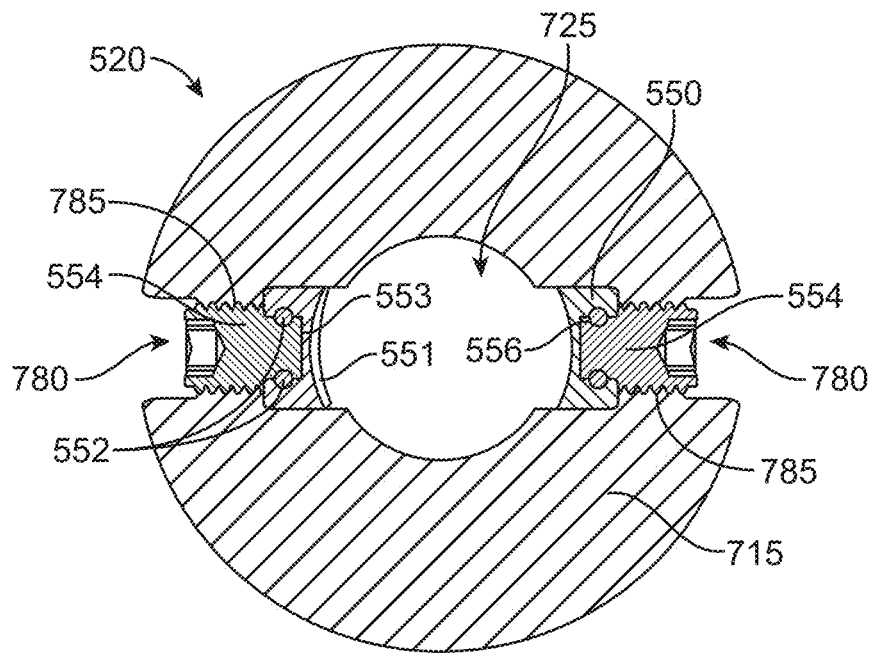

FIGS. 24A and 24B show an exemplary mechanism for locking a set distance between a femoral head 520 and a femoral stem 510 of a therapeutic agent delivery system for a hip. The femoral head 520 may comprise any femoral head as described herein, such as femoral heads 700, 800, and 900 described in relation to FIGS. 20A-22. The femoral stem 510 may comprise any femoral stem as described herein, such as any embodiment of the femoral stem 600 described herein. FIG. 24A is a perspective view and FIG. 24B is a bottom view of a femoral head 520 comprising the exemplary mechanism. As described herein, a femoral head 520 may comprise a pair of set screw receiving regions 780 near the base 715 of the head, which can receive a pair of set screws configured to engage the femoral stem neck disposed in the central channel 725 of the femoral head, so as to fix the position of the stem neck therein. The femoral head may further comprise a pair of blocks 550 disposed within the set screw receiving regions 780, adjacent to the central channel 725. Each block can be coupled with a set screw 554, wherein the block may comprise a rounded cavity to receive the end of the set screw, and wherein the end of the set screw may be free to rotate within the rounded cavity. Two dowel pins 552 may be coupled to the block-set screw assembly so as to limit the translational motion of the set screw relative to the block. Rotation of the set screw within the set screw receiving region can cause the block coupled thereto to translate radially inwards or outwards. The block may be translated radially inwards until the block engages and pushes against the neck region of the stem disposed within the central channel, thereby preventing further rotation of the femoral head about the femoral stem. The block can distribute the forces between the neck and the set screw across a broader surface, to more effectively lock the position of the neck. While FIGS. 24A-24F show a pair of set screw receiving regions radially offset from one another by about 180°, the locking mechanism may comprise any number of set screws distributed in any appropriate configuration. For example, the femoral head may comprise three set screw receiving regions radially offset from one another by about 120°, or four set screw receiving regions radially offset from one another by about 90°.

Figure 24C:
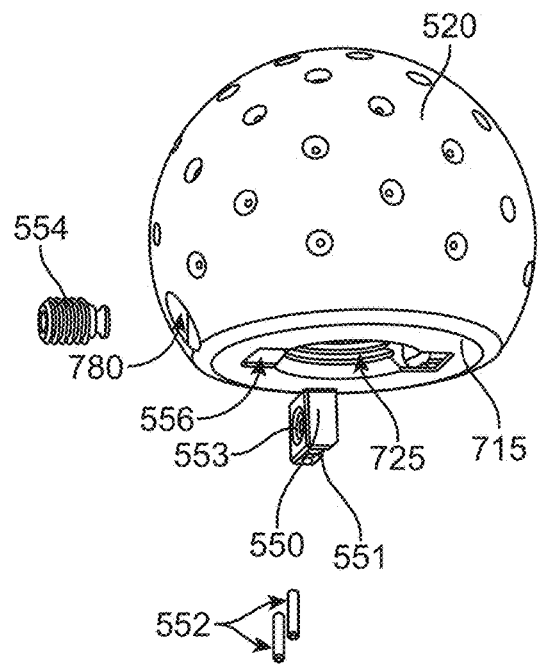
FIGS. 24C-24F illustrate a method of assembling the locking mechanism of FIGS. 24A and 24B.
Figure 24D:
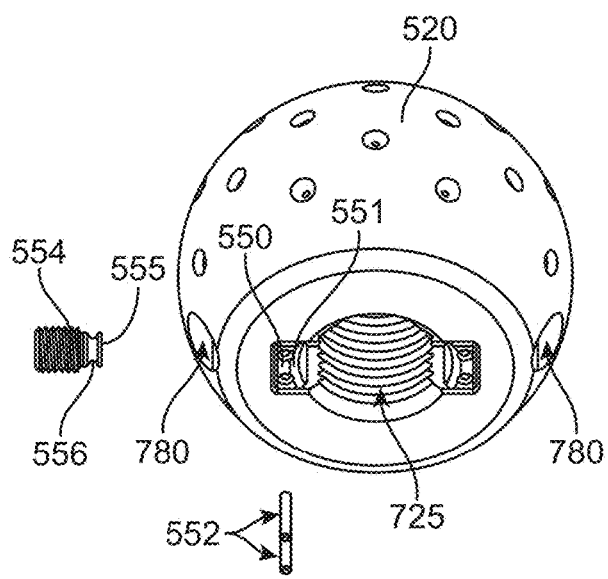
Figure 24E:
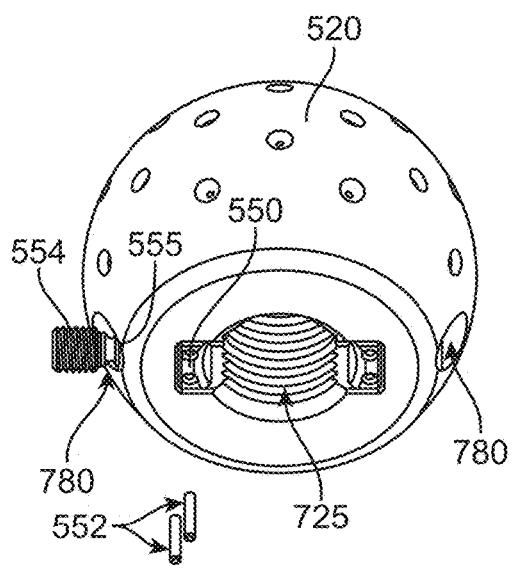
Figure 24F:
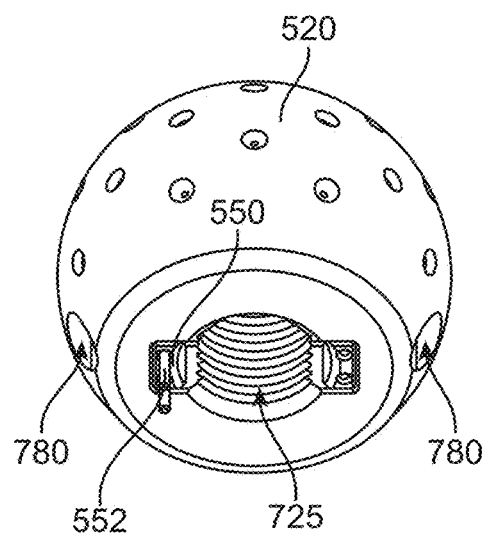

FIGS. 24C-24F illustrate a method of assembling the locking mechanism of FIGS. 24A and 24B. FIG. 24C shows the femoral head 520 and components of the locking mechanism before assembly. As described previously, the femoral head may comprise one or more set screw receiving regions 780 extending radially outwards from the central channel 725. Each set screw receiving region can be configured to receive a set screw 554, a block 550, and a pair of dowel pins 552. FIG. 24D shows the first step of assembly of the locking mechanism, wherein the block 550 is coupled to the femoral head 520. The femoral head may comprise a block receiving region 556 adjacent the central channel 725, and the block may be inserted into block receiving region from the base 715 of the femoral head. As best seen in FIG. 24B, the block 550 may have a concave surface 551 on a first end and a round indent 553 on a second end opposite the first end. As shown in FIG. 24C, the block may be inserted into the femoral head with the concave surface directed radially inwards, facing the central channel, and the round indent directed radially outwards. FIG. 24E shows the second step of assembly of the locking mechanism, wherein the set screw 554 is coupled to the femoral head 520. As best seen in FIG. 24B, the set screw receiving region 780 comprises set screw threads 785, configured to engage the thread region of the set screw. The set screw may be threadably engaged with the set screw threads within the set screw receiving region, to translate the set screw radially inwards within the set screw receiving region. As best seen in FIG. 24D, the set screw can comprise a set screw head 555, an unthreaded region of the set crew having a smaller diameter than the threaded region of the set screw. During the step shown in FIG. 24E, the set screw can be translated radially inwards until the set screw head is disposed within the round indent 553 of the block 550 (as best seen in FIG. 24B). FIG. 24F shows the final step of assembly of the locking mechanism, wherein the dowel pins 552 are coupled to the femoral head. The two dowel pins may be pressed into the block 550 with an interference fit. When the dowel pins are pressed completely into the block, the leading ends of pins can engage the set screw head 555, such that the pins prevent the set screw from separating from the block. For example, the screw head may comprise a concave groove 557 (as best seen in FIGS. 24B and 24D) extending about the circumference of the set screw head 555. The leading ends of the dowel pins may be configured to engage the concave groove when the pins are pressed completely into the block (as best seen in FIG. 24B) such that the set screw cannot separate from the block.

Optional Features

Figure 25A:
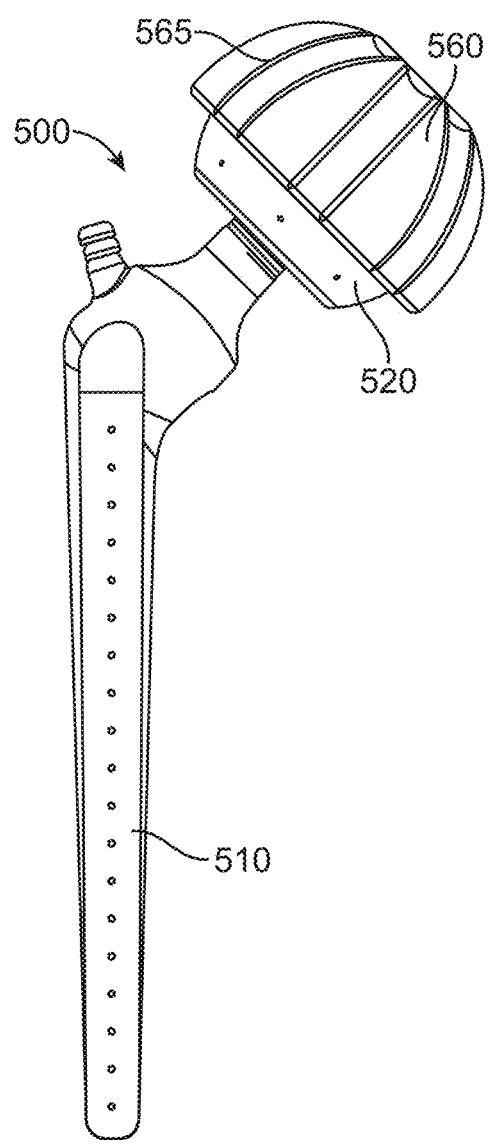
FIGS. 25A and 25B show an exemplary embodiment of a therapeutic agent delivery system having an acetabular cup.
Figure 25B:
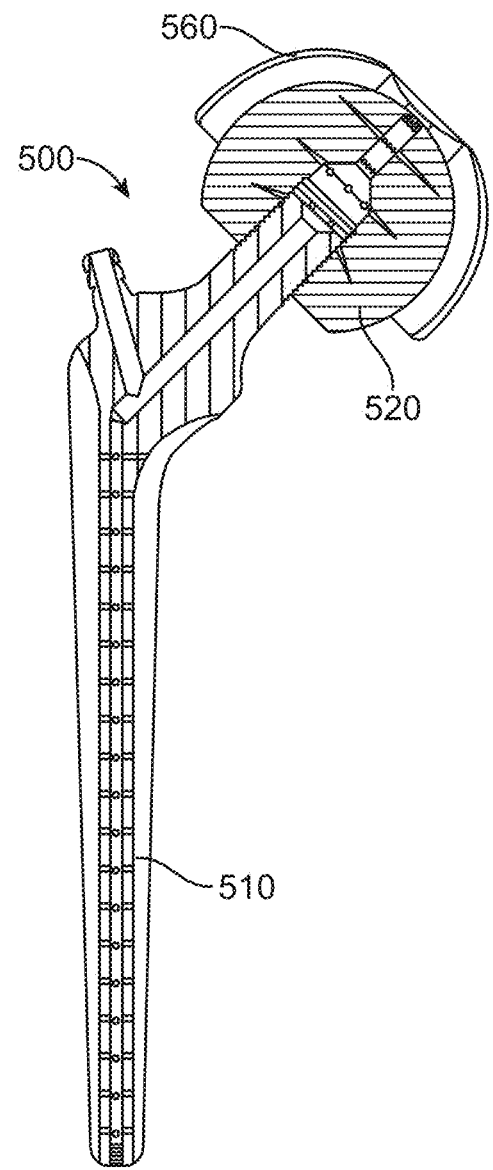

FIGS. 25A and 25B show an exemplary embodiment of a therapeutic agent delivery system 500 for a hip, further comprising an acetabular cup 560. FIG. 25A is a perspective view and FIG. 25B is a side cross sectional view of the system 500. The delivery system 500 may further comprise a separate acetabular cup 560, configured to be inserted into the acetabular space of the hip joint. The femoral head 520 thus interfaces with the acetabular cup, rather than interfacing directly with the acetabulum of the patient. The acetabular cup may comprise a plurality of fluted external structures 565, through which fluid may flow to reach the acetabulum.

Figure 26:
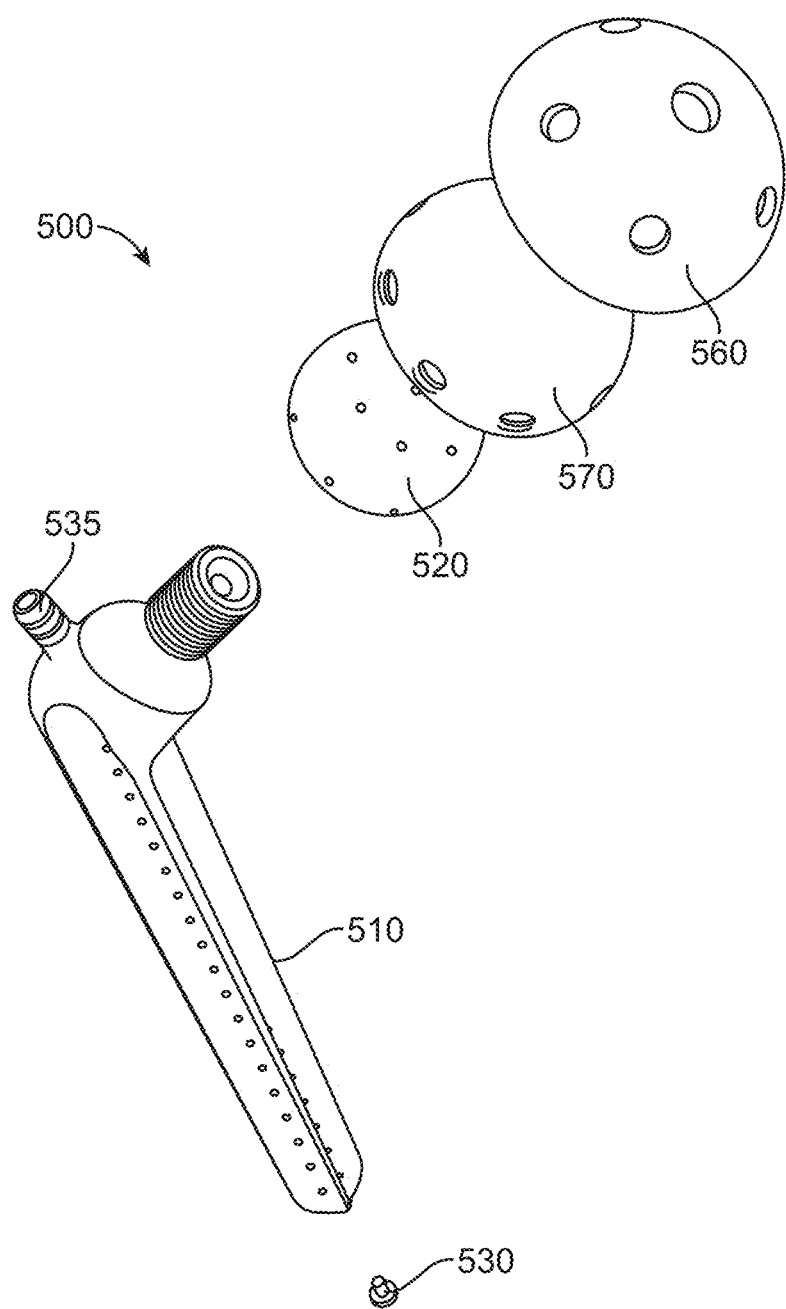
FIG. 26 shows an exemplary embodiment of a therapeutic agent delivery system for a hip.

FIG. 26 shows an exemplary embodiment of a therapeutic agent delivery system 500 for a hip. The therapeutic agent delivery system 500 as described herein may be configured to function as the final implant, rather than as a temporary implant intended for the first stage of a two-stage re-implantation procedure. The system 500 may comprise a femoral stem 510 such as any femoral stem described herein, a femoral head 520 such as any femoral head described herein, and a stem plug 530. In addition, the system 500 may further comprise a liner 570 and an acetabular cup 560 configured to be implanted between the femoral head 520 and the acetabulum of the patient. Fluid may flow through the femoral head and out the liner and acetabular cup, into the joint space and the acetabulum. Optionally, alternatively to or in combination with the inlet 535 of the femoral stem 510, the acetabular cup 560 may comprise a separate inlet, through which the therapeutic agent may be supplied.

Method of Use of Therapeutic Agent Delivery System for Hip

Figure 27:
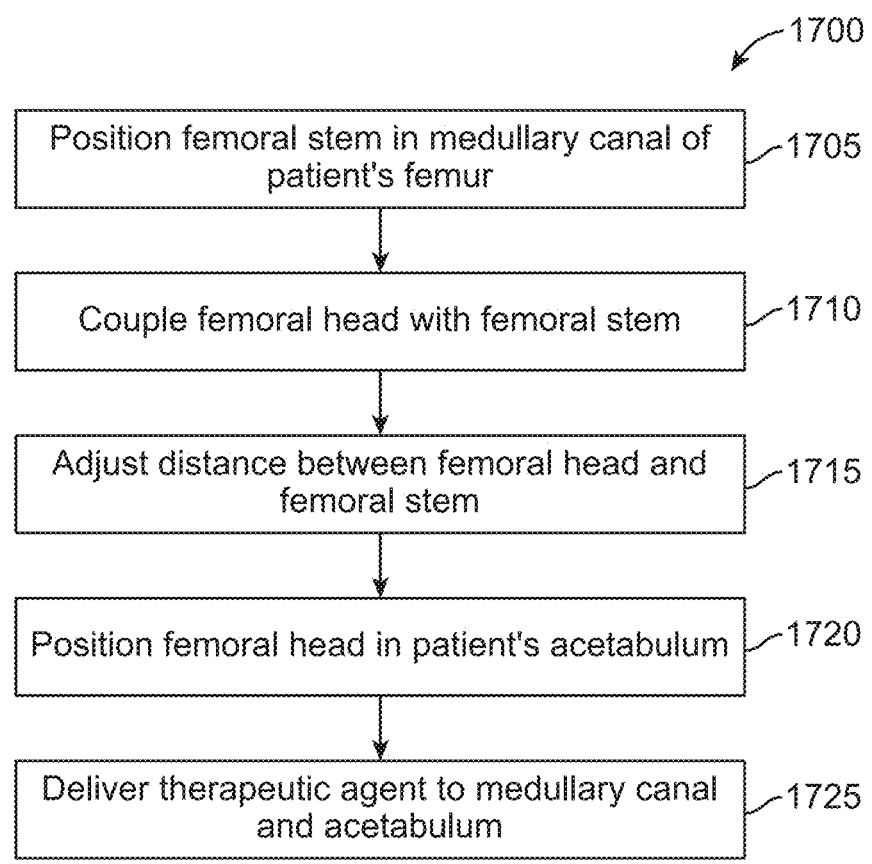
FIG. 27 shows a method of treating a hip using a therapeutic agent delivery system.

FIG. 27 illustrates a method 1700 of treating a patient's hip using a therapeutic agent delivery system for a hip as described herein. In step 1705, a femoral stem is positioned in the medullary canal of the patient's femur. In step 1710, a femoral head is coupled to the femoral stem. In step 1715, which is optional, the distance between the femoral stem and the femoral head is adjusted such that the delivery system best fits the patient's anatomy. For example, if the femoral head is coupled to the femoral stem via a threaded connection mechanism as described herein, the distance between the femoral stem and head may be adjusted by threadably rotating the femoral head about the stem. Step 1715 may further comprise locking the distance between the femoral head and the femoral stem, for example via the set screw mechanism described in relation to FIGS. 24A-24F. In step 1720, the femoral head is positioned in the patient's acetabulum. In step 1725, the therapeutic agent is delivered to the medullary canal and the acetabulum via the delivery system.

The steps of method 1700 are provided as examples of a method of using a therapeutic agent delivery system in accordance with embodiments. A person of ordinary skill in the art will recognize many variations and modifications of the method 1700 based on the disclosure provided herein. For example, some steps may be added or removed. Some of the steps may comprise sub-steps. Many of the steps may be repeated as many times as appropriate or necessary. One or more steps may be performed in a different order than as illustrated in FIG. 27. For example, the femoral head and the femoral stem may be coupled together and, if necessary, the distance between the head and stem adjusted, before the assembled device is positioned in the patient's femur and acetabulum.

Additional Features of Therapeutic Agent Delivery Systems

In any of the therapeutic agent delivery systems described herein, the flow of fluid within the system may be adjusted by modifying one or more dimensions or configurations of the channels and/or outlet holes. For example, the diameter of the channels and/or outlet holes may be increased or decreased, or channels may be configured to have varying diameters along the length of the assembly, to bias the flow of fluid in a particular direction. Angles at junctures between the channels may also be varied to bias fluid flow within the system.

Any therapeutic agent delivery system as described herein may further comprise a pump, operatively coupled to the inlet. The pump may be configured to pump the therapeutic agent into one or more channels of the system.

Any therapeutic agent delivery system as described herein may optionally comprise a vacuum pump that may be coupled to an inlet or an outlet of the system. The vacuum pump may be configured to remove any unwanted or excess fluids from the body of the patient, before introducing the therapeutic agent to the body using the delivery system.

Any therapeutic agent delivery system as described herein may optionally comprise a port under the skin that is coupled to an inlet or outlet of the delivery system. The port may be accessed via a needle or syringe as necessary.

FIGS. 28A and 28B illustrate the use of negative pressure wound therapy with a therapeutic agent delivery system for a knee. Negative pressure wound therapy may optionally be used in tandem with the therapeutic agent delivery system, in order to further improve the prognosis of the treatment. The wound of the patient can be packed with sponges 90 and optionally covered with a wound dressing 85 coupled to a vacuum pump 80. Actuation of the vacuum pump can then draw blood and nutrients to infected areas. As shown in FIG. 28B, optional sponges for negative pressure wound therapy may also be provided as strips 95 of sponges configured to be disposed along the intramedullary stems 200 of the delivery system 100. The strips of sponges may be trimmed to fit the space along the fluted regions 235 of any intramedullary stem 200. Negative pressure wound therapy can pull material through the sponge and into the plurality of outlet holes of the stem, into the stem channel, and out of the body through the inlet or outlet of the system. While a delivery system for a knee is shown in FIGS. 28A and 28B, negative pressure wound therapy may be used with any therapeutic agent delivery system as described herein, including delivery systems for joints other than the knee.

Figure 29:
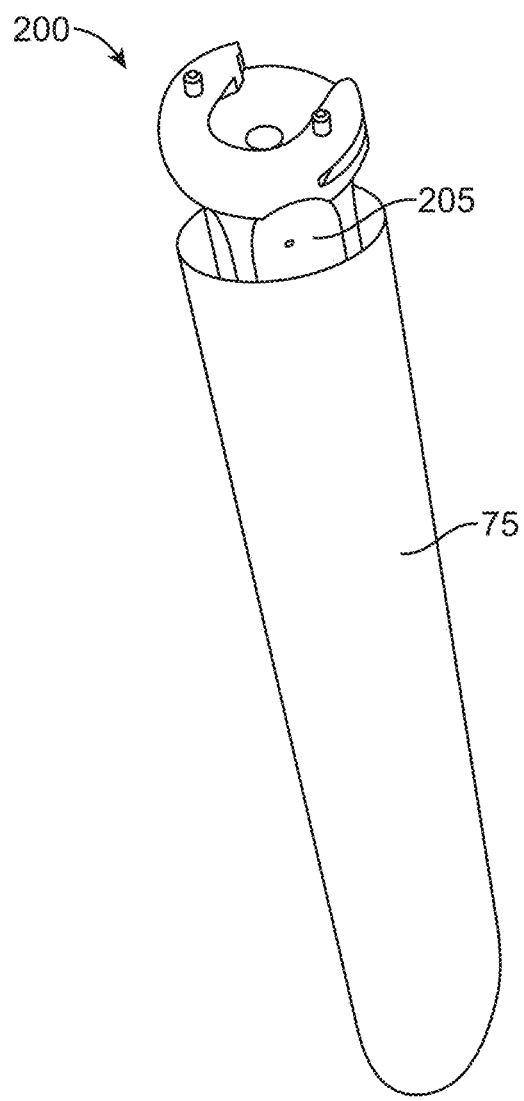
FIG. 29 shows an optional cover for an intramedullary stem.

FIG. 29 shows an optional cover 75 for an intramedullary stem 200, suitable for incorporation with any therapeutic agent delivery system described herein. The cover 75 may comprise a thin, cone-shaped sponge, configured to fit inside the medullary canal as an interface between the bone and the intramedullary stem 200. The cover can be configured to cover the substantially all of the elongate body 205 of the stem, and thus evenly interface with the intramedullary bone. When covered with the cover 75, the therapeutic agent can disperse within the cover and reach the corresponding surface of the medullary canal, regardless of the shape of the intramedullary stem (e.g., shape, size, number, or configuration of protrusions and fluted regions). This exemplary configuration may also be used in conjunction with the negative pressure wound therapy previously described.

Figure 30:
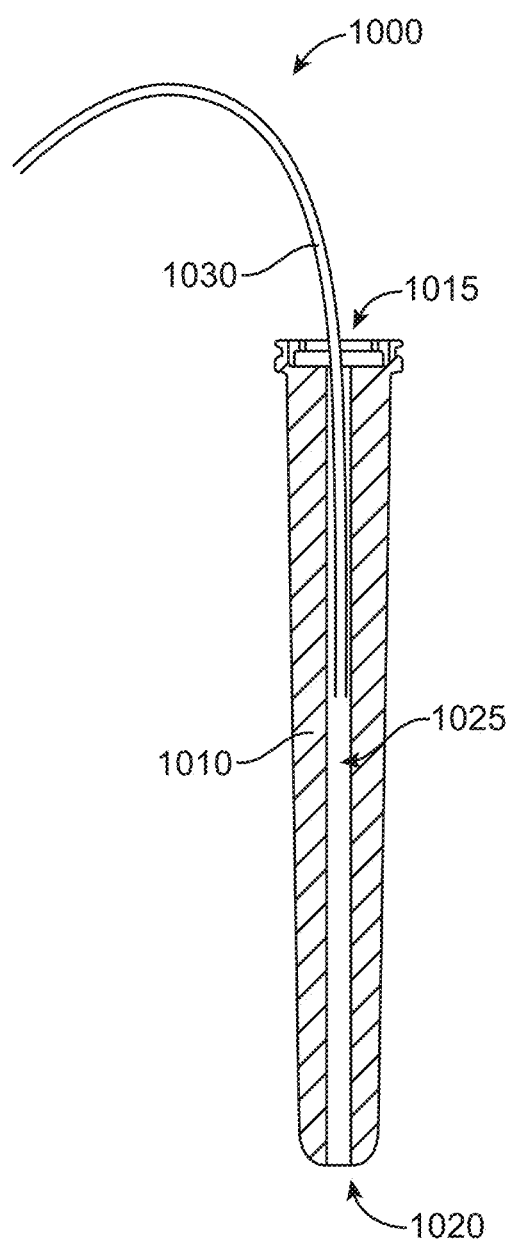
FIG. 30 shows an exemplary embodiment of a therapeutic agent delivery system.

FIG. 30 shows an exemplary embodiment of a therapeutic agent delivery system 1000. The delivery system 1000 may comprise an intramedullary stem 1010 which may be any intramedullary stem as described herein, such as intramedullary stems 110, 120, or 200, or femoral stems 510 or 600. The stem 1010 may comprise a stem channel 1025 that extends through both the first end 1015 and the second end 1020 of the stem. Instead of receiving the therapeutic agent from a coupling member coupled to the stem, the stem 1010 may be configured to receive a catheter 1030 supplying the therapeutic agent through the first end 1015. The therapeutic agent may be delivered to the medullary canal through the second end 1020.

Figure 31A:
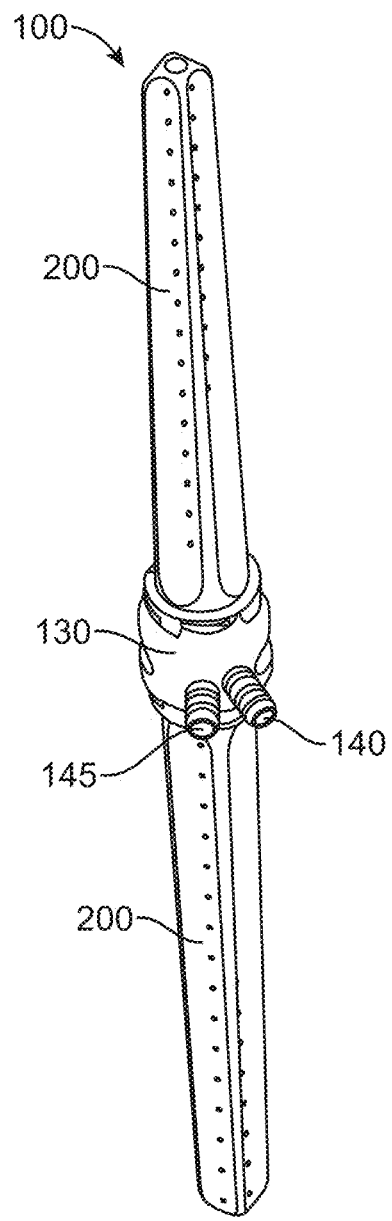
FIGS. 31A and 31B show exemplary embodiments of therapeutic agent delivery systems with inlets and outlets.
Figure 31B:
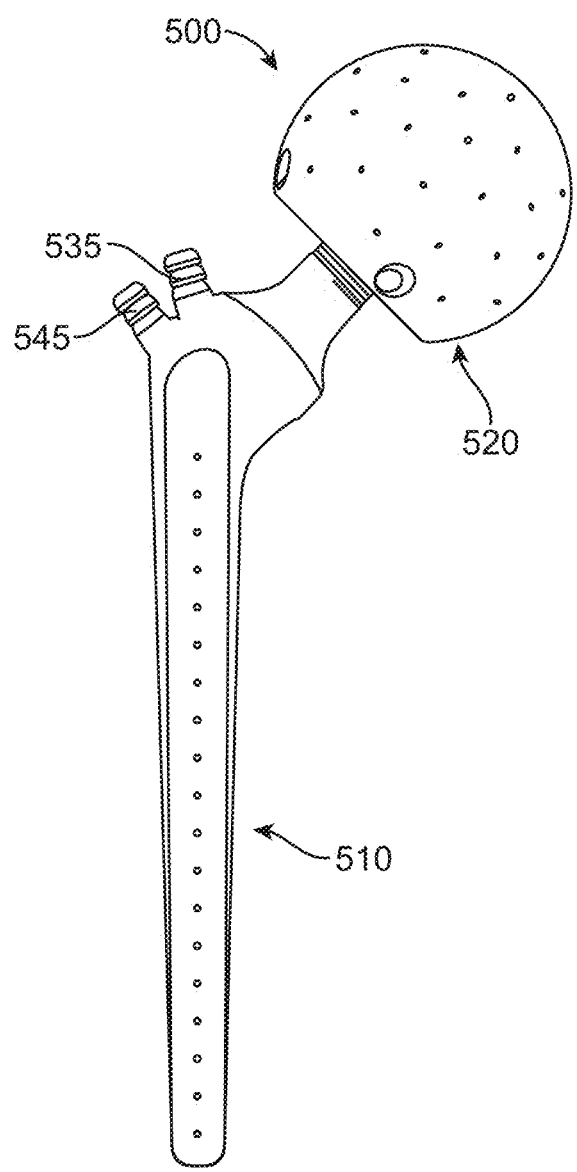

FIGS. 31A and 31B show exemplary embodiments of therapeutic agent delivery systems with inlets and outlets. FIG. 31A shows an exemplary embodiment of a therapeutic agent delivery system 100 for a knee, as described herein. The delivery system 100 may comprise an inlet 140, configured to couple to a source of the therapeutic agent. The inlet 140 may be fluidly coupled to one or more channels of a coupling member 130, and the one or more channels of the coupling member may be fluidly coupled to the stem channels in the stems 200. Optionally, the system may further comprise an outlet 145, configured to remove the therapeutic agent and/or any other fluid from the body. The stems and the coupling member may comprise internal channels configured to direct fluid between the inlet and the stem channel, and between the stem channel and the outlet. Other aspects of the system may generally take the same form as previously described. FIG. 31B shows an exemplary embodiment of a therapeutic agent delivery system 500 for a hip, as described herein. The delivery system 500 may comprise an inlet 535, configured to couple to a source of the therapeutic agent. The inlet 535 may be fluidly coupled to a channel of the femoral stem 510, and the stem channel may be fluidly coupled to a central channel of the femoral head 520 coupled to the femoral stem. Optionally, the system may further comprise an outlet 545, configured to remove the therapeutic agent and/or any other fluid from the body. The femoral stem and the femoral head may comprise internal channels configured to direct fluid between the inlet and the channels of the stem and the head, and between the outlet and the channels of the stem and the head. Other aspects of the system may generally take the same form as previously described.

FIGS. 32A and 32B illustrate an exemplary configuration for the internal channels of an intramedullary stem. FIG. 32A is a sectional view and FIG. 32B is a cross sectional view of an intramedullary stem 1100 comprising a plurality of separate internal fluid paths. Stem 1100 may comprise any intramedullary stem as described herein, such as intramedullary stems 110, 120, or 200, or femoral stems 510 or 600. Stem 1100 may comprise a first internal channel 1110 centrally disposed along the longitudinal axis of the stem, and a second internal channel 1120 disposed about the periphery of the first internal channel (the second internal channel can form the shape of a cylindrical shell surrounding the first internal channel). The first internal channel may be fluidly coupled to a first plurality of outlet holes 1115, each of the first plurality of outlet holes extending from the first internal channel, through the second internal channel, to an outer wall of the stem (such as a fluted region 1135 of the stem). The second internal channel may be fluidly coupled to a second plurality of outlet holes 1125, each of the second plurality of outlet holes extending from the second internal channel directly to an outer wall of the stem. The first internal channel and the second internal channel may be fluidly sealed against one another, and each of the first plurality of outlet holes 1115 may cross over the second internal channel 1120 through a side channel that is fluidly sealed against the second internal channel. Therefore, the first internal channel and the second internal channel can form two separate internal fluid paths, each of which can be used to deliver fluid to the tissue or remove fluid from the tissue. As shown in FIG. 32B, the first plurality of outlet holes 1115 and the second plurality of outlet holes 1125 may be linearly arranged along the length of the stem in an alternating manner, such that every other hole is in fluid communication with a different internal fluid path.

FIGS. 33A-33C illustrate another exemplary configuration for the internal channels of an intramedullary stem. FIG. 33A is a perspective view, FIG. 33B is a vertical cross sectional view, and FIG. 33C is a horizontal cross sectional view of an intramedullary stem 1200 comprising a plurality of separate internal fluid paths. Stem 1200 may comprise any intramedullary stem as described herein, such as intramedullary stems 110, 120, or 200, or femoral stems 510 or 600. Stem 1200 may comprise a first internal channel 1210 running along the length of the stem, and a second internal channel 1220 adjacent the first internal channel, also running along the length of the stem. The first and second internal channels may be fluidly sealed against one another, such that each channel forms a separate internal fluid path. The first internal channel may be fluidly coupled to a first plurality of outlet holes 1215, each of the first plurality of outlet holes extending from the first internal channel to an outer wall of the stem (such as a fluid region 1235 of the stem), without cutting through the second internal channel. The second internal channel may be fluidly coupled to a second plurality of outlet holes 1225, each of the second plurality of outlet holes extending from the second internal channel to an outer wall of the stem, without cutting through the first internal channel. Therefore, the first internal channel and the second internal channel can form two separate internal fluid paths, each of which can be used to deliver fluid to the tissue or remove fluid from the tissue. As shown in FIG. 33A, the first plurality of outlet holes 1215 and the second plurality of outlet holes 1225 may be arranged along the length of the stem in an alternating manner, such that every other hole is in fluid communication with a different internal fluid path.

An intramedullary stem comprising two or more separate internal fluid paths as shown in FIGS. 32A-33C may be used to simultaneously deliver fluid to and remove fluid from the tissue, without cross-contaminating the fluid to be delivered with the fluid to be removed. For example, a first internal channel may be fluidly coupled to an inlet (such as inlet 140 of FIG. 31A or inlet 535 of FIG. 31B) configured to receive a therapeutic agent from a source, while the second internal channel may be fluidly coupled to an outlet (such as outlet 145 of FIG. 31A or outlet 545 of FIG. 31B) configured to remove fluid from the tissue. In this configuration, the first plurality of outlet holes can deliver the therapeutic agent to the tissue, while the second plurality of outlet holes can remove fluid from the tissue, thereby allowing simultaneous delivery of therapeutic agent and removal of fluid from the tissue without cross-contamination between the therapeutic agent and the fluid to be removed. In another exemplary configuration, the first internal channel may be fluidly coupled to a first inlet configured to receive a first therapeutic agent, while the second internal channel may be fluidly coupled to a second inlet configured to receive a second therapeutic agent different from the first therapeutic agent. In this configuration, simultaneous delivery of two different therapeutic agents can be achieved, without cross-contamination between the two agents before the agents reach the tissue.

FIGS. 34-36 show exemplary embodiments of therapeutic agent delivery systems adapted for use in various joints. While descriptions of the therapeutic agent delivery systems are primarily directed to systems to be used in the knee or in the hip, systems comprising similar components and features may be used to treat any other joint. FIG. 34 shows an exemplary embodiment of a delivery system 1200 for a shoulder, FIG. 35 shows an exemplary embodiment of a delivery system 1300 for an ankle, and FIG. 36 shows an exemplary embodiment of a delivery system 1400 for a spine. In the embodiments shown, the delivery systems 1200, 1300, and 1400 comprise an inlet 140 through which the therapeutic agent may be supplied, and a plurality of outlet holes 240 through which the therapeutic agent may be delivered to the respective location of the body. Any of the delivery systems 1200, 1300, and 1400 may incorporate any other structures or features disclosed herein in relation to delivery systems for the knee and the hip.

Components of the therapeutic agent delivery systems as described herein may be formed from one or more of many materials commonly used in orthopedic implants, including but not limited to titanium alloy Ti 6Al-4V, polyether ether ketone (PEEK), polymethyl methacrylate (PMMA), and ultra high molecular weight polyethylene (UHMWPE). The materials may incorporated an antibiotic-impregnated outer layer, such as an antibiotic-impregnated PMMA outer layer. The surface of the components may be polished to prevent bone growth and formation of biofilms. Alternatively, the surface of the components may be grit-blasted or plasma-sprayed, incorporate one or more of an hyaluronic acid (HA) coating, silver coating, or antibiotic carrier coating, or be passivated and irradiated to form a hydrophilic nanostructure. The delivery systems as described herein may comprise one or more of machined parts or sintered parts.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A fluid delivery system for disinfecting a joint after removal of a prosthesis from said joint, said system comprising:
    a femoral head configured to be disposed in an acetabulum, the femoral head comprising:
        a partially spherical, outer shell forming an external surface of the femoral head, the outer shell comprising a plurality of outlets and a first radius of curvature;
        a partially spherical, inner shell located internal to the outer shell, the inner shell comprising a second radius of curvature smaller than the first radius of curvature;
        a central shaft projecting through the interior of the femoral head, the central shaft coupled to a region of the inner shell and defining a central channel;
        an outer cavity disposed near a periphery of the femoral head, the outer cavity bound by an inner surface of the outer shell and an outer surface of the inner shell, wherein the outer cavity is in fluid communication with the central channel and the plurality of outlets; and
        an inner cavity located inside the femoral head internal to the outer cavity, wherein the inner cavity is defined, in part, by an inner surface of the inner shell, wherein the inner cavity is not in fluid communication with any of the central channel, the outer cavity, or the plurality of outlets;
    a femoral stem coupled to the femoral head so as to be in fluid communication with the central channel, the femoral stem configured to be disposed in a femoral medullary canal, wherein the femoral stem comprises a threaded neck region, the threaded neck region configured to be threadably engaged with the femoral head thereby allowing adjustment of a distance between the femoral head and the femoral stem; and
    an inlet coupled to the femoral stem,
    wherein, when the system receives a fluid from the inlet, the fluid is deliverable from the plurality of outlets into the acetabulum.

2. The system of claim 1, wherein the femoral stem comprises a plurality of protrusions extending axially along a longitudinal axis of the femoral stem.

3. The system of claim 1, wherein the femoral stem comprises an elongate channel extending therethrough, the elongate channel fluidly coupled with the inlet and the plurality of outlets.

4. The system of claim 3, wherein the elongate channel is a through-hole, and wherein one end of the femoral stem comprises a plug.

5. The system of claim 1, wherein the femoral stem is tapered.

6. The system of claim 1, wherein the central channel is fluidly coupled with the plurality of outlets via a plurality of channels extending radially outward from the central channel.

7. The system of claim 1, further comprising an outlet for fluid removal from the femoral head or the femoral stem.

8. The system of claim 1, further comprising an acetabular cup coupled to the femoral head, and wherein the fluid is delivered from the acetabular cup to the acetabulum.

9. The system of claim 1, wherein the plurality of outlets comprise a plurality of holes having varying diameters.

10. The system of claim 1, further comprising a locking mechanism for locking the femoral head with the femoral stem.

11. The system of claim 1, further comprising a plurality of outlets in the femoral stem that are in fluid communication with the inlet.

12. The system of claim 1, wherein the femoral head is configured to be removably disposed in the acetabulum for use in a two-stage re-implantation procedure.

13. The system of claim 1, wherein the inner shell is connected to the outer shell via a plurality of support struts.

14. A method for treating a joint using the system of claim 1, said method comprising:
    positioning the femoral stem in the femoral medullary canal of a femur;
    coupling the femoral head with the femoral stem;
    positioning the femoral head in the acetabulum; and
    delivering the fluid to the medullary canal and the acetabulum.

15. The method of claim 14, wherein coupling comprises adjusting a distance between the femoral head and the femoral stem.

16. The method of claim 14, wherein delivering the fluid comprises delivering an antibiotic, saline, or irrigation fluid.

17. The method of claim 14, wherein delivering the fluid comprises delivering an antibiotic, the antibiotic comprising vancomycin, tobramycin, or a combination thereof.

18. The method of claim 14, wherein delivering the fluid comprises delivering the fluid from one or more outlet holes disposed in a fluted region of the femoral stem.

19. The method of claim 14, wherein delivering the fluid comprises pumping the fluid from the femoral stem to the medullary canal or from the femoral head to the acetabulum.

20. The method of claim 14, further comprising suctioning unwanted fluids from the medullary canal or the acetabulum.

* * * * *